(12) United States Patent
Zarrin et al.

(10) Patent No.: US 10,160,807 B2
(45) Date of Patent: Dec. 25, 2018

(54) METHODS OF TREATING INFLAMMATORY DISEASES BY ADMINISTERING ANTI-PILR-ALPHA ANTIBODY

(71) Applicant: Genentech, Inc., South San Francisco, CA (US)

(72) Inventors: Ali Zarrin, Brisbane, CA (US); Yonglian Sun, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/397,399

(22) Filed: Jan. 3, 2017

(65) Prior Publication Data

US 2017/0137518 A1    May 18, 2017

Related U.S. Application Data

(60) Division of application No. 14/598,870, filed on Jan. 16, 2015, now Pat. No. 9,556,269, which is a continuation of application No. 13/921,557, filed on Jun. 19, 2013, now abandoned, which is a continuation of application No. PCT/US2011/066753, filed on Dec. 22, 2011.

(60) Provisional application No. 61/510,453, filed on Jul. 21, 2011, provisional application No. 61/426,945, filed on Dec. 23, 2010.

(51) Int. Cl.
  C07K 16/28    (2006.01)
  G01N 33/566   (2006.01)
  A61K 39/395   (2006.01)

(52) U.S. Cl.
  CPC ...... C07K 16/2803 (2013.01); A61K 39/3955 (2013.01); C07K 16/28 (2013.01); G01N 33/566 (2013.01); C07K 2317/76 (2013.01)

(58) Field of Classification Search
  CPC .................. C07K 16/2803; C07K 2317/76
  See application file for complete search history.

(56) References Cited

U.S. PATENT DOCUMENTS

2010/0129347 A1    5/2010  Arase et al.
2014/0037627 A1    2/2014  Banerjee et al.

FOREIGN PATENT DOCUMENTS

EP    0307247 B1    8/1994

OTHER PUBLICATIONS

Wang J, et al. (Jan. 2013). Nature Immunology. 14(1):34-42. (doi:10.1038/ni.2456; published online Nov. 11, 2012).*

Banerjee et al., "Modulation of paired immunoglobulin-like type 2 receptor signaling alters the host response to Staphylococcus aureus-induced pneumonia," Infect Immun. 78(3):1353-63 (2010).
Carlin et al., "Molecular mimicry of host sialylated glycans allows a bacterial pathogen to engage neutrophil Siglec-9 and dampen the innate immune response," Blood. 113(14):3333-6 (2009).
Clark et al., "2D depiction of protein-ligand complexes," J Chem Inf Model. 47(5):1933-44 (2007).
Crocker et al., "Siglecs and their roles in the immune system," Nat Rev Immunol. 7(4):255-66 (2007).
Diefenbach et al., "Innate immune recognition by stimulatory immunoreceptors," Curr Opin Immunol. 15(1):37-44 (2003).
Evrard et al., "Functional analysis of the NPDC-1 gene," Gene. 343(1):153-63 (2004).
Evrard et al., "Subcellular localization of neural-specific NPDC-1 protein," J Neurosci Res. 79(6):747-55 (2005).
Fan et al., "Differential effects on cell fusion activity of mutations in herpes simplex virus 1 glycoprotein B (gB) dependent on whether a gD receptor or a gB receptor is overexpressed," J Virol. 83(15):7384-90 (2009).
Fan et al., "The Ig-like v-type domain of paired Ig-like type 2 receptor alpha is critical for herpes simplex virus type 1-mediated membrane fusion," J Virol. 84(17):8664-72 (2010).
Fournier et al., "FDF03, a novel inhibitory receptor of the immunoglobulin superfamily, is expressed by human dendritic and myeloid cells," J Immunol. 165(3):1197-209 (2000).
Galiana et al., "Identification of a neural-specific cDNA, NPDC-1, able to down-regulate cell proliferation and to suppress transformation," Proc Natl Acad Sci USA. 92(5):1560-4 (1995).
Gelin et al., "The E2 antigen, a 32 kd glycoprotein involved in T-cell adhesion processes, is the MIC2 gene product," EMBO J. 8(11):3253-9 (1989).
Ikehara et al., "Negative regulation of T cell receptor signaling by Siglec-7 (p70/AIRM) and Siglec-9," J Biol Chem. 279(41):43117-25 (2004).
Janssen et al., "Surfactant proteins A and D suppress alveolar macrophage phagocytosis via interaction with SIRP alpha," Am J Respir Crit Care Med. 178(2):158-67 (2008).
Julenius et al., "Prediction, conservation analysis, and structural characterization of mammalian mucin-type O-glycosylation sites," Glycobiology. 15(2):153-64 (2005).
Kogure et al., "PANP is a novel O-glycosylated PILRalpha ligand expressed in neural tissues," Biochem Biophys Res Commun. 405(3):428-33 (2011).
Lanier, "On guard—activating NK cell receptors," Nat Immunol. 2(1):23-7 (2001).
Liu et al., "Characterization of a novel C-type lectin-like gene, LSECtin: demonstration of carbohydrate binding and expression in sinusoidal endothelial cells of liver and lymph node," J Biol Chem. 279(18):18748-58 (2004).
May et al., "Crystal structure of the N-terminal domain of sialoadhesin in complex with 3' sialyllactose at 1.85 A resolution," Mol Cell. 1(5):719-28 (1998).

(Continued)

*Primary Examiner* — Robert S Landsman
(74) *Attorney, Agent, or Firm* — Clark & Elbing LLP; Karen L. Elbing

(57) ABSTRACT

Described herein is a novel receptor-ligand interaction and agents that may modify and/or block the interaction. Methods, uses, reagents and kits for the modulation of ligand activities related to its interaction with the novel receptor are disclosed. Also disclosed are therapeutic uses of reagents in treating inflammation-related disorders.

7 Claims, 26 Drawing Sheets

Specification includes a Sequence Listing.

(56) References Cited

OTHER PUBLICATIONS

Moretta et al., "Activating receptors and coreceptors involved in human natural killer cell-mediated cytolysis," Annu Rev Immunol. 19:197-223 (2001).
Mousseau et al., "PILRalpha, a novel immunoreceptor tyrosine-based inhibitory motif-bearing protein, recruits SHP-1 upon tyrosine phosphorylation and is paired with the truncated counterpart PILRbeta," J Biol Chem. 275(6):4467-74 (2000).
Munday et al., "Sialic acid binding receptors (siglecs) expressed by macrophages," J Leukoc Biol. 66(5):705-11 (1999).
Nakamura et al., "Molecular cloning and functional characterization of a human scavenger receptor with C-type lectin (SRCL), a novel member of a scavenger receptor family," Biochem Biophys Res Commun. 280(4):1028-35 (2001).
Nathan et al., "Ceftriaxone as effective as long-acting chloramphenicol in short-course treatment of meningococcal meningitis during epidemics: a randomised non-inferiority study," Lancet. 366(9482):308-13 (2005).
North et al., "Glycomics profiling of Chinese hamster ovary cell glycosylation mutants reveals N-glycans of a novel size and complexity," J Biol Chem. 285(8):5759-75 (2010).
Novak et al., "Expression of BCMA, TACI, and BAFF-R in multiple myeloma: a mechanism for growth and survival," Blood. 103(2):689-94 (2004).
Novak et al. "Expression of BLyS and its receptors in B-cell non-Hodgkin lymphoma: correlation with disease activity and patient outcome," Blood. 104(8):2247-53 (2004).
Ohtani et al., "The membrane-type collectin CL-P1 is a scavenger receptor on vascular endothelial cells," J Biol Chem. 276(47):44222-8 (2001).
Olson et al., "A MUC1 tandem repeat reporter protein produced in CHO-K1 cells has sialylated core 1 O-glycans and becomes more densely glycosylated if coexpressed with polypeptide-GalNAc-T4 transferase," Glycobiology. 15(2):177-91 (2005).
Satoh et al., "HSV-1 infection through inhibitory receptor, PILRalpha," Proceedings of the Japanese Society for Immunology (JSI) (abstract 1-E-W9-22-O/P), 37:78 (Oct. 25, 2007) (1 page).
Satoh et al., "PILRalpha is a herpes simplex virus-1 entry coreceptor that associates with glycoprotein B," Cell. 132(6):935-44 (2008).
Shiratori et al., "Activation of natural killer cells and dendritic cells upon recognition of a novel CD99-like ligand by paired immunoglobulin-like type 2 receptor," J Exp Med. 199(4):525-33 (2004).
Smith et al., "Murine natural killer cell activation receptors," Immunol Rev. 181:115-25 (2001).
Sun et al., "Evolutionarily conserved paired immunoglobulin-like receptor alpha (PILRalpha) domain mediates its interaction with diverse sialylated ligands," J Biol Chem. 287(19):15837-50 (2012).
Tabata et al., "Biophysical characterization of O-glycosylated CD99 recognition by paired Ig-like type 2 receptors," J Biol Chem. 283(14):8893-901 (2008).
Tabata et al., "Expression, crystallization and preliminary X-ray diffraction analysis of human paired Ig-like type 2 receptor alpha (PILRalpha)," Acta Crystallogr Sect F Struct Biol Cryst Commun. 64(Pt 1):44-6 (2008).
Thompson et al., "BAFF-R, a newly identified TNF receptor that specifically interacts with BAFF," Science. 293(5537):2108-11 (2001).
Van Lookeren Campagne et al., "Macrophage complement receptors and pathogen clearance," Cell Microbial. 9(9):2095-102 (2007).
Vinson et al., "Characterization of the sialic acid-binding site in sialoadhesin by site-directed mutagenesis," J Biol Chem. 271(16):9267-72 (1996).
Wang et al., "An essential role of sialylated O-linked sugar chains in the recognition of mouse CD99 by paired Ig-like type 2 receptor (PILR)," J Immunol. 180(3):1686-93 (2008).
Wang et al., "Binding of herpes simplex virus glycoprotein B (gB) to paired immunoglobulin-like type 2 receptor alpha depends on specific sialylated O-linked glycans on gB," J Virol. 83(24):13042-5 (2009).
Yan et al., "Identification of a novel receptor for B lymphocyte stimulator that is mutated in a mouse strain with severe B cell deficiency," Curr Biol. 11(19):1547-52 (2001).
International Search Report and Written Opinion for International Application No. PCT/US2011/066753, dated Aug. 23, 2012 (15 pages).
Sun et al., "PILRα Negatively Regulates Mouse Inflammatory Arthritis," J Immunol. 193(2): 860-870 (2014).

\* cited by examiner

Extracted Motif P-X{0-3}-T-X{0,3}-P

Bioinformatics search using Unison on human proteins with consensus motif P-X{0-3}-T-X{0,3}-P in extra-cellular regions that are not part of a helix or sheet which contain O-Glycosylation site predicted by NetOGlyc 3.1

FIG. 1D

|               |                                                              |     |
|---------------|--------------------------------------------------------------|-----|
| Human PILRα   | YLYGVTQPKHLSASMGGSVEIPFSFYYPWELATAPDVRISWRRGHFHRQS F YSTRPPSIH | 90  |
| Chimp PILRα   | YPYGVTQPKHLSASMGGSVEIPFSFYYPWELATAPDVRISWRRGHFHGQS F YSTRPPSIH | 90  |
| Cow PILRα     | QHYEMKQPRDLSAPEGGSILIPFSFSHPGELAKDPRVSIALKRTHFHGE FIYNTSPLFTH | 87  |
| Dog PILRα     | MDFRMDQPEHLSAPKGGTVHINFTFYYCCGALAKDPRVSIALKRTHFHGE VIYNSTRHFVH | 89  |
| Rat PILRα     | YDYGVDQPAVLSGVQGSSIEIPFSFYFPWNLTKDPQMSIAWRWKNFHGE FIYNSTQPFIH | 90  |
| Mouse PILRα   | NGFGVNQPESCSGVQQGSIDIPFSFYFPWKLAKDPQMSIAWRWKDFHGE FIYNSSLPFIH | 97  |
| Human PILRβ   | YLYGVTQPKHLSASMGGSVEIPFSFYYPWELAIVPNVRISWRRGHFHGQS F YSTRPPSIH | 90  |
| Mouse PILRβ   | NGFGVNQPERCSGVQQGSIDIPFSFYFPWKLAKDPQMSIAWKWKDFHGE VIYNSSLPFIH | 97  |
| Human Siglec1 | ASWGVSSPQDVQGVKGSCLLIPCIFSFPADVEVPDGITAIWYYDYSGQRQVVSHSADPKLVE | 86  |
| Mouse Siglec1 | TTWGVSSSPKNVQGLSGSCLLIPCIFSYPADVPVSNGITAIWYYDYSGKRQVVIHSGDPKLVD | 86  |

|               |                                                              |     |
|---------------|--------------------------------------------------------------|-----|
| Human PILRα   | KDYVNRLFLNWTEGQKSGFLRISNLQKQDQSVYFCRVELDTRSSGRQQWQSIEGTKLSIT | 150 |
| Chimp PILRα   | KDYVNRLFLNWTEGQKSGFLRISNLQKQDQSVYFCRVELDTRSSGRQQWQSIEGTKLSIT | 150 |
| Cow PILRα     | KNFKNRLILNWKEPEKNGSLQISNLRREDQSMYFCRVQLDTLRDGKQKWQSIEGTKLTIT | 147 |
| Dog PILRα     | EDYKDRIILNLPEGQKSGFLQILNLREEDENMYFCRVQLKTQRFGLQVWQSILGTKLTIN | 149 |
| Rat PILRα     | EHFKDRLIMNWTQGQTSGVLRILNLFKKNDQATYFGRVLLQT TEGMKVWQSIPGTNLTVT | 149 |
| Mouse PILRα   | KDYVNRLFLNWTEGQTSGVLRILNLKESDQTRYFGRVFLQT TEGIQFWQSIPGTQLNVT | 156 |
| Human PILRβ   | EHFKDRLIMNWTEGQESGFLRILNLKESDQTRYFGRVFLQT TEGIQFWQSIPGTQLNVT | 150 |
| Mouse PILRβ   | KDYVNRLFLNWTQGQTSGVLRILNLKESDQAQYFSRVNLQS TEGMKLWQSIPGTQLNVT | 156 |
| Human Siglec1 | ARFRGRTEFMGNPEHRVCNLLLKDLQPEDSGSYNFRFEISE VNRWSDVKGTLVTVT | 114 |
| Mouse Siglec1 | KRFRGRAELMGNMDHKVCNLLLKPEDSGTYNFRFEISD SNRWLDVKGTTVTVT | 114 |

PILRα Ligand Expression

| Ligand | Cell |
|---|---|
| NPDC1 | Neurons, T Cells |
| CD99 | Endothelial Cells, Myeloid/Lymphoid/NK |
| APLP1 | CNS |
| COLEC12 | Mono/Mφ, Microglia, Endothelia Cells |
| CLEC4G | Act-Mφ, DC, Kupffer |
| CD23 | Mφ, B Cells, fDC, Platelets |
| Siglec4 | Neuronal Glial Cells |
| Siglec7 | NK, Mφ, DC |
| WDR31 | Spleen, Thymus, Brain |

SEQUENCE LISTING

```
<160> NUMBER OF SEQ ID NOS: 86

<210> SEQ ID NO 1
<211> LENGTH: 302
<212> TYPE: PRT
<213> ORGANISM: Mus sp.

<400> SEQUENCE: 1

Met Ala Leu Leu Ile Ser Leu Pro Gly Gly Thr Pro Ala Met Ala Gln
1               5                   10                  15

Ile Leu Leu Leu Leu Ser Ser Ala Cys Leu His Ala Gly Asn Ser Glu
            20                  25                  30

Arg Ser Asn Arg Lys Asn Gly Phe Gly Val Asn Gln Pro Glu Ser Cys
        35                  40                  45

Ser Gly Val Gln Gly Gly Ser Ile Asp Ile Pro Phe Ser Phe Tyr Phe
    50                  55                  60

Pro Trp Lys Leu Ala Lys Asp Pro Gln Met Ser Ile Ala Trp Arg Trp
65                  70                  75                  80

Lys Asp Phe His Gly Glu Phe Ile Tyr Asn Ser Ser Leu Pro Phe Ile
                85                  90                  95

His Glu His Phe Lys Gly Arg Leu Ile Leu Asn Trp Thr Gln Gly Gln
            100                 105                 110

Thr Ser Gly Val Leu Arg Ile Leu Asn Leu Lys Glu Ser Asp Gln Thr
        115                 120                 125

Arg Tyr Phe Gly Arg Val Phe Leu Gln Thr Thr Glu Gly Ile Gln Phe
    130                 135                 140

Trp Gln Ser Ile Pro Gly Thr Gln Leu Asn Val Thr Asn Ala Thr Cys
145                 150                 155                 160

Thr Pro Thr Thr Leu Pro Ser Thr Thr Ala Ala Thr Ser Ala His Thr
                165                 170                 175

Gln Asn Asp Ile Thr Glu Val Lys Ser Ala Asn Ile Gly Gly Leu Asp
            180                 185                 190

Leu Gln Thr Thr Val Gly Leu Ala Thr Ala Ala Ala Val Phe Leu Val
        195                 200                 205
```

```
Gly Val Leu Gly Leu Ile Val Phe Leu Trp Trp Lys Arg Arg Gln
    210                 215                 220

Gly Gln Lys Thr Lys Ala Glu Ile Pro Ala Arg Glu Pro Leu Glu Thr
225                 230                 235                 240

Ser Glu Lys His Glu Ser Val Gly His Glu Gly Gln Cys Met Asp Pro
                245                 250                 255

Lys Glu Asn Pro Lys Asp Asn Asn Ile Val Tyr Ala Ser Ile Ser Leu
                260                 265                 270

Ser Ser Pro Thr Ser Pro Gly Thr Ala Pro Asn Leu Pro Val His Gly
            275                 280                 285

Asn Pro Gln Glu Glu Thr Val Tyr Ser Ile Val Lys Ala Lys
    290                 295                 300
```

<210> SEQ ID NO 2
<211> LENGTH: 274
<212> TYPE: PRT
<213> ORGANISM: Mus sp.

<400> SEQUENCE: 2

```
Gly Asn Ser Glu Arg Ser Asn Arg Lys Asn Gly Phe Gly Val Asn Gln
1               5                   10                  15

Pro Glu Ser Cys Ser Gly Val Gln Gly Gly Ser Ile Asp Ile Pro Phe
                20                  25                  30

Ser Phe Tyr Phe Pro Trp Lys Leu Ala Lys Asp Pro Gln Met Ser Ile
            35                  40                  45

Ala Trp Arg Trp Lys Asp Phe His Gly Glu Phe Ile Tyr Asn Ser Ser
        50                  55                  60

Leu Pro Phe Ile His Glu His Phe Lys Gly Arg Leu Ile Leu Asn Trp
65                  70                  75                  80

Thr Gln Gly Gln Thr Ser Gly Val Leu Arg Ile Leu Asn Leu Lys Glu
                85                  90                  95

Ser Asp Gln Thr Arg Tyr Phe Gly Arg Val Phe Leu Asn Thr Thr Glu
                100                 105                 110

Gly Ile Gln Phe Trp Gln Ser Ile Pro Gly Thr Gln Leu Asn Val Thr
            115                 120                 125

Asn Ala Thr Cys Thr Pro Thr Thr Leu Pro Ser Thr Thr Ala Ala Thr
130                 135                 140

Ser Ala His Thr Gln Asn Asp Ile Thr Glu Val Lys Ser Ala Asn Ile
145                 150                 155                 160

Gly Gly Leu Asp Leu Gln Thr Thr Val Gly Leu Ala Thr Ala Ala Ala
                165                 170                 175

Val Phe Leu Val Gly Val Leu Gly Leu Ile Val Phe Leu Trp Trp Lys
            180                 185                 190

Arg Arg Arg Gln Gly Gln Lys Thr Lys Ala Glu Ile Pro Ala Arg Glu
        195                 200                 205

Pro Leu Glu Thr Ser Glu Lys His Glu Ser Val Gly His Glu Gly Gln
    210                 215                 220

Cys Met Asp Pro Lys Glu Asn Pro Lys Asp Asn Asn Ile Val Tyr Ala
225                 230                 235                 240

Ser Ile Ser Leu Ser Ser Pro Thr Ser Pro Gly Thr Ala Pro Asn Leu
                245                 250                 255

Pro Val His Gly Asn Pro Gln Glu Glu Thr Val Tyr Ser Ile Val Lys
            260                 265                 270

Ala Lys
```

-continued

```
<210> SEQ ID NO 3
<211> LENGTH: 303
<212> TYPE: PRT
<213> ORGANISM: Homo sapiens

<400> SEQUENCE: 3

Met Gly Arg Pro Leu Leu Leu Pro Leu Leu Pro Leu Leu Leu Pro Pro
1               5                   10                  15

Ala Phe Leu Gln Pro Ser Gly Ser Thr Gly Ser Gly Pro Ser Tyr Leu
            20                  25                  30

Tyr Gly Val Thr Gln Pro Lys His Leu Ser Ala Ser Met Gly Gly Ser
        35                  40                  45

Val Glu Ile Pro Phe Ser Phe Tyr Tyr Pro Trp Glu Leu Ala Thr Ala
 50                  55                  60

Pro Asp Val Arg Ile Ser Trp Arg Arg Gly His Phe His Arg Gln Ser
65                  70                  75                  80

Phe Tyr Ser Thr Arg Pro Pro Ser Ile His Lys Asp Tyr Val Asn Arg
                85                  90                  95

Leu Phe Leu Asn Trp Thr Glu Gly Gln Lys Ser Gly Phe Leu Arg Ile
            100                 105                 110

Ser Asn Leu Gln Lys Gln Asp Gln Ser Val Tyr Phe Cys Arg Val Glu
        115                 120                 125

Leu Asp Thr Arg Ser Ser Gly Arg Gln Gln Trp Gln Ser Ile Glu Gly
130                 135                 140

Thr Lys Leu Ser Ile Thr Gln Ala Val Thr Thr Thr Gln Arg Pro
145                 150                 155                 160

Ser Ser Met Thr Thr Thr Trp Arg Leu Ser Thr Thr Thr Thr Thr
                165                 170                 175

Gly Leu Arg Val Thr Gln Gly Lys Arg Arg Ser Asp Ser Trp His Ile
            180                 185                 190

Ser Leu Glu Thr Ala Val Gly Val Ala Val Ala Val Thr Val Leu Gly
        195                 200                 205

Ile Met Ile Leu Gly Leu Ile Cys Leu Leu Arg Trp Arg Arg Arg Lys
210                 215                 220

Gly Gln Gln Arg Thr Lys Ala Thr Thr Pro Ala Arg Glu Pro Phe Gln
225                 230                 235                 240

Asn Thr Glu Glu Pro Tyr Glu Asn Ile Arg Asn Glu Gly Gln Asn Thr
                245                 250                 255

Asp Pro Lys Leu Asn Pro Lys Asp Asp Gly Ile Val Tyr Ala Ser Leu
            260                 265                 270

Ala Leu Ser Ser Ser Thr Ser Pro Arg Ala Pro Pro Ser His Arg Pro
        275                 280                 285

Leu Lys Ser Pro Gln Asn Glu Thr Leu Tyr Ser Val Leu Lys Ala
290                 295                 300

<210> SEQ ID NO 4
<211> LENGTH: 284
<212> TYPE: PRT
<213> ORGANISM: Homo sapiens

<400> SEQUENCE: 4

Gln Pro Ser Gly Ser Thr Gly Ser Gly Pro Ser Tyr Leu Tyr Gly Val
1               5                   10                  15

Thr Gln Pro Lys His Leu Ser Ala Ser Met Gly Gly Ser Val Glu Ile
            20                  25                  30
```

```
Pro Phe Ser Phe Tyr Tyr Pro Trp Glu Leu Ala Thr Ala Pro Asp Val
            35                  40                  45

Arg Ile Ser Trp Arg Arg Gly His Phe His Arg Gln Ser Phe Tyr Ser
 50                  55                  60

Thr Arg Pro Pro Ser Ile His Lys Asp Tyr Val Asn Arg Leu Phe Leu
 65                  70                  75                  80

Asn Trp Thr Glu Gly Gln Lys Ser Gly Phe Leu Arg Ile Ser Asn Leu
                85                  90                  95

Gln Lys Gln Asp Gln Ser Val Tyr Phe Cys Arg Val Glu Leu Asp Thr
            100                 105                 110

Arg Ser Ser Gly Arg Gln Gln Trp Gln Ser Ile Glu Gly Thr Lys Leu
            115                 120                 125

Ser Ile Thr Gln Ala Val Thr Thr Thr Gln Arg Pro Ser Ser Met
            130                 135                 140

Thr Thr Thr Trp Arg Leu Ser Ser Thr Thr Thr Thr Gly Leu Arg
145                 150                 155                 160

Val Thr Gln Gly Lys Arg Ser Asp Ser Trp His Ile Ser Leu Glu
                165                 170                 175

Thr Ala Val Gly Val Ala Val Ala Val Thr Val Leu Gly Ile Met Ile
            180                 185                 190

Leu Gly Leu Ile Cys Leu Leu Arg Trp Arg Arg Lys Gly Gln Gln
            195                 200                 205

Arg Thr Lys Ala Thr Thr Pro Ala Arg Glu Pro Phe Gln Asn Thr Glu
            210                 215                 220

Glu Pro Tyr Glu Asn Ile Arg Asn Glu Gly Gln Asn Thr Asp Pro Lys
225                 230                 235                 240

Leu Asn Pro Lys Asp Asp Gly Ile Val Tyr Ala Ser Leu Ala Leu Ser
                245                 250                 255

Ser Ser Thr Ser Pro Arg Ala Pro Pro Ser His Arg Pro Leu Lys Ser
            260                 265                 270

Pro Gln Asn Glu Thr Leu Tyr Ser Val Leu Lys Ala
            275                 280

<210> SEQ ID NO 5
<211> LENGTH: 325
<212> TYPE: PRT
<213> ORGANISM: Homo sapiens

<400> SEQUENCE: 5

Met Ala Thr Pro Leu Pro Pro Ser Pro Arg His Leu Arg Leu Leu
 1               5                  10                  15

Arg Leu Leu Leu Ser Gly Leu Val Leu Gly Ala Ala Leu Arg Gly Ala
                20                  25                  30

Ala Ala Gly His Pro Asp Val Ala Cys Pro Gly Ser Leu Asp Cys
            35                  40                  45

Ala Leu Lys Arg Arg Ala Arg Cys Pro Pro Gly Ala His Ala Cys Gly
            50                  55                  60

Pro Cys Leu Gln Pro Phe Gln Glu Asp Gln Gly Leu Cys Val Pro
 65                  70                  75                  80

Arg Met Arg Arg Pro Gly Gly Gly Arg Pro Gln Pro Arg Leu Glu
                85                  90                  95

Asp Glu Ile Asp Phe Leu Ala Gln Glu Leu Ala Arg Lys Glu Ser Gly
            100                 105                 110

Gln Ser Thr Pro Pro Leu Pro Lys Asp Arg Gln Arg Leu Pro Glu Pro
            115                 120                 125
```

```
Ala Thr Leu Gly Phe Ser Ala Arg Gly Gln Gly Leu Glu Leu Gly Leu
    130                 135                 140

Pro Ser Thr Pro Gly Thr Pro Thr Pro Thr Pro His Thr Ser Leu Gly
145                 150                 155                 160

Ser Pro Val Ser Ser Asp Pro Val His Met Ser Pro Leu Glu Pro Arg
                165                 170                 175

Gly Gly Gln Gly Asp Gly Leu Ala Leu Val Leu Ile Leu Ala Phe Cys
            180                 185                 190

Val Ala Gly Ala Ala Leu Ser Val Ala Ser Leu Cys Trp Cys Arg
        195                 200                 205

Leu Gln Arg Glu Ile Arg Leu Thr Gln Lys Ala Asp Tyr Ala Thr Ala
    210                 215                 220

Lys Ala Pro Gly Ser Pro Ala Ala Pro Arg Ile Ser Pro Gly Asp Gln
225                 230                 235                 240

Arg Leu Ala Gln Ser Ala Glu Met Tyr His Tyr Gln His Gln Arg Gln
                245                 250                 255

Gln Met Leu Cys Leu Glu Arg His Lys Glu Pro Pro Lys Glu Leu Asp
            260                 265                 270

Thr Ala Ser Ser Asp Glu Glu Asn Glu Asp Gly Asp Phe Thr Val Tyr
        275                 280                 285

Glu Cys Pro Gly Leu Ala Pro Thr Gly Glu Met Glu Val Arg Asn Pro
290                 295                 300

Leu Phe Asp His Ala Ala Leu Ser Ala Pro Leu Pro Ala Pro Ser Ser
305                 310                 315                 320

Pro Pro Ala Leu Pro
                325

<210> SEQ ID NO 6
<211> LENGTH: 291
<212> TYPE: PRT
<213> ORGANISM: Homo sapiens

<400> SEQUENCE: 6

Gly His Pro Asp Val Ala Ala Cys Pro Gly Ser Leu Asp Cys Ala Leu
1               5                   10                  15

Lys Arg Arg Ala Arg Cys Pro Pro Gly Ala His Ala Cys Gly Pro Cys
                20                  25                  30

Leu Gln Pro Phe Gln Glu Asp Gln Gln Gly Leu Cys Val Pro Arg Met
            35                  40                  45

Arg Arg Pro Pro Gly Gly Gly Arg Pro Gln Pro Arg Leu Glu Asp Glu
        50                  55                  60

Ile Asp Phe Leu Ala Gln Glu Leu Ala Arg Lys Glu Ser Gly Gln Ser
65                  70                  75                  80

Thr Pro Pro Leu Pro Lys Asp Arg Gln Arg Leu Pro Glu Pro Ala Thr
                85                  90                  95

Leu Gly Phe Ser Ala Arg Gly Gln Gly Leu Glu Leu Gly Leu Pro Ser
            100                 105                 110

Thr Pro Gly Thr Pro Thr Pro Thr Pro His Thr Ser Leu Gly Ser Pro
        115                 120                 125

Val Ser Ser Asp Pro Val His Met Ser Pro Leu Glu Pro Arg Gly Gly
130                 135                 140

Gln Gly Asp Gly Leu Ala Leu Val Leu Ile Leu Ala Phe Cys Val Ala
145                 150                 155                 160

Gly Ala Ala Ala Leu Ser Val Ala Ser Leu Cys Trp Cys Arg Leu Gln
                165                 170                 175
```

```
Arg Glu Ile Arg Leu Thr Gln Lys Ala Asp Tyr Ala Thr Ala Lys Ala
            180                 185                 190

Pro Gly Ser Pro Ala Ala Pro Arg Ile Ser Pro Gly Asp Gln Arg Leu
            195                 200                 205

Ala Gln Ser Ala Glu Met Tyr His Tyr Gln His Gln Arg Gln Gln Met
210                 215                 220

Leu Cys Leu Glu Arg His Lys Glu Pro Pro Lys Glu Leu Asp Thr Ala
225                 230                 235                 240

Ser Ser Asp Glu Glu Asn Glu Asp Gly Asp Phe Thr Val Tyr Glu Cys
                245                 250                 255

Pro Gly Leu Ala Pro Thr Gly Glu Met Glu Val Arg Asn Pro Leu Phe
            260                 265                 270

Asp His Ala Ala Leu Ser Ala Pro Leu Pro Ala Pro Ser Ser Pro Pro
            275                 280                 285

Ala Leu Pro
    290

<210> SEQ ID NO 7
<211> LENGTH: 742
<212> TYPE: PRT
<213> ORGANISM: Homo sapiens

<400> SEQUENCE: 7

Met Lys Asp Asp Phe Ala Glu Glu Glu Val Gln Ser Phe Gly Tyr
1               5                   10                  15

Lys Arg Phe Gly Ile Gln Glu Gly Thr Gln Cys Thr Lys Cys Lys Asn
            20                  25                  30

Asn Trp Ala Leu Lys Phe Ser Ile Ile Leu Leu Tyr Ile Leu Cys Ala
        35                  40                  45

Leu Leu Thr Ile Thr Val Ala Ile Leu Gly Tyr Lys Val Val Glu Lys
    50                  55                  60

Met Asp Asn Val Thr Gly Gly Met Glu Thr Ser Arg Gln Thr Tyr Asp
65              70                  75                  80

Asp Lys Leu Thr Ala Val Glu Ser Asp Leu Lys Lys Leu Gly Asp Gln
                85                  90                  95

Thr Gly Lys Lys Ala Ile Ser Thr Asn Ser Glu Leu Ser Thr Phe Arg
            100                 105                 110

Ser Asp Ile Leu Asp Leu Arg Gln Gln Leu Arg Glu Ile Thr Glu Lys
        115                 120                 125

Thr Ser Lys Asn Lys Asp Thr Leu Glu Lys Leu Gln Ala Ser Gly Asp
    130                 135                 140

Ala Leu Val Asp Arg Gln Ser Gln Leu Lys Glu Thr Leu Glu Asn Asn
145                 150                 155                 160

Ser Phe Leu Ile Thr Thr Val Asn Lys Thr Leu Gln Ala Tyr Asn Gly
                165                 170                 175

Tyr Val Thr Asn Leu Gln Gln Asp Thr Ser Val Leu Gln Gly Asn Leu
            180                 185                 190

Gln Asn Gln Met Tyr Ser His Asn Val Val Ile Met Asn Leu Asn Asn
        195                 200                 205

Leu Asn Leu Thr Gln Val Gln Gln Arg Asn Leu Ile Thr Asn Leu Gln
    210                 215                 220

Arg Ser Val Asp Asp Thr Ser Gln Ala Ile Gln Arg Ile Lys Asn Asp
225                 230                 235                 240

Phe Gln Asn Leu Gln Gln Val Phe Leu Gln Ala Lys Lys Asp Thr Asp
                245                 250                 255
```

-continued

Trp Leu Lys Glu Lys Val Gln Ser Leu Gln Thr Leu Ala Ala Asn Asn
            260                 265                 270

Ser Ala Leu Ala Lys Ala Asn Asn Asp Thr Leu Glu Asp Met Asn Ser
    275                 280                 285

Gln Leu Asn Ser Phe Thr Gly Gln Met Glu Asn Ile Thr Thr Ile Ser
    290                 295                 300

Gln Ala Asn Glu Gln Asn Leu Lys Asp Leu Gln Asp Leu His Lys Asp
305                 310                 315                 320

Ala Glu Asn Arg Thr Ala Ile Lys Phe Asn Gln Leu Glu Glu Arg Phe
                325                 330                 335

Gln Leu Phe Glu Thr Asp Ile Val Asn Ile Ile Ser Asn Ile Ser Tyr
            340                 345                 350

Thr Ala His His Leu Arg Thr Leu Thr Ser Asn Leu Asn Glu Val Arg
            355                 360                 365

Thr Thr Cys Thr Asp Thr Leu Thr Lys His Thr Asp Asp Leu Thr Ser
            370                 375                 380

Leu Asn Asn Thr Leu Ala Asn Ile Arg Leu Asp Ser Val Ser Leu Arg
385                 390                 395                 400

Met Gln Gln Asp Leu Met Arg Ser Arg Leu Asp Thr Glu Val Ala Asn
                405                 410                 415

Leu Ser Val Ile Met Glu Met Lys Leu Val Asp Ser Lys His Gly
            420                 425                 430

Gln Leu Ile Lys Asn Phe Thr Ile Leu Gln Gly Pro Pro Gly Pro Arg
            435                 440                 445

Gly Pro Arg Gly Asp Arg Gly Ser Gln Gly Pro Pro Gly Pro Thr Gly
            450                 455                 460

Asn Lys Gly Gln Lys Gly Glu Lys Gly Glu Pro Gly Pro Pro Gly Pro
465                 470                 475                 480

Ala Gly Glu Arg Gly Pro Ile Gly Pro Ala Gly Pro Pro Gly Glu Arg
                485                 490                 495

Gly Gly Lys Gly Ser Lys Gly Ser Gln Gly Pro Lys Gly Ser Arg Gly
            500                 505                 510

Ser Pro Gly Lys Pro Gly Pro Gln Gly Pro Ser Gly Asp Pro Gly Pro
            515                 520                 525

Pro Gly Pro Pro Gly Lys Glu Gly Leu Pro Gly Pro Gln Gly Pro Pro
            530                 535                 540

Gly Phe Gln Gly Leu Gln Gly Thr Val Gly Glu Pro Gly Val Pro Gly
545                 550                 555                 560

Pro Arg Gly Leu Pro Gly Leu Pro Gly Val Pro Gly Met Pro Gly Pro
                565                 570                 575

Lys Gly Pro Pro Gly Pro Pro Gly Pro Ser Gly Ala Val Val Pro Leu
            580                 585                 590

Ala Leu Gln Asn Glu Pro Thr Pro Ala Pro Glu Asp Asn Ser Cys Pro
            595                 600                 605

Pro His Trp Lys Asn Phe Thr Asp Lys Cys Tyr Tyr Phe Ser Val Glu
            610                 615                 620

Lys Glu Ile Phe Glu Asp Ala Lys Leu Phe Cys Glu Asp Lys Ser Ser
625                 630                 635                 640

His Leu Val Phe Ile Asn Thr Arg Glu Glu Gln Gln Trp Ile Lys Lys
                645                 650                 655

Gln Met Val Gly Arg Glu Ser His Trp Ile Gly Leu Thr Asp Ser Glu
            660                 665                 670

-continued

```
Arg Glu Asn Glu Trp Lys Trp Leu Asp Gly Thr Ser Pro Asp Tyr Lys
            675                 680                 685

Asn Trp Lys Ala Gly Gln Pro Asp Asn Trp His Gly His Gly Pro
    690                 695                 700

Gly Glu Asp Cys Ala Gly Leu Ile Tyr Ala Gly Gln Trp Asn Asp Phe
705                 710                 715                 720

Gln Cys Glu Asp Val Asn Asn Phe Ile Cys Glu Lys Asp Arg Glu Thr
                725                 730                 735

Val Leu Ser Ser Ala Leu
            740

<210> SEQ ID NO 8
<211> LENGTH: 442
<212> TYPE: PRT
<213> ORGANISM: Homo sapiens

<400> SEQUENCE: 8

Met Gln Pro Pro Pro Ser Leu Cys Gly Arg Ala Leu Val Ala Leu Val
1               5                   10                  15

Leu Ala Cys Gly Leu Ser Arg Ile Trp Gly Glu Glu Arg Gly Phe Pro
            20                  25                  30

Pro Asp Arg Ala Thr Pro Leu Leu Gln Thr Ala Glu Ile Met Thr Pro
        35                  40                  45

Pro Thr Lys Thr Leu Trp Pro Lys Gly Ser Asn Ala Ser Leu Ala Arg
    50                  55                  60

Ser Leu Ala Pro Ala Glu Val Pro Lys Gly Asp Arg Thr Ala Gly Ser
65                  70                  75                  80

Pro Pro Arg Thr Ile Ser Pro Pro Cys Gln Gly Pro Ile Glu Ile
                85                  90                  95

Lys Glu Thr Phe Lys Tyr Ile Asn Thr Val Val Ser Cys Leu Val Phe
            100                 105                 110

Val Leu Gly Ile Ile Gly Asn Ser Thr Leu Leu Arg Ile Ile Tyr Lys
            115                 120                 125

Asn Lys Cys Met Arg Asn Gly Pro Asn Ile Leu Ile Ala Ser Leu Ala
    130                 135                 140

Leu Gly Asp Leu Leu His Ile Val Ile Asp Ile Pro Ile Asn Val Tyr
145                 150                 155                 160

Lys Leu Leu Ala Glu Asp Trp Pro Phe Gly Ala Glu Met Cys Lys Leu
                165                 170                 175

Val Pro Phe Ile Gln Lys Ala Ser Val Gly Ile Thr Val Leu Ser Leu
            180                 185                 190

Cys Ala Leu Ser Ile Asp Arg Tyr Arg Ala Val Ala Ser Trp Ser Arg
        195                 200                 205

Ile Lys Gly Ile Gly Val Pro Lys Trp Thr Ala Val Glu Ile Val Leu
    210                 215                 220

Ile Trp Val Val Ser Val Val Leu Ala Val Pro Glu Ala Ile Gly Phe
225                 230                 235                 240

Asp Ile Ile Thr Met Asp Tyr Lys Gly Ser Tyr Leu Arg Ile Cys Leu
                245                 250                 255

Leu His Pro Val Gln Lys Thr Ala Phe Met Gln Phe Tyr Lys Thr Ala
            260                 265                 270

Lys Asp Trp Trp Leu Phe Ser Phe Tyr Phe Cys Leu Pro Leu Ala Ile
        275                 280                 285

Thr Ala Phe Phe Tyr Thr Leu Met Thr Cys Glu Met Leu Arg Lys Lys
    290                 295                 300
```

```
Ser Gly Met Gln Ile Ala Leu Asn Asp His Leu Lys Gln Arg Arg Glu
305                 310                 315                 320

Val Ala Lys Thr Val Phe Cys Leu Val Leu Val Phe Ala Leu Cys Trp
                325                 330                 335

Leu Pro Leu His Leu Ser Arg Ile Leu Lys Leu Thr Leu Tyr Asn Gln
                340                 345                 350

Asn Asp Pro Asn Arg Cys Glu Leu Leu Ser Phe Leu Leu Val Leu Asp
            355                 360                 365

Tyr Ile Gly Ile Asn Met Ala Ser Leu Asn Ser Cys Ile Asn Pro Ile
370                 375                 380

Ala Leu Tyr Leu Val Ser Lys Arg Phe Lys Asn Cys Phe Lys Ser Cys
385                 390                 395                 400

Leu Cys Cys Trp Cys Gln Ser Phe Glu Glu Lys Gln Ser Leu Glu Glu
                405                 410                 415

Lys Gln Ser Cys Leu Lys Phe Lys Ala Asn Asp His Gly Tyr Asp Asn
                420                 425                 430

Phe Arg Ser Ser Asn Lys Tyr Ser Ser Ser
            435                 440

<210> SEQ ID NO 9
<211> LENGTH: 416
<212> TYPE: PRT
<213> ORGANISM: Homo sapiens

<400> SEQUENCE: 9

Glu Glu Arg Gly Phe Pro Pro Asp Arg Ala Thr Pro Leu Leu Gln Thr
1               5                   10                  15

Ala Glu Ile Met Thr Pro Pro Thr Lys Thr Leu Trp Pro Lys Gly Ser
                20                  25                  30

Asn Ala Ser Leu Ala Arg Ser Leu Ala Pro Ala Glu Val Pro Lys Gly
            35                  40                  45

Asp Arg Thr Ala Gly Ser Pro Pro Arg Thr Ile Ser Pro Pro Pro Cys
        50                  55                  60

Gln Gly Pro Ile Glu Ile Lys Glu Thr Phe Lys Tyr Ile Asn Thr Val
65                  70                  75                  80

Val Ser Cys Leu Val Phe Val Leu Gly Ile Ile Gly Asn Ser Thr Leu
                85                  90                  95

Leu Arg Ile Ile Tyr Lys Asn Lys Cys Met Arg Asn Gly Pro Asn Ile
                100                 105                 110

Leu Ile Ala Ser Leu Ala Leu Gly Asp Leu Leu His Ile Val Ile Asp
            115                 120                 125

Ile Pro Ile Asn Val Tyr Lys Leu Leu Ala Glu Asp Trp Pro Phe Gly
        130                 135                 140

Ala Glu Met Cys Lys Leu Val Pro Phe Ile Gln Lys Ala Ser Val Gly
145                 150                 155                 160

Ile Thr Val Leu Ser Leu Cys Ala Leu Ser Ile Asp Arg Tyr Arg Ala
                165                 170                 175

Val Ala Ser Trp Ser Arg Ile Lys Gly Ile Gly Val Pro Lys Trp Thr
                180                 185                 190

Ala Val Glu Ile Val Leu Ile Trp Val Val Ser Val Val Leu Ala Val
            195                 200                 205

Pro Glu Ala Ile Gly Phe Asp Ile Ile Thr Met Asp Tyr Lys Gly Ser
        210                 215                 220

Tyr Leu Arg Ile Cys Leu Leu His Pro Val Gln Lys Thr Ala Phe Met
225                 230                 235                 240
```

```
Gln Phe Tyr Lys Thr Ala Lys Asp Trp Trp Leu Phe Ser Phe Tyr Phe
                245                 250                 255

Cys Leu Pro Leu Ala Ile Thr Ala Phe Phe Tyr Thr Leu Met Thr Cys
            260                 265                 270

Glu Met Leu Arg Lys Lys Ser Gly Met Gln Ile Ala Leu Asn Asp His
        275                 280                 285

Leu Lys Gln Arg Arg Glu Val Ala Lys Thr Val Phe Cys Leu Val Leu
    290                 295                 300

Val Phe Ala Leu Cys Trp Leu Pro Leu His Leu Ser Arg Ile Leu Lys
305                 310                 315                 320

Leu Thr Leu Tyr Asn Gln Asn Asp Pro Asn Arg Cys Glu Leu Leu Ser
                325                 330                 335

Phe Leu Leu Val Leu Asp Tyr Ile Gly Ile Asn Met Ala Ser Leu Asn
            340                 345                 350

Ser Cys Ile Asn Pro Ile Ala Leu Tyr Leu Val Ser Lys Arg Phe Lys
        355                 360                 365

Asn Cys Phe Lys Ser Cys Leu Cys Cys Trp Cys Gln Ser Phe Glu Glu
    370                 375                 380

Lys Gln Ser Leu Glu Glu Lys Gln Ser Cys Leu Lys Phe Lys Ala Asn
385                 390                 395                 400

Asp His Gly Tyr Asp Asn Phe Arg Ser Ser Asn Lys Tyr Ser Ser Ser
                405                 410                 415

<210> SEQ ID NO 10
<211> LENGTH: 293
<212> TYPE: PRT
<213> ORGANISM: Homo sapiens

<400> SEQUENCE: 10

Met Asp Thr Thr Arg Tyr Ser Lys Trp Gly Ser Ser Glu Glu Val
1               5                   10                  15

Pro Gly Gly Pro Trp Gly Arg Trp Val His Trp Ser Arg Arg Pro Leu
                20                  25                  30

Phe Leu Ala Leu Ala Val Leu Val Thr Thr Val Leu Trp Ala Val Ile
            35                  40                  45

Leu Ser Ile Leu Leu Ser Lys Ala Ser Thr Glu Arg Ala Ala Leu Leu
    50                  55                  60

Asp Gly His Asp Leu Leu Arg Thr Asn Ala Ser Lys Gln Thr Ala Ala
65                  70                  75                  80

Leu Gly Ala Leu Lys Glu Glu Val Gly Asp Cys His Ser Cys Cys Ser
                85                  90                  95

Gly Thr Gln Ala Gln Leu Gln Thr Thr Arg Ala Glu Leu Gly Glu Ala
            100                 105                 110

Gln Ala Lys Leu Met Glu Gln Glu Ser Ala Leu Arg Glu Leu Arg Glu
    115                 120                 125

Arg Val Thr Gln Gly Leu Ala Glu Ala Gly Arg Gly Arg Glu Asp Val
130                 135                 140

Arg Thr Glu Leu Phe Arg Ala Leu Glu Ala Val Arg Leu Gln Asn Asn
145                 150                 155                 160

Ser Cys Glu Pro Cys Pro Thr Ser Trp Leu Ser Phe Glu Gly Ser Cys
                165                 170                 175

Tyr Phe Phe Ser Val Pro Lys Thr Thr Trp Ala Ala Ala Gln Asp His
            180                 185                 190

Cys Ala Asp Ala Ser Ala His Leu Val Ile Val Gly Gly Leu Asp Glu
    195                 200                 205
```

```
Gln Gly Phe Leu Thr Arg Asn Thr Arg Gly Arg Gly Tyr Trp Leu Gly
    210                 215                 220
Leu Arg Ala Val Arg His Leu Gly Lys Val Gln Gly Tyr Gln Trp Val
225                 230                 235                 240
Asp Gly Val Ser Leu Ser Phe Ser His Trp Asn Gln Gly Glu Pro Asn
                245                 250                 255
Asp Ala Trp Gly Arg Glu Asn Cys Val Met Met Leu His Thr Gly Leu
                260                 265                 270
Trp Asn Asp Ala Pro Cys Asp Ser Glu Lys Asp Gly Trp Ile Cys Glu
                275                 280                 285
Lys Arg His Asn Cys
        290

<210> SEQ ID NO 11
<211> LENGTH: 247
<212> TYPE: PRT
<213> ORGANISM: Homo sapiens

<400> SEQUENCE: 11

Val Ile Leu Ser Ile Leu Leu Ser Lys Ala Ser Thr Glu Arg Ala Ala
1               5                   10                  15
Leu Leu Asp Gly His Asp Leu Leu Arg Thr Asn Ala Ser Lys Gln Thr
                20                  25                  30
Ala Ala Leu Gly Ala Leu Lys Glu Val Gly Asp Cys His Ser Cys
            35                  40                  45
Cys Ser Gly Thr Gln Ala Gln Leu Gln Thr Thr Arg Ala Glu Leu Gly
        50                  55                  60
Glu Ala Gln Ala Lys Leu Met Glu Gln Glu Ser Ala Leu Arg Glu Leu
65                  70                  75                  80
Arg Glu Arg Val Thr Gln Gly Leu Ala Glu Ala Gly Arg Gly Arg Glu
                85                  90                  95
Asp Val Arg Thr Glu Leu Phe Arg Ala Leu Glu Ala Val Arg Leu Gln
                100                 105                 110
Asn Asn Ser Cys Glu Pro Cys Pro Thr Ser Trp Leu Ser Phe Glu Gly
            115                 120                 125
Ser Cys Tyr Phe Phe Ser Val Pro Lys Thr Thr Trp Ala Ala Ala Gln
        130                 135                 140
Asp His Cys Ala Asp Ala Ser Ala His Leu Val Ile Val Gly Gly Leu
145                 150                 155                 160
Asp Glu Gln Gly Phe Leu Thr Arg Asn Thr Arg Gly Arg Gly Tyr Trp
                165                 170                 175
Leu Gly Leu Arg Ala Val Arg His Leu Gly Lys Val Gln Gly Tyr Gln
                180                 185                 190
Trp Val Asp Gly Val Ser Leu Ser Phe Ser His Trp Asn Gln Gly Glu
                195                 200                 205
Pro Asn Asp Ala Trp Gly Arg Glu Asn Cys Val Met Met Leu His Thr
            210                 215                 220
Gly Leu Trp Asn Asp Ala Pro Cys Asp Ser Glu Lys Asp Gly Trp Ile
225                 230                 235                 240
Cys Glu Lys Arg His Asn Cys
                245

<210> SEQ ID NO 12
<211> LENGTH: 184
<212> TYPE: PRT
<213> ORGANISM: Homo sapiens
```

<400> SEQUENCE: 12

```
Met Arg Arg Gly Pro Arg Ser Leu Arg Gly Arg Asp Ala Pro Ala Pro
1               5                   10                  15
Thr Pro Cys Val Pro Ala Glu Cys Phe Asp Leu Leu Val Arg His Cys
            20                  25                  30
Val Ala Cys Gly Leu Leu Arg Thr Pro Arg Pro Lys Pro Ala Gly Ala
        35                  40                  45
Ser Ser Pro Ala Pro Arg Thr Ala Leu Gln Pro Gln Glu Ser Val Gly
    50                  55                  60
Ala Gly Ala Gly Glu Ala Ala Leu Pro Leu Pro Gly Leu Leu Phe Gly
65                  70                  75                  80
Ala Pro Ala Leu Leu Gly Leu Ala Leu Val Leu Ala Leu Val Leu Val
                85                  90                  95
Gly Leu Val Ser Trp Arg Arg Arg Gln Arg Arg Leu Arg Gly Ala Ser
            100                 105                 110
Ser Ala Glu Ala Pro Asp Gly Asp Lys Asp Ala Pro Glu Pro Leu Asp
        115                 120                 125
Lys Val Ile Ile Leu Ser Pro Gly Ile Ser Asp Ala Thr Ala Pro Ala
    130                 135                 140
Trp Pro Pro Pro Gly Glu Asp Pro Gly Thr Thr Pro Pro Gly His Ser
145                 150                 155                 160
Val Pro Val Pro Ala Thr Glu Leu Gly Ser Thr Glu Leu Val Thr Thr
                165                 170                 175
Lys Thr Ala Gly Pro Glu Gln Gln
            180
```

<210> SEQ ID NO 13
<211> LENGTH: 626
<212> TYPE: PRT
<213> ORGANISM: Homo sapiens

<400> SEQUENCE: 13

```
Met Ile Phe Leu Thr Ala Leu Pro Leu Phe Trp Ile Met Ile Ser Ala
1               5                   10                  15
Ser Arg Gly Gly His Trp Gly Ala Trp Met Pro Ser Ser Ile Ser Ala
            20                  25                  30
Phe Glu Gly Thr Cys Val Ser Ile Pro Cys Arg Phe Asp Phe Pro Asp
        35                  40                  45
Glu Leu Arg Pro Ala Val Val His Gly Val Trp Tyr Phe Asn Ser Pro
    50                  55                  60
Tyr Pro Lys Asn Tyr Pro Pro Val Val Phe Lys Ser Arg Thr Gln Val
65                  70                  75                  80
Val His Glu Ser Phe Gln Gly Arg Ser Arg Leu Leu Gly Asp Leu Gly
                85                  90                  95
Leu Arg Asn Cys Thr Leu Leu Leu Ser Asn Val Ser Pro Glu Leu Gly
            100                 105                 110
Gly Lys Tyr Tyr Phe Arg Gly Asp Leu Gly Gly Tyr Asn Gln Tyr Thr
        115                 120                 125
Phe Ser Glu His Ser Val Leu Asp Ile Val Asn Thr Pro Asn Ile Val
    130                 135                 140
Val Pro Pro Glu Val Val Ala Gly Thr Glu Val Glu Val Ser Cys Met
145                 150                 155                 160
Val Pro Asp Asn Cys Pro Glu Leu Arg Pro Glu Leu Ser Trp Leu Gly
                165                 170                 175
```

-continued

His Glu Gly Leu Gly Glu Pro Ala Val Leu Gly Arg Leu Arg Glu Asp
                180                 185                 190

Glu Gly Thr Trp Val Gln Val Ser Leu Leu His Phe Val Pro Thr Arg
            195                 200                 205

Glu Ala Asn Gly His Arg Leu Gly Cys Gln Ala Ser Phe Pro Asn Thr
        210                 215                 220

Thr Leu Gln Phe Glu Gly Tyr Ala Ser Met Asp Val Lys Tyr Pro Pro
225                 230                 235                 240

Val Ile Val Glu Met Asn Ser Ser Val Glu Ala Ile Glu Gly Ser His
                245                 250                 255

Val Ser Leu Leu Cys Gly Ala Asp Ser Asn Pro Pro Pro Leu Leu Thr
            260                 265                 270

Trp Met Arg Asp Gly Thr Val Leu Arg Glu Ala Val Ala Glu Ser Leu
        275                 280                 285

Leu Leu Glu Leu Glu Glu Val Thr Pro Ala Glu Asp Gly Val Tyr Ala
290                 295                 300

Cys Leu Ala Glu Asn Ala Tyr Gly Gln Asp Asn Arg Thr Val Gly Leu
305                 310                 315                 320

Ser Val Met Tyr Ala Pro Trp Lys Pro Thr Val Asn Gly Thr Met Val
            325                 330                 335

Ala Val Glu Gly Glu Thr Val Ser Ile Leu Cys Ser Thr Gln Ser Asn
        340                 345                 350

Pro Asp Pro Ile Leu Thr Ile Phe Lys Glu Lys Gln Ile Leu Ser Thr
    355                 360                 365

Val Ile Tyr Glu Ser Glu Leu Gln Leu Glu Leu Pro Ala Val Ser Pro
370                 375                 380

Glu Asp Asp Gly Glu Tyr Trp Cys Val Ala Glu Asn Gln Tyr Gly Gln
385                 390                 395                 400

Arg Ala Thr Ala Phe Asn Leu Ser Val Glu Phe Ala Pro Val Leu Leu
            405                 410                 415

Leu Glu Ser His Cys Ala Ala Ala Arg Asp Thr Val Gln Cys Leu Cys
        420                 425                 430

Val Val Lys Ser Asn Pro Glu Pro Ser Val Ala Phe Glu Leu Pro Ser
    435                 440                 445

Arg Asn Val Thr Val Asn Glu Ser Glu Arg Glu Phe Val Tyr Ser Glu
450                 455                 460

Arg Ser Gly Leu Val Leu Thr Ser Ile Leu Thr Leu Arg Gly Gln Ala
465                 470                 475                 480

Gln Ala Pro Pro Arg Val Ile Cys Thr Ala Arg Asn Leu Tyr Gly Ala
            485                 490                 495

Lys Ser Leu Glu Leu Pro Phe Gln Gly Ala His Arg Leu Met Trp Ala
        500                 505                 510

Lys Ile Gly Pro Val Gly Ala Val Val Ala Phe Ala Ile Leu Ile Ala
    515                 520                 525

Ile Val Cys Tyr Ile Thr Gln Thr Arg Arg Lys Lys Asn Val Thr Glu
530                 535                 540

Ser Pro Ser Phe Ser Ala Gly Asp Asn Pro Pro Val Leu Phe Ser Ser
545                 550                 555                 560

Asp Phe Arg Ile Ser Gly Ala Pro Glu Lys Tyr Glu Ser Glu Arg Arg
            565                 570                 575

Leu Gly Ser Glu Arg Arg Leu Leu Gly Leu Arg Gly Glu Pro Pro Glu
        580                 585                 590

```
Leu Asp Leu Ser Tyr Ser His Ser Asp Leu Gly Lys Arg Pro Thr Lys
            595                 600                 605

Asp Ser Tyr Thr Leu Thr Glu Glu Leu Ala Glu Tyr Ala Glu Ile Arg
610                 615                 620

Val Lys
625

<210> SEQ ID NO 14
<211> LENGTH: 607
<212> TYPE: PRT
<213> ORGANISM: Homo sapiens

<400> SEQUENCE: 14

Gly His Trp Gly Ala Trp Met Pro Ser Ser Ile Ser Ala Phe Glu Gly
1               5                   10                  15

Thr Cys Val Ser Ile Pro Cys Arg Phe Asp Phe Pro Asp Glu Leu Arg
            20                  25                  30

Pro Ala Val Val His Gly Val Trp Tyr Phe Asn Ser Pro Tyr Pro Lys
        35                  40                  45

Asn Tyr Pro Pro Val Val Phe Lys Ser Arg Thr Gln Val Val His Glu
    50                  55                  60

Ser Phe Gln Gly Arg Ser Arg Leu Leu Gly Asp Leu Gly Leu Arg Asn
65                  70                  75                  80

Cys Thr Leu Leu Leu Ser Asn Val Ser Pro Glu Leu Gly Gly Lys Tyr
                85                  90                  95

Tyr Phe Arg Gly Asp Leu Gly Gly Tyr Asn Gln Tyr Thr Phe Ser Glu
            100                 105                 110

His Ser Val Leu Asp Ile Val Asn Thr Pro Asn Ile Val Val Pro Pro
        115                 120                 125

Glu Val Val Ala Gly Thr Glu Val Glu Val Ser Cys Met Val Pro Asp
    130                 135                 140

Asn Cys Pro Glu Leu Arg Pro Glu Leu Ser Trp Leu Gly His Glu Gly
145                 150                 155                 160

Leu Gly Glu Pro Ala Val Leu Gly Arg Leu Arg Glu Asp Glu Gly Thr
                165                 170                 175

Trp Val Gln Val Ser Leu Leu His Phe Val Pro Thr Arg Glu Ala Asn
            180                 185                 190

Gly His Arg Leu Gly Cys Gln Ala Ser Phe Pro Asn Thr Thr Leu Gln
        195                 200                 205

Phe Glu Gly Tyr Ala Ser Met Asp Val Lys Tyr Pro Pro Val Ile Val
    210                 215                 220

Glu Met Asn Ser Ser Val Glu Ala Ile Glu Gly Ser His Val Ser Leu
225                 230                 235                 240

Leu Cys Gly Ala Asp Ser Asn Pro Pro Pro Leu Leu Thr Trp Met Arg
                245                 250                 255

Asp Gly Thr Val Leu Arg Glu Ala Val Ala Glu Ser Leu Leu Leu Glu
            260                 265                 270

Leu Glu Glu Val Thr Pro Ala Glu Asp Gly Val Tyr Ala Cys Leu Ala
        275                 280                 285

Glu Asn Ala Tyr Gly Gln Asp Asn Arg Thr Val Gly Leu Ser Val Met
    290                 295                 300

Tyr Ala Pro Trp Lys Pro Thr Val Asn Gly Thr Met Val Ala Val Glu
305                 310                 315                 320

Gly Glu Thr Val Ser Ile Leu Cys Ser Thr Gln Ser Asn Pro Asp Pro
                325                 330                 335
```

```
Ile Leu Thr Ile Phe Lys Glu Lys Gln Ile Leu Ser Thr Val Ile Tyr
            340                 345                 350

Glu Ser Glu Leu Gln Leu Glu Leu Pro Ala Val Ser Pro Glu Asp Asp
            355                 360                 365

Gly Glu Tyr Trp Cys Val Ala Glu Asn Gln Tyr Gly Gln Arg Ala Thr
            370                 375                 380

Ala Phe Asn Leu Ser Val Glu Phe Ala Pro Val Leu Leu Leu Glu Ser
385                 390                 395                 400

His Cys Ala Ala Ala Arg Asp Thr Val Gln Cys Leu Cys Val Val Lys
                405                 410                 415

Ser Asn Pro Glu Pro Ser Val Ala Phe Glu Leu Pro Ser Arg Asn Val
                420                 425                 430

Thr Val Asn Glu Ser Glu Arg Glu Phe Val Tyr Ser Glu Arg Ser Gly
                435                 440                 445

Leu Val Leu Thr Ser Ile Leu Thr Leu Arg Gly Gln Ala Gln Ala Pro
                450                 455                 460

Pro Arg Val Ile Cys Thr Ala Arg Asn Leu Tyr Gly Ala Lys Ser Leu
465                 470                 475                 480

Glu Leu Pro Phe Gln Gly Ala His Arg Leu Met Trp Ala Lys Ile Gly
                485                 490                 495

Pro Val Gly Ala Val Val Ala Phe Ala Ile Leu Ile Ala Ile Val Cys
                500                 505                 510

Tyr Ile Thr Gln Thr Arg Arg Lys Asn Val Thr Glu Ser Pro Ser
                515                 520                 525

Phe Ser Ala Gly Asp Asn Pro Pro Val Leu Phe Ser Ser Asp Phe Arg
530                 535                 540

Ile Ser Gly Ala Pro Glu Lys Tyr Glu Ser Glu Arg Arg Leu Gly Ser
545                 550                 555                 560

Glu Arg Arg Leu Leu Gly Leu Arg Gly Glu Pro Pro Glu Leu Asp Leu
                565                 570                 575

Ser Tyr Ser His Ser Asp Leu Gly Lys Arg Pro Thr Lys Asp Ser Tyr
                580                 585                 590

Thr Leu Thr Glu Glu Leu Ala Glu Tyr Ala Glu Ile Arg Val Lys
            595                 600                 605

<210> SEQ ID NO 15
<211> LENGTH: 272
<212> TYPE: PRT
<213> ORGANISM: Homo sapiens

<400> SEQUENCE: 15

Met Asp Ser Tyr Leu Leu Met Trp Gly Leu Leu Thr Phe Ile Met Val
1               5                   10                  15

Pro Gly Cys Gln Ala Glu Leu Cys Asp Asp Asp Pro Pro Glu Ile Pro
                20                  25                  30

His Ala Thr Phe Lys Ala Met Ala Tyr Lys Glu Gly Thr Met Leu Asn
            35                  40                  45

Cys Glu Cys Lys Arg Gly Phe Arg Arg Ile Lys Ser Gly Ser Leu Tyr
        50                  55                  60

Met Leu Cys Thr Gly Asn Ser Ser His Ser Ser Trp Asp Asn Gln Cys
65                  70                  75                  80

Gln Cys Thr Ser Ser Ala Thr Arg Asn Thr Thr Lys Gln Val Thr Pro
                85                  90                  95

Gln Pro Glu Glu Gln Lys Glu Arg Lys Thr Thr Glu Met Gln Ser Pro
                100                 105                 110
```

```
Met Gln Pro Val Asp Gln Ala Ser Leu Pro Gly His Cys Arg Glu Pro
            115                 120                 125

Pro Pro Trp Glu Asn Glu Ala Thr Glu Arg Ile Tyr His Phe Val Val
        130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
            180                 185                 190

Phe Pro Gly Glu Lys Pro Gln Ala Ser Pro Glu Gly Arg Pro Glu
        195                 200                 205

Ser Glu Thr Ser Cys Leu Val Thr Thr Thr Asp Phe Gln Ile Gln Thr
        210                 215                 220

Glu Met Ala Ala Thr Met Glu Thr Ser Ile Phe Thr Thr Glu Tyr Gln
225                 230                 235                 240

Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Arg Arg Thr Ile
            260                 265                 270

<210> SEQ ID NO 16
<211> LENGTH: 251
<212> TYPE: PRT
<213> ORGANISM: Homo sapiens

<400> SEQUENCE: 16

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
            180                 185                 190

Leu Val Thr Thr Thr Asp Phe Gln Ile Gln Thr Glu Met Ala Ala Thr
        195                 200                 205

Met Glu Thr Ser Ile Phe Thr Thr Glu Tyr Gln Val Ala Val Ala Gly
    210                 215                 220
```

```
Cys Val Phe Leu Leu Ile Ser Val Leu Leu Ser Gly Leu Thr Trp
225                 230                 235                 240

Gln Arg Arg Gln Arg Lys Ser Arg Arg Thr Ile
            245                 250
```

<210> SEQ ID NO 17
<211> LENGTH: 321
<212> TYPE: PRT
<213> ORGANISM: Homo sapiens

<400> SEQUENCE: 17

```
Met Glu Glu Gly Gln Tyr Ser Glu Ile Glu Glu Leu Pro Arg Arg Arg
1               5                   10                  15

Cys Cys Arg Arg Gly Thr Gln Ile Val Leu Leu Gly Leu Val Thr Ala
                20                  25                  30

Ala Leu Trp Ala Gly Leu Leu Thr Leu Leu Leu Trp His Trp Asp
            35                  40                  45

Thr Thr Gln Ser Leu Lys Gln Leu Glu Glu Arg Ala Ala Arg Asn Val
50                  55                  60

Ser Gln Val Ser Lys Asn Leu Glu Ser His His Gly Asp Gln Met Ala
65                  70                  75                  80

Gln Lys Ser Gln Ser Thr Gln Ile Ser Gln Glu Leu Glu Glu Leu Arg
                85                  90                  95

Ala Glu Gln Gln Arg Leu Lys Ser Gln Asp Leu Glu Leu Ser Trp Asn
            100                 105                 110

Leu Asn Gly Leu Gln Ala Asp Leu Ser Ser Phe Lys Ser Gln Glu Leu
        115                 120                 125

Asn Glu Arg Asn Glu Ala Ser Asp Leu Leu Glu Arg Leu Arg Glu Glu
130                 135                 140

Val Thr Lys Leu Arg Met Glu Leu Gln Val Ser Ser Gly Phe Val Cys
145                 150                 155                 160

Asn Thr Cys Pro Glu Lys Trp Ile Asn Phe Gln Arg Lys Cys Tyr Tyr
                165                 170                 175

Phe Gly Lys Gly Thr Lys Gln Trp Val His Ala Arg Tyr Ala Cys Asp
            180                 185                 190

Asp Met Glu Gly Gln Leu Val Ser Ile His Ser Pro Glu Glu Gln Asp
        195                 200                 205

Phe Leu Thr Lys His Ala Ser His Thr Gly Ser Trp Ile Gly Leu Arg
210                 215                 220

Asn Leu Asp Leu Lys Gly Glu Phe Ile Trp Val Asp Gly Ser His Val
225                 230                 235                 240

Asp Tyr Ser Asn Trp Ala Pro Gly Glu Pro Thr Ser Arg Ser Gln Gly
                245                 250                 255

Glu Asp Cys Val Met Met Arg Gly Ser Gly Arg Trp Thr Asp Ala Phe
            260                 265                 270

Cys Asp Arg Lys Leu Gly Ala Trp Val Cys Asp Arg Leu Ala Thr Cys
        275                 280                 285

Thr Pro Pro Ala Ser Glu Gly Ser Ala Glu Ser Met Gly Pro Asp Ser
290                 295                 300

Arg Pro Asp Pro Asp Gly Arg Leu Pro Thr Pro Ser Ala Pro Leu His
305                 310                 315                 320

Ser
```

<210> SEQ ID NO 18

<211> LENGTH: 590
<212> TYPE: PRT
<213> ORGANISM: Homo sapiens

<400> SEQUENCE: 18

```
Met Gly Phe His Leu Ile Thr Gln Leu Lys Gly Met Ser Val Val Leu
1               5                   10                  15

Val Leu Leu Pro Thr Leu Leu Val Met Leu Thr Gly Ala Gln Arg
                20                  25                  30

Ala Cys Pro Lys Asn Cys Arg Cys Asp Gly Lys Ile Val Tyr Cys Glu
            35                  40                  45

Ser His Ala Phe Ala Asp Ile Pro Glu Asn Ile Ser Gly Gly Ser Gln
    50                  55                  60

Gly Leu Ser Leu Arg Phe Asn Ser Ile Gln Lys Leu Lys Ser Asn Gln
65                  70                  75                  80

Phe Ala Gly Leu Asn Gln Leu Ile Trp Leu Tyr Leu Asp His Asn Tyr
                85                  90                  95

Ile Ser Ser Val Asp Glu Asp Ala Phe Gln Gly Ile Arg Arg Leu Lys
            100                 105                 110

Glu Leu Ile Leu Ser Ser Asn Lys Ile Thr Tyr Leu His Asn Lys Thr
        115                 120                 125

Phe His Pro Val Pro Asn Leu Arg Asn Leu Asp Leu Ser Tyr Asn Lys
    130                 135                 140

Leu Gln Thr Leu Gln Ser Glu Gln Phe Lys Gly Leu Arg Lys Leu Ile
145                 150                 155                 160

Ile Leu His Leu Arg Ser Asn Ser Leu Lys Thr Val Pro Ile Arg Val
                165                 170                 175

Phe Gln Asp Cys Arg Asn Leu Asp Phe Leu Asp Leu Gly Tyr Asn Arg
            180                 185                 190

Leu Arg Ser Leu Ser Arg Asn Ala Phe Ala Gly Leu Leu Lys Leu Lys
        195                 200                 205

Glu Leu His Leu Glu His Asn Gln Phe Ser Lys Ile Asn Phe Ala His
    210                 215                 220

Phe Pro Arg Leu Phe Asn Leu Arg Ser Ile Tyr Leu Gln Trp Asn Arg
225                 230                 235                 240

Ile Arg Ser Ile Ser Gln Gly Leu Thr Trp Thr Trp Ser Ser Leu His
                245                 250                 255

Asn Leu Asp Leu Ser Gly Asn Asp Ile Gln Gly Ile Glu Pro Gly Thr
            260                 265                 270

Phe Lys Cys Leu Pro Asn Leu Gln Lys Leu Asn Leu Asp Ser Asn Lys
        275                 280                 285

Leu Thr Asn Ile Ser Gln Glu Thr Val Asn Ala Trp Ile Ser Leu Ile
    290                 295                 300

Ser Ile Thr Leu Ser Gly Asn Met Trp Glu Cys Ser Arg Ser Ile Cys
305                 310                 315                 320

Pro Leu Phe Tyr Trp Leu Lys Asn Phe Lys Gly Asn Lys Glu Ser Thr
                325                 330                 335

Met Ile Cys Ala Gly Pro Lys His Ile Gln Gly Glu Lys Val Ser Asp
            340                 345                 350

Ala Val Glu Thr Tyr Asn Ile Cys Ser Glu Val Gln Val Asn Thr
        355                 360                 365

Glu Arg Ser His Leu Val Pro Gln Thr Pro Gln Lys Pro Leu Ile Ile
    370                 375                 380

Pro Arg Pro Thr Ile Phe Lys Pro Asp Val Thr Gln Ser Thr Phe Glu
```

```
            385                 390                 395                 400
        Thr Pro Ser Pro Ser Pro Gly Phe Gln Ile Pro Gly Ala Glu Gln Glu
                        405                 410                 415

Tyr Glu His Val Ser Phe His Lys Ile Ile Ala Gly Ser Val Ala Leu
                        420                 425                 430

Phe Leu Ser Val Ala Met Ile Leu Val Ile Tyr Val Ser Trp Lys
                        435                 440                 445

Arg Tyr Pro Ala Ser Met Lys Gln Leu Gln Gln His Ser Leu Met Lys
                        450                 455                 460

Arg Arg Arg Lys Lys Ala Arg Glu Ser Glu Arg Gln Met Asn Ser Pro
                        465                 470                 475                 480

Leu Gln Glu Tyr Tyr Val Asp Tyr Lys Pro Thr Asn Ser Glu Thr Met
                        485                 490                 495

Asp Ile Ser Val Asn Gly Ser Gly Pro Cys Thr Tyr Thr Ile Ser Gly
                        500                 505                 510

Ser Arg Glu Cys Glu Met Pro His His Met Lys Pro Leu Pro Tyr Tyr
                        515                 520                 525

Ser Tyr Asp Gln Pro Val Ile Gly Tyr Cys Gln Ala His Gln Pro Leu
                        530                 535                 540

His Val Thr Lys Gly Tyr Glu Thr Val Ser Pro Glu Gln Asp Glu Ser
        545                 550                 555                 560

Pro Gly Leu Glu Leu Gly Arg Asp His Ser Phe Ile Ala Thr Ile Ala
                        565                 570                 575

Arg Ser Ala Ala Pro Ala Ile Tyr Leu Glu Arg Ile Ala Asn
                        580                 585                 590

<210> SEQ ID NO 19
<211> LENGTH: 560
<212> TYPE: PRT
<213> ORGANISM: Homo sapiens

<400> SEQUENCE: 19

Gln Arg Ala Cys Pro Lys Asn Cys Arg Cys Asp Gly Lys Ile Val Tyr
        1               5                   10                  15

Cys Glu Ser His Ala Phe Ala Asp Ile Pro Glu Asn Ile Ser Gly Gly
                        20                  25                  30

Ser Gln Gly Leu Ser Leu Arg Phe Asn Ser Ile Gln Lys Leu Lys Ser
                        35                  40                  45

Asn Gln Phe Ala Gly Leu Asn Gln Leu Ile Trp Leu Tyr Leu Asp His
                50                  55                  60

Asn Tyr Ile Ser Ser Val Asp Glu Asp Ala Phe Gln Gly Ile Arg Arg
        65                  70                  75                  80

Leu Lys Glu Leu Ile Leu Ser Ser Asn Lys Ile Thr Tyr Leu His Asn
                        85                  90                  95

Lys Thr Phe His Pro Val Pro Asn Leu Arg Asn Leu Asp Leu Ser Tyr
                        100                 105                 110

Asn Lys Leu Gln Thr Leu Gln Ser Glu Gln Phe Lys Gly Leu Arg Lys
                        115                 120                 125

Leu Ile Ile Leu His Leu Arg Ser Asn Ser Leu Lys Thr Val Pro Ile
                        130                 135                 140

Arg Val Phe Gln Asp Cys Arg Asn Leu Asp Phe Leu Asp Leu Gly Tyr
        145                 150                 155                 160

Asn Arg Leu Arg Ser Leu Ser Arg Asn Ala Phe Ala Gly Leu Leu Lys
                        165                 170                 175
```

Leu Lys Glu Leu His Leu Glu His Asn Gln Phe Ser Lys Ile Asn Phe
            180                 185                 190

Ala His Phe Pro Arg Leu Phe Asn Leu Arg Ser Ile Tyr Leu Gln Trp
            195                 200                 205

Asn Arg Ile Arg Ser Ile Ser Gln Gly Leu Thr Trp Thr Trp Ser Ser
210                 215                 220

Leu His Asn Leu Asp Leu Ser Gly Asn Asp Ile Gln Gly Ile Glu Pro
225                 230                 235                 240

Gly Thr Phe Lys Cys Leu Pro Asn Leu Gln Lys Leu Asn Leu Asp Ser
                245                 250                 255

Asn Lys Leu Thr Asn Ile Ser Gln Glu Thr Val Asn Ala Trp Ile Ser
            260                 265                 270

Leu Ile Ser Ile Thr Leu Ser Gly Asn Met Trp Glu Cys Ser Arg Ser
        275                 280                 285

Ile Cys Pro Leu Phe Tyr Trp Leu Lys Asn Phe Lys Gly Asn Lys Glu
        290                 295                 300

Ser Thr Met Ile Cys Ala Gly Pro Lys His Ile Gln Gly Glu Lys Val
305                 310                 315                 320

Ser Asp Ala Val Glu Thr Tyr Asn Ile Cys Ser Glu Val Gln Val Val
                325                 330                 335

Asn Thr Glu Arg Ser His Leu Val Pro Gln Thr Pro Gln Lys Pro Leu
            340                 345                 350

Ile Ile Pro Arg Pro Thr Ile Phe Lys Pro Asp Val Thr Gln Ser Thr
        355                 360                 365

Phe Glu Thr Pro Ser Pro Ser Pro Gly Phe Gln Ile Pro Gly Ala Glu
370                 375                 380

Gln Glu Tyr Glu His Val Ser Phe His Lys Ile Ile Ala Gly Ser Val
385                 390                 395                 400

Ala Leu Phe Leu Ser Val Ala Met Ile Leu Leu Val Ile Tyr Val Ser
                405                 410                 415

Trp Lys Arg Tyr Pro Ala Ser Met Lys Gln Leu Gln Gln His Ser Leu
            420                 425                 430

Met Lys Arg Arg Arg Lys Lys Ala Arg Glu Ser Glu Arg Gln Met Asn
        435                 440                 445

Ser Pro Leu Gln Glu Tyr Tyr Val Asp Tyr Lys Pro Thr Asn Ser Glu
450                 455                 460

Thr Met Asp Ile Ser Val Asn Gly Ser Gly Pro Cys Thr Tyr Thr Ile
465                 470                 475                 480

Ser Gly Ser Arg Glu Cys Glu Met Pro His His Met Lys Pro Leu Pro
                485                 490                 495

Tyr Tyr Ser Tyr Asp Gln Pro Val Ile Gly Tyr Cys Gln Ala His Gln
            500                 505                 510

Pro Leu His Val Thr Lys Gly Tyr Glu Thr Val Ser Pro Glu Gln Asp
        515                 520                 525

Glu Ser Pro Gly Leu Glu Leu Gly Arg Asp His Ser Phe Ile Ala Thr
530                 535                 540

Ile Ala Arg Ser Ala Ala Pro Ala Ile Tyr Leu Glu Arg Ile Ala Asn
545                 550                 555                 560

<210> SEQ ID NO 20
<211> LENGTH: 895
<212> TYPE: PRT
<213> ORGANISM: Homo sapiens

<400> SEQUENCE: 20

```
Met Arg Met Ser Val Gly Leu Ser Leu Leu Pro Leu Trp Gly Arg
1               5                   10                  15

Thr Phe Leu Leu Leu Leu Ser Val Val Met Ala Gln Ser His Trp Pro
            20                  25                  30

Ser Glu Pro Ser Glu Ala Val Arg Asp Trp Glu Asn Gln Leu Glu Ala
            35                  40                  45

Ser Met His Ser Val Leu Ser Asp Leu His Glu Ala Val Pro Thr Val
        50                  55                  60

Val Gly Ile Pro Asp Gly Thr Ala Val Val Gly Arg Ser Phe Arg Val
65                  70                  75                  80

Thr Ile Pro Thr Asp Leu Ile Ala Ser Ser Gly Asp Ile Ile Lys Val
                85                  90                  95

Ser Ala Ala Gly Lys Glu Ala Leu Pro Ser Trp Leu His Trp Asp Ser
                100                 105                 110

Gln Ser His Thr Leu Glu Gly Leu Pro Leu Asp Thr Asp Lys Gly Val
            115                 120                 125

His Tyr Ile Ser Val Ser Ala Thr Arg Leu Gly Ala Asn Gly Ser His
        130                 135                 140

Ile Pro Gln Thr Ser Ser Val Phe Ser Ile Glu Val Tyr Pro Glu Asp
145                 150                 155                 160

His Ser Asp Leu Gln Ser Val Arg Thr Ala Ser Pro Asp Pro Gly Glu
                165                 170                 175

Val Val Ser Ser Ala Cys Ala Ala Asp Glu Pro Val Thr Val Leu Thr
                180                 185                 190

Val Ile Leu Asp Ala Asp Leu Thr Lys Met Thr Pro Lys Gln Arg Ile
                195                 200                 205

Asp Leu Leu His Arg Met Arg Ser Phe Ser Glu Val Glu Leu His Asn
210                 215                 220

Met Lys Leu Val Pro Val Val Asn Asn Arg Leu Phe Asp Met Ser Ala
225                 230                 235                 240

Phe Met Ala Gly Pro Gly Asn Pro Lys Lys Val Val Glu Asn Gly Ala
                245                 250                 255

Leu Leu Ser Trp Lys Leu Gly Cys Ser Leu Asn Gln Asn Ser Val Pro
            260                 265                 270

Asp Ile His Gly Val Glu Ala Pro Ala Arg Glu Gly Ala Met Ser Ala
        275                 280                 285

Gln Leu Gly Tyr Pro Val Val Gly Trp His Ile Ala Asn Lys Lys Pro
    290                 295                 300

Pro Leu Pro Lys Arg Val Arg Arg Gln Ile His Ala Thr Pro Thr Pro
305                 310                 315                 320

Val Thr Ala Ile Gly Pro Pro Thr Thr Ala Ile Gln Glu Pro Pro Ser
                325                 330                 335

Arg Ile Val Pro Thr Pro Thr Ser Pro Ala Ile Ala Pro Pro Thr Glu
                340                 345                 350

Thr Met Ala Pro Pro Val Arg Asp Pro Val Pro Gly Lys Pro Thr Val
                355                 360                 365

Thr Ile Arg Thr Arg Gly Ala Ile Ile Gln Thr Pro Thr Leu Gly Pro
        370                 375                 380

Ile Gln Pro Thr Arg Val Ser Glu Ala Gly Thr Thr Val Pro Gly Gln
385                 390                 395                 400

Ile Arg Pro Thr Met Thr Ile Pro Gly Tyr Val Glu Pro Thr Ala Val
                405                 410                 415
```

```
Ala Thr Pro Pro Thr Thr Thr Lys Lys Pro Arg Val Ser Thr Pro
            420             425             430

Lys Pro Ala Thr Pro Ser Thr Asp Ser Thr Thr Thr Thr Arg Arg
            435             440             445

Pro Thr Lys Lys Pro Arg Thr Pro Arg Pro Val Pro Arg Val Thr Thr
450             455             460

Lys Val Ser Ile Thr Arg Leu Glu Thr Ala Ser Pro Pro Thr Arg Ile
465             470             475             480

Arg Thr Thr Thr Ser Gly Val Pro Arg Gly Gly Glu Pro Asn Gln Arg
            485             490             495

Pro Glu Leu Lys Asn His Ile Asp Arg Val Asp Ala Trp Val Gly Thr
            500             505             510

Tyr Phe Glu Val Lys Ile Pro Ser Asp Thr Phe Tyr Asp His Glu Asp
            515             520             525

Thr Thr Thr Asp Lys Leu Lys Leu Thr Leu Lys Leu Arg Glu Gln Gln
            530             535             540

Leu Val Gly Glu Lys Ser Trp Val Gln Phe Asn Ser Asn Ser Gln Leu
545             550             555             560

Met Tyr Gly Leu Pro Asp Ser Ser His Val Gly Lys His Glu Tyr Phe
            565             570             575

Met His Ala Thr Asp Lys Gly Gly Leu Ser Ala Val Asp Ala Phe Glu
            580             585             590

Ile His Val His Arg Arg Pro Gln Gly Asp Arg Ala Pro Ala Arg Phe
            595             600             605

Lys Ala Lys Phe Val Gly Asp Pro Ala Leu Val Leu Asn Asp Ile His
            610             615             620

Lys Lys Ile Ala Leu Val Lys Lys Leu Ala Phe Ala Phe Gly Asp Arg
625             630             635             640

Asn Cys Ser Thr Ile Thr Leu Gln Asn Ile Thr Arg Gly Ser Ile Val
            645             650             655

Val Glu Trp Thr Asn Asn Thr Leu Pro Leu Pro Cys Pro Lys Glu
            660             665             670

Gln Ile Ala Gly Leu Ser Arg Arg Ile Ala Glu Asp Asp Gly Lys Pro
            675             680             685

Arg Pro Ala Phe Ser Asn Ala Leu Glu Pro Asp Phe Lys Ala Thr Ser
            690             695             700

Ile Thr Val Thr Gly Ser Gly Ser Cys Arg His Leu Gln Phe Ile Pro
705             710             715             720

Val Val Pro Pro Arg Arg Val Pro Ser Glu Ala Pro Thr Glu Val
            725             730             735

Pro Asp Arg Asp Pro Glu Lys Ser Ser Glu Asp Val Tyr Leu His
            740             745             750

Thr Val Ile Pro Ala Val Val Ala Ile Leu Leu Ile Ala Gly
            755             760             765

Ile Ile Ala Met Ile Cys Tyr Arg Lys Arg Lys Gly Lys Leu Thr
            770             775             780

Leu Glu Asp Gln Ala Thr Phe Ile Lys Lys Gly Val Pro Ile Ile Phe
785             790             795             800

Ala Asp Glu Leu Asp Asp Ser Lys Pro Pro Ser Ser Ser Met Pro
            805             810             815

Leu Ile Leu Gln Glu Glu Lys Ala Pro Leu Pro Pro Glu Tyr Pro
            820             825             830

Asn Gln Ser Val Pro Glu Thr Thr Pro Leu Asn Gln Asp Thr Met Gly
```

```
                          835                 840                 845
Glu Tyr Thr Pro Leu Arg Asp Glu Asp Pro Asn Ala Pro Pro Tyr Gln
    850                 855                 860

Pro Pro Pro Pro Phe Thr Val Pro Met Glu Gly Lys Gly Ser Arg Pro
865                 870                 875                 880

Lys Asn Met Thr Pro Tyr Arg Ser Pro Pro Tyr Val Pro Pro
                885                 890                 895

<210> SEQ ID NO 21
<211> LENGTH: 868
<212> TYPE: PRT
<213> ORGANISM: Homo sapiens

<400> SEQUENCE: 21

Gln Ser His Trp Pro Ser Glu Pro Ser Glu Ala Val Arg Asp Trp Glu
1               5                   10                  15

Asn Gln Leu Glu Ala Ser Met His Ser Val Leu Ser Asp Leu His Glu
            20                  25                  30

Ala Val Pro Thr Val Val Gly Ile Pro Asp Gly Thr Ala Val Val Gly
        35                  40                  45

Arg Ser Phe Arg Val Thr Ile Pro Thr Asp Leu Ile Ala Ser Ser Gly
    50                  55                  60

Asp Ile Ile Lys Val Ser Ala Ala Gly Lys Glu Ala Leu Pro Ser Trp
65                  70                  75                  80

Leu His Trp Asp Ser Gln Ser His Thr Leu Glu Gly Leu Pro Leu Asp
                85                  90                  95

Thr Asp Lys Gly Val His Tyr Ile Ser Val Ser Ala Thr Arg Leu Gly
            100                 105                 110

Ala Asn Gly Ser His Ile Pro Gln Thr Ser Ser Val Phe Ser Ile Glu
        115                 120                 125

Val Tyr Pro Glu Asp His Ser Asp Leu Gln Ser Val Arg Thr Ala Ser
    130                 135                 140

Pro Asp Pro Gly Glu Val Val Ser Ser Ala Cys Ala Ala Asp Glu Pro
145                 150                 155                 160

Val Thr Val Leu Thr Val Ile Leu Asp Ala Asp Leu Thr Lys Met Thr
                165                 170                 175

Pro Lys Gln Arg Ile Asp Leu Leu His Arg Met Arg Ser Phe Ser Glu
            180                 185                 190

Val Glu Leu His Asn Met Lys Leu Val Pro Val Val Asn Asn Arg Leu
        195                 200                 205

Phe Asp Met Ser Ala Phe Met Ala Gly Pro Gly Asn Pro Lys Lys Val
    210                 215                 220

Val Glu Asn Gly Ala Leu Leu Ser Trp Lys Leu Gly Cys Ser Leu Asn
225                 230                 235                 240

Gln Asn Ser Val Pro Asp Ile His Gly Val Glu Ala Pro Ala Arg Glu
                245                 250                 255

Gly Ala Met Ser Ala Gln Leu Gly Tyr Pro Val Val Gly Trp His Ile
            260                 265                 270

Ala Asn Lys Lys Pro Pro Leu Pro Lys Arg Val Arg Arg Gln Ile His
        275                 280                 285

Ala Thr Pro Thr Pro Val Thr Ala Ile Gly Pro Pro Thr Thr Ala Ile
    290                 295                 300

Gln Glu Pro Pro Ser Arg Ile Val Pro Thr Pro Thr Ser Pro Ala Ile
305                 310                 315                 320
```

```
Ala Pro Pro Thr Glu Thr Met Ala Pro Pro Val Arg Asp Pro Val Pro
                325                 330                 335

Gly Lys Pro Thr Val Thr Ile Arg Thr Arg Gly Ala Ile Ile Gln Thr
            340                 345                 350

Pro Thr Leu Gly Pro Ile Gln Pro Thr Arg Val Ser Glu Ala Gly Thr
            355                 360                 365

Thr Val Pro Gly Gln Ile Arg Pro Thr Met Thr Ile Pro Gly Tyr Val
        370                 375                 380

Glu Pro Thr Ala Val Ala Thr Pro Pro Thr Thr Thr Lys Lys Pro
385                 390                 395                 400

Arg Val Ser Thr Pro Lys Pro Ala Thr Pro Ser Thr Asp Ser Thr Thr
                405                 410                 415

Thr Thr Thr Arg Arg Pro Thr Lys Lys Pro Arg Thr Pro Arg Pro Val
            420                 425                 430

Pro Arg Val Thr Thr Lys Val Ser Ile Thr Arg Leu Glu Thr Ala Ser
        435                 440                 445

Pro Pro Thr Arg Ile Arg Thr Thr Thr Ser Gly Val Pro Arg Gly Gly
        450                 455                 460

Glu Pro Asn Gln Arg Pro Glu Leu Lys Asn His Ile Asp Arg Val Asp
465                 470                 475                 480

Ala Trp Val Gly Thr Tyr Phe Glu Val Lys Ile Pro Ser Asp Thr Phe
                485                 490                 495

Tyr Asp His Glu Asp Thr Thr Thr Asp Lys Leu Lys Leu Thr Leu Lys
                500                 505                 510

Leu Arg Glu Gln Gln Leu Val Gly Glu Lys Ser Trp Val Gln Phe Asn
            515                 520                 525

Ser Asn Ser Gln Leu Met Tyr Gly Leu Pro Asp Ser Ser His Val Gly
530                 535                 540

Lys His Glu Tyr Phe Met His Ala Thr Asp Lys Gly Gly Leu Ser Ala
545                 550                 555                 560

Val Asp Ala Phe Glu Ile His Val His Arg Arg Pro Gln Gly Asp Arg
                565                 570                 575

Ala Pro Ala Arg Phe Lys Ala Lys Phe Val Gly Asp Pro Ala Leu Val
            580                 585                 590

Leu Asn Asp Ile His Lys Lys Ile Ala Leu Val Lys Lys Leu Ala Phe
        595                 600                 605

Ala Phe Gly Asp Arg Asn Cys Ser Thr Ile Thr Leu Gln Asn Ile Thr
        610                 615                 620

Arg Gly Ser Ile Val Val Glu Trp Thr Asn Asn Thr Leu Pro Leu Glu
625                 630                 635                 640

Pro Cys Pro Lys Glu Gln Ile Ala Gly Leu Ser Arg Arg Ile Ala Glu
                645                 650                 655

Asp Asp Gly Lys Pro Arg Pro Ala Phe Ser Asn Ala Leu Glu Pro Asp
            660                 665                 670

Phe Lys Ala Thr Ser Ile Thr Val Thr Gly Ser Gly Ser Cys Arg His
        675                 680                 685

Leu Gln Phe Ile Pro Val Val Pro Pro Arg Arg Val Pro Ser Glu Ala
        690                 695                 700

Pro Pro Thr Glu Val Pro Asp Arg Asp Pro Glu Lys Ser Ser Glu Asp
705                 710                 715                 720

Asp Val Tyr Leu His Thr Val Ile Pro Ala Val Val Ala Ala Ile
                725                 730                 735

Leu Leu Ile Ala Gly Ile Ile Ala Met Ile Cys Tyr Arg Lys Lys Arg
```

```
                        740                 745                 750
Lys Gly Lys Leu Thr Leu Glu Asp Gln Ala Thr Phe Ile Lys Lys Gly
            755                 760                 765

Val Pro Ile Ile Phe Ala Asp Glu Leu Asp Asp Ser Lys Pro Pro Pro
770                 775                 780

Ser Ser Ser Met Pro Leu Ile Leu Gln Glu Glu Lys Ala Pro Leu Pro
785                 790                 795                 800

Pro Pro Glu Tyr Pro Asn Gln Ser Val Pro Glu Thr Thr Pro Leu Asn
            805                 810                 815

Gln Asp Thr Met Gly Glu Tyr Thr Pro Leu Arg Asp Glu Asp Pro Asn
            820                 825                 830

Ala Pro Pro Tyr Gln Pro Pro Pro Phe Thr Val Pro Met Glu Gly
            835                 840                 845

Lys Gly Ser Arg Pro Lys Asn Met Thr Pro Tyr Arg Ser Pro Pro Pro
            850                 855                 860

Tyr Val Pro Pro
865

<210> SEQ ID NO 22
<211> LENGTH: 650
<212> TYPE: PRT
<213> ORGANISM: Homo sapiens

<400> SEQUENCE: 22

Met Gly Pro Ala Ser Pro Ala Ala Arg Gly Leu Ser Arg Arg Pro Gly
1               5                   10                  15

Gln Pro Pro Leu Pro Leu Leu Leu Pro Leu Leu Leu Leu Leu Leu Arg
            20                  25                  30

Ala Gln Pro Ala Ile Gly Ser Leu Ala Gly Gly Ser Pro Gly Ala Ala
        35                  40                  45

Glu Ala Pro Gly Ser Ala Gln Val Ala Gly Leu Cys Gly Arg Leu Thr
50                  55                  60

Leu His Arg Asp Leu Arg Thr Gly Arg Trp Glu Pro Asp Pro Gln Arg
65                  70                  75                  80

Ser Arg Arg Cys Leu Arg Asp Pro Gln Arg Val Leu Glu Tyr Cys Arg
                85                  90                  95

Gln Met Tyr Pro Glu Leu Gln Ile Ala Arg Val Glu Gln Ala Thr Gln
            100                 105                 110

Ala Ile Pro Met Glu Arg Trp Cys Gly Gly Ser Arg Ser Gly Ser Cys
        115                 120                 125

Ala His Pro His His Gln Val Val Pro Phe Arg Cys Leu Pro Gly Glu
130                 135                 140

Phe Val Ser Glu Ala Leu Leu Val Pro Glu Gly Cys Arg Phe Leu His
145                 150                 155                 160

Gln Glu Arg Met Asp Gln Cys Glu Ser Ser Thr Arg Arg His Gln Glu
                165                 170                 175

Ala Gln Glu Ala Cys Ser Ser Gln Gly Leu Ile Leu His Gly Ser Gly
            180                 185                 190

Met Leu Leu Pro Cys Gly Ser Asp Arg Phe Arg Gly Val Glu Tyr Val
        195                 200                 205

Cys Cys Pro Pro Pro Gly Thr Pro Asp Pro Ser Gly Thr Ala Val Gly
210                 215                 220

Asp Pro Ser Thr Arg Ser Trp Pro Pro Gly Ser Arg Val Glu Gly Ala
225                 230                 235                 240
```

-continued

Glu Asp Glu Glu Glu Glu Ser Phe Pro Gln Pro Val Asp Asp Tyr
            245                 250                 255

Phe Val Glu Pro Pro Gln Ala Glu Glu Glu Glu Thr Val Pro Pro
            260                 265                 270

Pro Ser Ser His Thr Leu Ala Val Val Gly Lys Val Thr Pro Thr
            275                 280                 285

Arg Pro Thr Asp Gly Val Asp Ile Tyr Phe Gly Met Pro Gly Glu Ile
290                 295                 300

Ser Glu His Glu Gly Phe Leu Arg Ala Lys Met Asp Leu Glu Glu Arg
305                 310                 315                 320

Arg Met Arg Gln Ile Asn Glu Val Met Arg Glu Trp Ala Met Ala Asp
                325                 330                 335

Asn Gln Ser Lys Asn Leu Pro Lys Ala Asp Arg Gln Ala Leu Asn Glu
            340                 345                 350

His Phe Gln Ser Ile Leu Gln Thr Leu Glu Glu Gln Val Ser Gly Glu
            355                 360                 365

Arg Gln Arg Leu Val Glu Thr His Ala Thr Arg Val Ile Ala Leu Ile
370                 375                 380

Asn Asp Gln Arg Arg Ala Ala Leu Glu Gly Phe Leu Ala Ala Leu Gln
385                 390                 395                 400

Ala Asp Pro Pro Gln Ala Glu Arg Val Leu Leu Ala Leu Arg Arg Tyr
                405                 410                 415

Leu Arg Ala Glu Gln Lys Glu Gln Arg His Thr Leu Arg His Tyr Gln
            420                 425                 430

His Val Ala Ala Val Asp Pro Glu Lys Ala Gln Gln Met Arg Phe Gln
            435                 440                 445

Val His Thr His Leu Gln Val Ile Glu Glu Arg Val Asn Gln Ser Leu
450                 455                 460

Gly Leu Leu Asp Gln Asn Pro His Leu Ala Gln Glu Leu Arg Pro Gln
465                 470                 475                 480

Ile Gln Glu Leu Leu His Ser Glu His Leu Gly Pro Ser Glu Leu Glu
                485                 490                 495

Ala Pro Ala Pro Gly Gly Ser Ser Glu Asp Lys Gly Gly Leu Gln Pro
            500                 505                 510

Pro Asp Ser Lys Asp Asp Thr Pro Met Thr Leu Pro Lys Gly Ser Thr
            515                 520                 525

Glu Gln Asp Ala Ala Ser Pro Glu Lys Glu Lys Met Asn Pro Leu Glu
            530                 535                 540

Gln Tyr Glu Arg Lys Val Asn Ala Ser Val Pro Arg Gly Phe Pro Phe
545                 550                 555                 560

His Ser Ser Glu Ile Gln Arg Asp Glu Leu Ala Pro Ala Gly Thr Gly
                565                 570                 575

Val Ser Arg Glu Ala Val Ser Gly Leu Leu Ile Met Gly Ala Gly Gly
            580                 585                 590

Gly Ser Leu Ile Val Leu Ser Met Leu Leu Leu Arg Arg Lys Lys Pro
            595                 600                 605

Tyr Gly Ala Ile Ser His Gly Val Val Glu Val Asp Pro Met Leu Thr
            610                 615                 620

Leu Glu Glu Gln Gln Leu Arg Glu Leu Gln Arg His Gly Tyr Glu Asn
625                 630                 635                 640

Pro Thr Tyr Arg Phe Leu Glu Glu Arg Pro
                645                 650

```
<210> SEQ ID NO 23
<211> LENGTH: 612
<212> TYPE: PRT
<213> ORGANISM: Homo sapiens

<400> SEQUENCE: 23
```

| Ser | Leu | Ala | Gly | Gly | Ser | Pro | Gly | Ala | Glu | Ala | Pro | Gly | Ser | Ala |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Gln Val Ala Gly Leu Cys Gly Arg Leu Thr Leu His Arg Asp Leu Arg
                 20                 25                 30

Thr Gly Arg Trp Glu Pro Asp Pro Gln Arg Ser Arg Arg Cys Leu Arg
            35                 40                 45

Asp Pro Gln Arg Val Leu Glu Tyr Cys Arg Gln Met Tyr Pro Glu Leu
   50                     55                 60

Gln Ile Ala Arg Val Glu Gln Ala Thr Gln Ala Ile Pro Met Glu Arg
65                 70                 75                 80

Trp Cys Gly Gly Ser Arg Ser Gly Ser Cys Ala His Pro His His Gln
                 85                 90                 95

Val Val Pro Phe Arg Cys Leu Pro Gly Glu Phe Val Ser Glu Ala Leu
            100                105               110

Leu Val Pro Glu Gly Cys Arg Phe Leu His Gln Glu Arg Met Asp Gln
            115                120               125

Cys Glu Ser Ser Thr Arg Arg His Gln Glu Ala Gln Glu Ala Cys Ser
   130                     135                140

Ser Gln Gly Leu Ile Leu His Gly Ser Gly Met Leu Leu Pro Cys Gly
145                150                155               160

Ser Asp Arg Phe Arg Gly Val Glu Tyr Val Cys Cys Pro Pro Pro Gly
            165                170               175

Thr Pro Asp Pro Ser Gly Thr Ala Val Gly Asp Pro Ser Thr Arg Ser
            180                185               190

Trp Pro Pro Gly Ser Arg Val Glu Gly Ala Glu Asp Glu Glu Glu Glu
            195                200               205

Glu Ser Phe Pro Gln Pro Val Asp Asp Tyr Phe Val Glu Pro Pro Gln
   210                     215                220

Ala Glu Glu Glu Glu Thr Val Pro Pro Ser Ser His Thr Leu
225                230                235               240

Ala Val Val Gly Lys Val Thr Pro Thr Pro Arg Pro Thr Asp Gly Val
            245                250               255

Asp Ile Tyr Phe Gly Met Pro Gly Glu Ile Ser Glu His Glu Gly Phe
            260                265               270

Leu Arg Ala Lys Met Asp Leu Glu Glu Arg Arg Met Arg Gln Ile Asn
            275                280               285

Glu Val Met Arg Glu Trp Ala Met Ala Asp Asn Gln Ser Lys Asn Leu
            290                295               300

Pro Lys Ala Asp Arg Gln Ala Leu Asn Glu His Phe Gln Ser Ile Leu
305                310                315               320

Gln Thr Leu Glu Glu Gln Val Ser Gly Glu Arg Gln Arg Leu Val Glu
            325                330               335

Thr His Ala Thr Arg Val Ile Ala Leu Ile Asn Asp Gln Arg Arg Ala
            340                345               350

Ala Leu Glu Gly Phe Leu Ala Ala Leu Gln Ala Asp Pro Pro Gln Ala
            355                360               365

Glu Arg Val Leu Leu Ala Leu Arg Arg Tyr Leu Arg Ala Glu Gln Lys
            370                375               380

```
Glu Gln Arg His Thr Leu Arg His Tyr Gln His Val Ala Ala Val Asp
385                 390                 395                 400

Pro Glu Lys Ala Gln Gln Met Arg Phe Gln Val His Thr His Leu Gln
            405                 410                 415

Val Ile Glu Glu Arg Val Asn Gln Ser Leu Gly Leu Leu Asp Gln Asn
        420                 425                 430

Pro His Leu Ala Gln Glu Leu Arg Pro Gln Ile Gln Glu Leu Leu His
    435                 440                 445

Ser Glu His Leu Gly Pro Ser Glu Leu Glu Ala Pro Ala Pro Gly Gly
450                 455                 460

Ser Ser Glu Asp Lys Gly Gly Leu Gln Pro Pro Asp Ser Lys Asp Asp
465                 470                 475                 480

Thr Pro Met Thr Leu Pro Lys Gly Ser Thr Glu Gln Asp Ala Ala Ser
            485                 490                 495

Pro Glu Lys Glu Lys Met Asn Pro Leu Glu Gln Tyr Glu Arg Lys Val
        500                 505                 510

Asn Ala Ser Val Pro Arg Gly Phe Pro Phe His Ser Ser Glu Ile Gln
    515                 520                 525

Arg Asp Glu Leu Ala Pro Ala Gly Thr Gly Val Ser Arg Glu Ala Val
530                 535                 540

Ser Gly Leu Leu Ile Met Gly Ala Gly Gly Ser Leu Ile Val Leu
545                 550                 555                 560

Ser Met Leu Leu Leu Arg Arg Lys Lys Pro Tyr Gly Ala Ile Ser His
            565                 570                 575

Gly Val Val Glu Val Asp Pro Met Leu Thr Leu Glu Glu Gln Gln Leu
        580                 585                 590

Arg Glu Leu Gln Arg His Gly Tyr Glu Asn Pro Thr Tyr Arg Phe Leu
    595                 600                 605

Glu Glu Arg Pro
610

<210> SEQ ID NO 24
<211> LENGTH: 979
<212> TYPE: PRT
<213> ORGANISM: Homo sapiens

<400> SEQUENCE: 24

Met Arg Arg Pro Arg Pro Gly Gly Leu Gly Gly Ser Gly Gly Leu
1               5                   10                  15

Arg Leu Leu Leu Cys Leu Leu Leu Ser Ser Arg Pro Gly Gly Cys
            20                  25                  30

Ser Ala Val Ser Ala His Gly Cys Leu Phe Asp Arg Arg Leu Cys Ser
            35                  40                  45

His Leu Glu Val Cys Ile Gln Asp Gly Leu Phe Gly Gln Cys Gln Val
    50                  55                  60

Gly Val Gly Gln Ala Arg Pro Leu Leu Gln Val Thr Ser Pro Val Leu
65                  70                  75                  80

Gln Arg Leu Gln Gly Val Leu Arg Gln Leu Met Ser Gln Gly Leu Ser
            85                  90                  95

Trp His Asp Asp Leu Thr Gln Tyr Val Ile Ser Gln Glu Met Glu Arg
            100                 105                 110

Ile Pro Arg Leu Arg Pro Pro Glu Pro Arg Pro Arg Asp Arg Ser Gly
        115                 120                 125

Leu Ala Pro Lys Arg Pro Gly Pro Ala Gly Glu Leu Leu Leu Gln Asp
    130                 135                 140
```

```
Ile Pro Thr Gly Ser Ala Pro Ala Ala Gln His Arg Leu Pro Gln Pro
145                 150                 155                 160

Pro Val Gly Lys Gly Ala Gly Ala Ser Ser Leu Ser Pro Leu
        165                 170                 175

Gln Ala Glu Leu Leu Pro Leu Leu Glu His Leu Leu Leu Pro Pro
        180                 185                 190

Gln Pro Pro His Pro Ser Leu Ser Tyr Glu Pro Ala Leu Leu Gln Pro
        195                 200                 205

Tyr Leu Phe His Gln Phe Gly Ser Arg Asp Gly Ser Arg Val Ser Glu
210                 215                 220

Gly Ser Pro Gly Met Val Ser Val Gly Pro Leu Pro Lys Ala Glu Ala
225                 230                 235                 240

Pro Ala Leu Phe Ser Arg Thr Ala Ser Lys Gly Ile Phe Gly Asp His
                245                 250                 255

Pro Gly His Ser Tyr Gly Asp Leu Pro Gly Pro Ser Pro Ala Gln Leu
        260                 265                 270

Phe Gln Asp Ser Gly Leu Leu Tyr Leu Ala Gln Glu Leu Pro Ala Pro
        275                 280                 285

Ser Arg Ala Arg Val Pro Arg Leu Pro Glu Gln Gly Ser Ser Ser Arg
290                 295                 300

Ala Glu Asp Ser Pro Glu Gly Tyr Glu Lys Glu Gly Leu Gly Asp Arg
305                 310                 315                 320

Gly Glu Lys Pro Ala Ser Pro Ala Val Gln Pro Asp Ala Ala Leu Gln
                325                 330                 335

Arg Leu Ala Ala Val Leu Ala Gly Tyr Gly Val Glu Leu Arg Gln Leu
                340                 345                 350

Thr Pro Glu Gln Leu Ser Thr Leu Leu Thr Leu Leu Gln Leu Leu Pro
        355                 360                 365

Lys Gly Ala Gly Arg Asn Pro Gly Gly Val Val Asn Val Gly Ala Asp
        370                 375                 380

Ile Lys Lys Thr Met Glu Gly Pro Val Glu Gly Arg Asp Thr Ala Glu
385                 390                 395                 400

Leu Pro Ala Arg Thr Ser Pro Met Pro Gly His Pro Thr Ala Ser Pro
                405                 410                 415

Thr Ser Ser Glu Val Gln Gln Val Pro Ser Pro Val Ser Ser Glu Pro
                420                 425                 430

Pro Lys Ala Ala Arg Pro Pro Val Thr Pro Val Leu Leu Glu Lys Lys
        435                 440                 445

Ser Pro Leu Gly Gln Ser Gln Pro Thr Val Ala Gly Gln Pro Ser Ala
        450                 455                 460

Arg Pro Ala Ala Glu Glu Tyr Gly Tyr Ile Val Thr Asp Gln Lys Pro
465                 470                 475                 480

Leu Ser Leu Ala Ala Gly Val Lys Leu Leu Glu Ile Leu Ala Glu His
                485                 490                 495

Val His Met Ser Ser Gly Ser Phe Ile Asn Ile Ser Val Val Gly Pro
                500                 505                 510

Ala Leu Thr Phe Arg Ile Arg His Asn Glu Gln Asn Leu Ser Leu Ala
        515                 520                 525

Asp Val Thr Gln Gln Ala Gly Leu Val Lys Ser Glu Leu Glu Ala Gln
        530                 535                 540

Thr Gly Leu Gln Ile Leu Gln Thr Gly Val Gly Gln Arg Glu Glu Ala
545                 550                 555                 560
```

```
Ala Ala Val Leu Pro Gln Thr Ala His Ser Thr Ser Pro Met Arg Ser
                565                 570                 575

Val Leu Leu Thr Leu Val Ala Leu Ala Gly Val Ala Gly Leu Leu Val
            580                 585                 590

Ala Leu Ala Val Ala Leu Cys Val Arg Gln His Ala Arg Gln Gln Asp
        595                 600                 605

Lys Glu Arg Leu Ala Ala Leu Gly Pro Glu Gly Ala His Gly Asp Thr
    610                 615                 620

Thr Phe Glu Tyr Gln Asp Leu Cys Arg Gln His Met Ala Thr Lys Ser
625                 630                 635                 640

Leu Phe Asn Arg Ala Glu Gly Pro Pro Glu Pro Ser Arg Val Ser Ser
                645                 650                 655

Val Ser Ser Gln Phe Ser Asp Ala Ala Gln Ala Ser Pro Ser Ser His
            660                 665                 670

Ser Ser Thr Pro Ser Trp Cys Glu Glu Pro Ala Gln Ala Asn Met Asp
        675                 680                 685

Ile Ser Thr Gly His Met Ile Leu Ala Tyr Met Glu Asp His Leu Arg
    690                 695                 700

Asn Arg Asp Arg Leu Ala Lys Glu Trp Gln Ala Leu Cys Ala Tyr Gln
705                 710                 715                 720

Ala Glu Pro Asn Thr Cys Ala Thr Ala Gln Gly Glu Gly Asn Ile Lys
                725                 730                 735

Lys Asn Arg His Pro Asp Phe Leu Pro Tyr Asp His Ala Arg Ile Lys
            740                 745                 750

Leu Lys Val Glu Ser Ser Pro Ser Arg Ser Asp Tyr Ile Asn Ala Ser
        755                 760                 765

Pro Ile Ile Glu His Asp Pro Arg Met Pro Ala Tyr Ile Ala Thr Gln
    770                 775                 780

Gly Pro Leu Ser His Thr Ile Ala Asp Phe Trp Gln Met Val Trp Glu
785                 790                 795                 800

Ser Gly Cys Thr Val Ile Val Met Leu Thr Pro Leu Val Glu Asp Gly
                805                 810                 815

Val Lys Gln Cys Asp Arg Tyr Trp Pro Asp Glu Gly Ala Ser Leu Tyr
            820                 825                 830

His Val Tyr Glu Val Asn Leu Val Ser Glu His Ile Trp Cys Glu Asp
        835                 840                 845

Phe Leu Val Arg Ser Phe Tyr Leu Lys Asn Val Gln Thr Gln Glu Thr
    850                 855                 860

Arg Thr Leu Thr Gln Phe His Phe Leu Ser Trp Pro Ala Glu Gly Thr
865                 870                 875                 880

Pro Ala Ser Thr Arg Pro Leu Leu Asp Phe Arg Arg Lys Val Asn Lys
                885                 890                 895

Cys Tyr Arg Gly Arg Ser Cys Pro Ile Ile Val His Cys Ser Asp Gly
            900                 905                 910

Ala Gly Arg Thr Gly Thr Tyr Ile Leu Ile Asp Met Val Leu Asn Arg
        915                 920                 925

Met Ala Lys Gly Val Lys Glu Ile Asp Ile Ala Ala Thr Leu Glu His
    930                 935                 940

Val Arg Asp Gln Arg Pro Gly Leu Val Arg Ser Lys Asp Gln Phe Glu
945                 950                 955                 960

Phe Ala Leu Thr Ala Val Ala Glu Glu Val Asn Ala Ile Leu Lys Ala
                965                 970                 975

Leu Pro Gln
```

<210> SEQ ID NO 25
<211> LENGTH: 945
<212> TYPE: PRT
<213> ORGANISM: Homo sapiens

<400> SEQUENCE: 25

```
Val Ser Ala His Gly Cys Leu Phe Asp Arg Arg Leu Cys Ser His Leu
1               5                   10                  15

Glu Val Cys Ile Gln Asp Gly Leu Phe Gly Gln Cys Gln Val Gly Val
            20                  25                  30

Gly Gln Ala Arg Pro Leu Leu Gln Val Thr Ser Pro Val Leu Gln Arg
        35                  40                  45

Leu Gln Gly Val Leu Arg Gln Leu Met Ser Gln Gly Leu Ser Trp His
    50                  55                  60

Asp Asp Leu Thr Gln Tyr Val Ile Ser Gln Glu Met Glu Arg Ile Pro
65                  70                  75                  80

Arg Leu Arg Pro Pro Glu Pro Arg Pro Arg Asp Arg Ser Gly Leu Ala
                85                  90                  95

Pro Lys Arg Pro Gly Pro Ala Gly Glu Leu Leu Leu Gln Asp Ile Pro
            100                 105                 110

Thr Gly Ser Ala Pro Ala Ala Gln His Arg Leu Pro Gln Pro Pro Val
        115                 120                 125

Gly Lys Gly Gly Ala Gly Ala Ser Ser Ser Leu Ser Pro Leu Gln Ala
    130                 135                 140

Glu Leu Leu Pro Pro Leu Leu Glu His Leu Leu Leu Pro Pro Gln Pro
145                 150                 155                 160

Pro His Pro Ser Leu Ser Tyr Glu Pro Ala Leu Leu Gln Pro Tyr Leu
                165                 170                 175

Phe His Gln Phe Gly Ser Arg Asp Gly Ser Arg Val Ser Glu Gly Ser
            180                 185                 190

Pro Gly Met Val Ser Val Gly Pro Leu Pro Lys Ala Glu Ala Pro Ala
        195                 200                 205

Leu Phe Ser Arg Thr Ala Ser Lys Gly Ile Phe Gly Asp His Pro Gly
    210                 215                 220

His Ser Tyr Gly Asp Leu Pro Gly Pro Ser Pro Ala Gln Leu Phe Gln
225                 230                 235                 240

Asp Ser Gly Leu Leu Tyr Leu Ala Gln Glu Leu Pro Ala Pro Ser Arg
                245                 250                 255

Ala Arg Val Pro Arg Leu Pro Glu Gln Gly Ser Ser Ser Arg Ala Glu
            260                 265                 270

Asp Ser Pro Glu Gly Tyr Glu Lys Glu Gly Leu Gly Asp Arg Gly Glu
        275                 280                 285

Lys Pro Ala Ser Pro Ala Val Gln Pro Asp Ala Ala Leu Gln Arg Leu
    290                 295                 300

Ala Ala Val Leu Ala Gly Tyr Gly Val Glu Leu Arg Gln Leu Thr Pro
305                 310                 315                 320

Glu Gln Leu Ser Thr Leu Leu Thr Leu Leu Gln Leu Pro Lys Gly
                325                 330                 335

Ala Gly Arg Asn Pro Gly Val Val Asn Val Gly Ala Asp Ile Lys
            340                 345                 350

Lys Thr Met Glu Gly Pro Val Glu Gly Arg Asp Thr Ala Glu Leu Pro
        355                 360                 365

Ala Arg Thr Ser Pro Met Pro Gly His Pro Thr Ala Ser Pro Thr Ser
```

```
        370                 375                 380
Ser Glu Val Gln Gln Val Pro Ser Pro Val Ser Ser Glu Pro Pro Lys
385                 390                 395                 400

Ala Ala Arg Pro Pro Val Thr Pro Val Leu Leu Glu Lys Lys Ser Pro
                405                 410                 415

Leu Gly Gln Ser Gln Pro Thr Val Ala Gly Gln Pro Ser Ala Arg Pro
                420                 425                 430

Ala Ala Glu Glu Tyr Gly Tyr Ile Val Thr Asp Gln Lys Pro Leu Ser
                435                 440                 445

Leu Ala Ala Gly Val Lys Leu Leu Glu Ile Leu Ala Glu His Val His
                450                 455                 460

Met Ser Ser Gly Ser Phe Ile Asn Ile Ser Val Val Gly Pro Ala Leu
465                 470                 475                 480

Thr Phe Arg Ile Arg His Asn Glu Gln Asn Leu Ser Leu Ala Asp Val
                485                 490                 495

Thr Gln Gln Ala Gly Leu Val Lys Ser Glu Leu Glu Ala Gln Thr Gly
                500                 505                 510

Leu Gln Ile Leu Gln Thr Gly Val Gly Gln Arg Glu Glu Ala Ala Ala
                515                 520                 525

Val Leu Pro Gln Thr Ala His Ser Thr Ser Pro Met Arg Ser Val Leu
                530                 535                 540

Leu Thr Leu Val Ala Leu Ala Gly Val Ala Gly Leu Leu Val Ala Leu
545                 550                 555                 560

Ala Val Ala Leu Cys Val Arg Gln His Ala Arg Gln Gln Asp Lys Glu
                565                 570                 575

Arg Leu Ala Ala Leu Gly Pro Glu Gly Ala His Gly Asp Thr Thr Phe
                580                 585                 590

Glu Tyr Gln Asp Leu Cys Arg Gln His Met Ala Thr Lys Ser Leu Phe
                595                 600                 605

Asn Arg Ala Glu Gly Pro Pro Glu Pro Ser Arg Val Ser Ser Val Ser
                610                 615                 620

Ser Gln Phe Ser Asp Ala Ala Gln Ala Ser Pro Ser Ser His Ser Ser
625                 630                 635                 640

Thr Pro Ser Trp Cys Glu Glu Pro Ala Gln Ala Asn Met Asp Ile Ser
                645                 650                 655

Thr Gly His Met Ile Leu Ala Tyr Met Glu Asp His Leu Arg Asn Arg
                660                 665                 670

Asp Arg Leu Ala Lys Glu Trp Gln Ala Leu Cys Ala Tyr Gln Ala Glu
                675                 680                 685

Pro Asn Thr Cys Ala Thr Ala Gln Gly Glu Gly Asn Ile Lys Lys Asn
                690                 695                 700

Arg His Pro Asp Phe Leu Pro Tyr Asp His Ala Arg Ile Lys Leu Lys
705                 710                 715                 720

Val Glu Ser Ser Pro Ser Arg Ser Asp Tyr Ile Asn Ala Ser Pro Ile
                725                 730                 735

Ile Glu His Asp Pro Arg Met Pro Ala Tyr Ile Ala Thr Gln Gly Pro
                740                 745                 750

Leu Ser His Thr Ile Ala Asp Phe Trp Gln Met Val Trp Glu Ser Gly
                755                 760                 765

Cys Thr Val Ile Val Met Leu Thr Pro Leu Val Glu Asp Gly Val Lys
                770                 775                 780

Gln Cys Asp Arg Tyr Trp Pro Asp Glu Gly Ala Ser Leu Tyr His Val
785                 790                 795                 800
```

```
Tyr Glu Val Asn Leu Val Ser Glu His Ile Trp Cys Glu Asp Phe Leu
            805                 810                 815

Val Arg Ser Phe Tyr Leu Lys Asn Val Gln Thr Gln Glu Thr Arg Thr
        820                 825                 830

Leu Thr Gln Phe His Phe Leu Ser Trp Pro Ala Glu Gly Thr Pro Ala
    835                 840                 845

Ser Thr Arg Pro Leu Leu Asp Phe Arg Arg Lys Val Asn Lys Cys Tyr
850                 855                 860

Arg Gly Arg Ser Cys Pro Ile Ile Val His Cys Ser Asp Gly Ala Gly
865                 870                 875                 880

Arg Thr Gly Thr Tyr Ile Leu Ile Asp Met Val Leu Asn Arg Met Ala
                885                 890                 895

Lys Gly Val Lys Glu Ile Asp Ile Ala Ala Thr Leu Glu His Val Arg
                900                 905                 910

Asp Gln Arg Pro Gly Leu Val Arg Ser Lys Asp Gln Phe Glu Phe Ala
            915                 920                 925

Leu Thr Ala Val Ala Glu Glu Val Asn Ala Ile Leu Lys Ala Leu Pro
        930                 935                 940

Gln
945

<210> SEQ ID NO 26
<211> LENGTH: 366
<212> TYPE: PRT
<213> ORGANISM: Homo sapiens

<400> SEQUENCE: 26

Met Leu Leu Leu Arg Cys Gln Leu Lys Gln Ala Pro Pro Gln Lys Val
1               5                   10                  15

Ser Phe Arg Phe Cys Val Val Met Gly Lys Gln Gln Ser Lys Leu Lys
            20                  25                  30

His Ser Thr Tyr Lys Tyr Gly Pro Asp Glu Ile Ile Glu Glu Arg Ile
        35                  40                  45

Gln Thr Lys Ala Phe Gln Glu Tyr Ser Pro Ala His Met Asp Thr Val
    50                  55                  60

Ser Val Ala Ala Leu Asn Ser Asp Leu Cys Val Ser Gly Gly Lys
65                  70                  75              80

Asp Lys Thr Val Val Ala Tyr Asn Trp Lys Thr Gly Asn Val Val Lys
                85                  90                  95

Arg Phe Lys Gly His Glu His Glu Ile Thr Lys Val Ala Cys Ile Pro
            100                 105                 110

Lys Ser Ser Gln Phe Phe Ser Ala Ser Arg Asp Arg Met Val Met Met
        115                 120                 125

Trp Asp Leu His Gly Ser Ser Gln Pro Arg Gln Gln Leu Cys Gly His
    130                 135                 140

Ala Met Val Val Thr Gly Leu Ala Val Ser Pro Asp Ser Ser Gln Leu
145                 150                 155                 160

Cys Thr Gly Ser Arg Asp Asn Thr Leu Leu Leu Trp Asp Val Val Thr
                165                 170                 175

Gly Gln Ser Val Glu Arg Ala Ser Val Ser Arg Asn Val Val Thr His
            180                 185                 190

Leu Cys Trp Val Pro Arg Glu Pro Tyr Ile Leu Gln Thr Ser Glu Asp
        195                 200                 205

Lys Thr Leu Arg Leu Trp Asp Ser Arg Gly Leu Gln Val Ala His Met
```

```
                    210                 215                 220
Phe Pro Ala Lys Gln His Ile Gln Thr Tyr Cys Glu Val Ser Val Asp
225                 230                 235                 240

Gly His Lys Cys Ile Ser Cys Ser Asn Gly Phe Gly Glu Gly Cys
                    245                 250                 255

Glu Ala Thr Leu Trp Asp Leu Arg Gln Thr Arg Asn Arg Ile Cys Glu
                260                 265                 270

Tyr Lys Gly His Phe Gln Thr Val Ala Ser Cys Val Phe Leu Pro Arg
                275                 280                 285

Ala Leu Ala Leu Met Pro Leu Ile Ala Thr Ser Ser His Asp Cys Lys
                290                 295                 300

Val Lys Ile Trp Asn Gln Asp Thr Gly Ala Cys Leu Phe Thr Leu Ser
305                 310                 315                 320

Leu Asp Gly Ser Gly Pro Leu Thr Ser Leu Ala Val Gly Asp Ala Ile
                325                 330                 335

Ser Leu Leu Cys Ala Ser Phe Asn Arg Gly Ile His Leu Leu Arg Met
                340                 345                 350

Asp His Ser Gln Gly Leu Glu Leu Gln Glu Val Ala Ala Phe
                355                 360                 365

<210> SEQ ID NO 27
<211> LENGTH: 343
<212> TYPE: PRT
<213> ORGANISM: Homo sapiens

<400> SEQUENCE: 27

Met Ala Gln Lys Gly Val Leu Gly Pro Gly Gln Leu Gly Ala Val Ala
1               5                   10                  15

Ile Leu Leu Tyr Leu Gly Leu Leu Arg Ser Gly Thr Gly Ala Glu Gly
                20                  25                  30

Ala Glu Ala Pro Cys Gly Val Ala Pro Gln Ala Arg Ile Thr Gly Gly
                35                  40                  45

Ser Ser Ala Val Ala Gly Gln Trp Pro Trp Gln Val Ser Ile Thr Tyr
            50                  55                  60

Glu Gly Val His Val Cys Gly Gly Ser Leu Val Ser Glu Gln Trp Val
65                  70                  75                  80

Leu Ser Ala Ala His Cys Phe Pro Ser Glu His His Lys Glu Ala Tyr
                85                  90                  95

Glu Val Lys Leu Gly Ala His Gln Leu Asp Ser Tyr Ser Glu Asp Ala
                100                 105                 110

Lys Val Ser Thr Leu Lys Asp Ile Ile Pro His Pro Ser Tyr Leu Gln
                115                 120                 125

Glu Gly Ser Gln Gly Asp Ile Ala Leu Leu Gln Leu Ser Arg Pro Ile
                130                 135                 140

Thr Phe Ser Arg Tyr Ile Arg Pro Ile Cys Leu Pro Ala Ala Asn Ala
145                 150                 155                 160

Ser Phe Pro Asn Gly Leu His Cys Thr Val Thr Gly Trp Gly His Val
                165                 170                 175

Ala Pro Ser Val Ser Leu Leu Thr Pro Lys Pro Leu Gln Gln Leu Glu
                180                 185                 190

Val Pro Leu Ile Ser Arg Glu Thr Cys Asn Cys Leu Tyr Asn Ile Asp
                195                 200                 205

Ala Lys Pro Glu Glu Pro His Phe Val Gln Glu Asp Met Val Cys Ala
                210                 215                 220
```

-continued

Gly Tyr Val Glu Gly Gly Lys Asp Ala Cys Gln Gly Asp Ser Gly Gly
225                 230                 235                 240

Pro Leu Ser Cys Pro Val Glu Gly Leu Trp Tyr Leu Thr Gly Ile Val
            245                 250                 255

Ser Trp Gly Asp Ala Cys Gly Ala Arg Asn Arg Pro Gly Val Tyr Thr
        260                 265                 270

Leu Ala Ser Ser Tyr Ala Ser Trp Ile Gln Ser Lys Val Thr Glu Leu
    275                 280                 285

Gln Pro Arg Val Val Pro Gln Thr Gln Glu Ser Gln Pro Asp Ser Asn
290                 295                 300

Leu Cys Gly Ser His Leu Ala Phe Ser Ser Ala Pro Ala Gln Gly Leu
305                 310                 315                 320

Leu Arg Pro Ile Leu Phe Leu Pro Leu Gly Leu Ala Leu Gly Leu Leu
                325                 330                 335

Ser Pro Trp Leu Ser Glu His
            340

<210> SEQ ID NO 28
<211> LENGTH: 311
<212> TYPE: PRT
<213> ORGANISM: Homo sapiens

<400> SEQUENCE: 28

Ala Glu Ala Pro Cys Gly Val Ala Pro Gln Ala Arg Ile Thr Gly Gly
1               5                   10                  15

Ser Ser Ala Val Ala Gly Gln Trp Pro Trp Gln Val Ser Ile Thr Tyr
            20                  25                  30

Glu Gly Val His Val Cys Gly Gly Ser Leu Val Ser Glu Gln Trp Val
        35                  40                  45

Leu Ser Ala Ala His Cys Phe Pro Ser Glu His His Lys Glu Ala Tyr
    50                  55                  60

Glu Val Lys Leu Gly Ala His Gln Leu Asp Ser Tyr Ser Glu Asp Ala
65                  70                  75                  80

Lys Val Ser Thr Leu Lys Asp Ile Ile Pro His Pro Ser Tyr Leu Gln
                85                  90                  95

Glu Gly Ser Gln Gly Asp Ile Ala Leu Leu Gln Leu Ser Arg Pro Ile
            100                 105                 110

Thr Phe Ser Arg Tyr Ile Arg Pro Ile Cys Leu Pro Ala Ala Asn Ala
        115                 120                 125

Ser Phe Pro Asn Gly Leu His Cys Thr Val Thr Gly Trp Gly His Val
    130                 135                 140

Ala Pro Ser Val Ser Leu Leu Thr Pro Lys Pro Leu Gln Gln Leu Glu
145                 150                 155                 160

Val Pro Leu Ile Ser Arg Glu Thr Cys Asn Cys Leu Tyr Asn Ile Asp
                165                 170                 175

Ala Lys Pro Glu Glu Pro His Phe Val Gln Glu Asp Met Val Cys Ala
            180                 185                 190

Gly Tyr Val Glu Gly Gly Lys Asp Ala Cys Gln Gly Asp Ser Gly Gly
        195                 200                 205

Pro Leu Ser Cys Pro Val Glu Gly Leu Trp Tyr Leu Thr Gly Ile Val
    210                 215                 220

Ser Trp Gly Asp Ala Cys Gly Ala Arg Asn Arg Pro Gly Val Tyr Thr
225                 230                 235                 240

Leu Ala Ser Ser Tyr Ala Ser Trp Ile Gln Ser Lys Val Thr Glu Leu
                245                 250                 255

-continued

```
Gln Pro Arg Val Val Pro Gln Thr Gln Glu Ser Gln Pro Asp Ser Asn
            260                 265                 270

Leu Cys Gly Ser His Leu Ala Phe Ser Ser Ala Pro Ala Gln Gly Leu
            275                 280                 285

Leu Arg Pro Ile Leu Phe Leu Pro Leu Gly Leu Ala Leu Gly Leu Leu
            290                 295                 300

Ser Pro Trp Leu Ser Glu His
305                 310

<210> SEQ ID NO 29
<211> LENGTH: 316
<212> TYPE: PRT
<213> ORGANISM: Homo sapiens

<400> SEQUENCE: 29

Met Leu Leu Leu Leu Leu Pro Leu Leu Trp Gly Arg Glu Arg Val
1               5                   10                  15

Glu Gly Gln Lys Ser Asn Arg Lys Asp Tyr Ser Leu Thr Met Gln Ser
            20                  25                  30

Ser Val Thr Val Gln Glu Gly Met Cys Ala His Val Arg Cys Ser Phe
            35                  40                  45

Ser Tyr Pro Val Asp Ser Gln Thr Asp Ser Asp Pro Val His Gly Tyr
50                  55                  60

Trp Phe Arg Ala Gly Asn Asp Ile Ser Trp Lys Ala Pro Val Ala Thr
65                  70                  75                  80

Asn Asn Pro Ala Trp Ala Val Gln Glu Glu Thr Arg Asp Arg Phe His
            85                  90                  95

Leu Leu Gly Asp Pro Gln Thr Lys Asn Cys Thr Leu Ser Ile Arg Asp
            100                 105                 110

Ala Arg Met Ser Asp Ala Gly Arg Tyr Phe Phe Arg Met Glu Lys Gly
            115                 120                 125

Asn Ile Lys Trp Asn Tyr Lys Tyr Asp Gln Leu Ser Val Asn Val Thr
            130                 135                 140

Asp Pro Pro Gln Asn Leu Thr Val Thr Val Phe Gln Gly Glu Gly Thr
145                 150                 155                 160

Ala Ser Thr Ala Leu Gly Asn Ser Ser Ser Leu Ser Val Leu Glu Gly
            165                 170                 175

Gln Ser Leu Arg Leu Val Cys Ala Val Asp Ser Asn Pro Pro Ala Arg
            180                 185                 190

Leu Ser Trp Thr Trp Arg Ser Leu Thr Leu Tyr Pro Ser Gln Pro Ser
            195                 200                 205

Asn Pro Leu Val Leu Glu Leu Gln Val His Leu Gly Asp Glu Gly Glu
            210                 215                 220

Phe Thr Cys Arg Ala Gln Asn Ser Leu Gly Ser Gln His Val Ser Leu
225                 230                 235                 240

Asn Leu Ser Leu Gln Gln Glu Tyr Thr Gly Lys Met Arg Pro Val Ser
            245                 250                 255

Gly Val Leu Leu Gly Ala Val Gly Gly Ala Gly Ala Thr Ala Leu Val
            260                 265                 270

Phe Leu Ser Phe Cys Val Ile Phe Ile Val Val Arg Ser Cys Arg Lys
            275                 280                 285

Lys Ser Ala Arg Pro Ala Ala Asp Val Gly Asp Ile Gly Met Lys Asp
            290                 295                 300

Ala Asn Thr Ile Arg Gly Ser Ala Leu Arg Val Thr
```

<210> SEQ ID NO 30
<211> LENGTH: 298
<212> TYPE: PRT
<213> ORGANISM: Homo sapiens

<400> SEQUENCE: 30

Gln Lys Ser Asn Arg Lys Asp Tyr Ser Leu Thr Met Gln Ser Ser Val
1               5                   10                  15

Thr Val Gln Glu Gly Met Cys Ala His Val Arg Cys Ser Phe Ser Tyr
            20                  25                  30

Pro Val Asp Ser Gln Thr Asp Ser Asp Pro Val His Gly Tyr Trp Phe
        35                  40                  45

Arg Ala Gly Asn Asp Ile Ser Trp Lys Ala Pro Val Ala Thr Asn Asn
    50                  55                  60

Pro Ala Trp Ala Val Gln Glu Glu Thr Arg Asp Arg Phe His Leu Leu
65                  70                  75                  80

Gly Asp Pro Gln Thr Lys Asn Cys Thr Leu Ser Ile Arg Asp Ala Arg
                85                  90                  95

Met Ser Asp Ala Gly Arg Tyr Phe Phe Arg Met Glu Lys Gly Asn Ile
            100                 105                 110

Lys Trp Asn Tyr Lys Tyr Asp Gln Leu Ser Val Asn Val Thr Asp Pro
        115                 120                 125

Pro Gln Asn Leu Thr Val Thr Val Phe Gln Gly Glu Gly Thr Ala Ser
    130                 135                 140

Thr Ala Leu Gly Asn Ser Ser Ser Leu Ser Val Leu Glu Gly Gln Ser
145                 150                 155                 160

Leu Arg Leu Val Cys Ala Val Asp Ser Asn Pro Pro Ala Arg Leu Ser
                165                 170                 175

Trp Thr Trp Arg Ser Leu Thr Leu Tyr Pro Ser Gln Pro Ser Asn Pro
            180                 185                 190

Leu Val Leu Glu Leu Gln Val His Leu Gly Asp Glu Gly Glu Phe Thr
        195                 200                 205

Cys Arg Ala Gln Asn Ser Leu Gly Ser Gln His Val Ser Leu Asn Leu
    210                 215                 220

Ser Leu Gln Gln Glu Tyr Thr Gly Lys Met Arg Pro Val Ser Gly Val
225                 230                 235                 240

Leu Leu Gly Ala Val Gly Gly Ala Gly Ala Thr Ala Leu Val Phe Leu
                245                 250                 255

Ser Phe Cys Val Ile Phe Ile Val Val Arg Ser Cys Arg Lys Lys Ser
            260                 265                 270

Ala Arg Pro Ala Ala Asp Val Gly Asp Ile Gly Met Lys Asp Ala Asn
        275                 280                 285

Thr Ile Arg Gly Ser Ala Leu Arg Val Thr
    290                 295

<210> SEQ ID NO 31
<211> LENGTH: 267
<212> TYPE: PRT
<213> ORGANISM: Homo sapiens

<400> SEQUENCE: 31

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr

```
            20                  25                  30
Cys Pro Pro Pro Met Ser Val Glu His Ala Asp Ile Trp Val Lys Ser
         35                  40                  45
Tyr Ser Leu Tyr Ser Arg Glu Arg Tyr Ile Cys Asn Ser Gly Phe Lys
     50                  55                  60
Arg Lys Ala Gly Thr Ser Ser Leu Thr Glu Cys Val Leu Asn Lys Ala
 65                  70                  75                  80
Thr Asn Val Ala His Trp Thr Thr Pro Ser Leu Lys Cys Ile Arg Asp
                 85                  90                  95
Pro Ala Leu Val His Gln Arg Pro Ala Pro Ser Thr Val Thr Thr
            100                 105                 110
Ala Gly Val Thr Pro Gln Pro Glu Ser Leu Ser Pro Ser Gly Lys Glu
            115                 120                 125
Pro Ala Ala Ser Ser Pro Ser Ser Asn Asn Thr Ala Ala Thr Thr Ala
        130                 135                 140
Ala Ile Val Pro Gly Ser Gln Leu Met Pro Ser Lys Ser Pro Ser Thr
145                 150                 155                 160
Gly Thr Thr Glu Ile Ser Ser His Glu Ser Ser His Gly Thr Pro Ser
                165                 170                 175
Gln Thr Thr Ala Lys Asn Trp Glu Leu Thr Ala Ser Ala Ser His Gln
            180                 185                 190
Pro Pro Gly Val Tyr Pro Gln Gly His Ser Asp Thr Thr Val Ala Ile
            195                 200                 205
Ser Thr Ser Thr Val Leu Leu Cys Gly Leu Ser Ala Val Ser Leu Leu
        210                 215                 220
Ala Cys Tyr Leu Lys Ser Arg Gln Thr Pro Pro Leu Ala Ser Val Glu
225                 230                 235                 240
Met Glu Ala Met Glu Ala Leu Pro Val Thr Trp Gly Thr Ser Ser Arg
                245                 250                 255
Asp Glu Asp Leu Glu Asn Cys Ser His His Leu
                260                 265

<210> SEQ ID NO 32
<211> LENGTH: 237
<212> TYPE: PRT
<213> ORGANISM: Homo sapiens

<400> SEQUENCE: 32

Ile Thr Cys Pro Pro Pro Met Ser Val Glu His Ala Asp Ile Trp Val
 1               5                  10                  15
Lys Ser Tyr Ser Leu Tyr Ser Arg Glu Arg Tyr Ile Cys Asn Ser Gly
                20                  25                  30
Phe Lys Arg Lys Ala Gly Thr Ser Ser Leu Thr Glu Cys Val Leu Asn
            35                  40                  45
Lys Ala Thr Asn Val Ala His Trp Thr Thr Pro Ser Leu Lys Cys Ile
        50                  55                  60
Arg Asp Pro Ala Leu Val His Gln Arg Pro Ala Pro Ser Thr Val
 65                  70                  75                  80
Thr Thr Ala Gly Val Thr Pro Gln Pro Glu Ser Leu Ser Pro Ser Gly
                 85                  90                  95
Lys Glu Pro Ala Ala Ser Ser Pro Ser Ser Asn Asn Thr Ala Ala Thr
            100                 105                 110
Thr Ala Ala Ile Val Pro Gly Ser Gln Leu Met Pro Ser Lys Ser Pro
            115                 120                 125
```

```
Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr Val
                165                 170                 175

Ala Ile Ser Thr Ser Thr Val Leu Leu Cys Gly Leu Ser Ala Val Ser
                180                 185                 190

Leu Leu Ala Cys Tyr Leu Lys Ser Arg Gln Thr Pro Pro Leu Ala Ser
            195                 200                 205

Val Glu Met Glu Ala Met Glu Ala Leu Pro Val Thr Trp Gly Thr Ser
210                 215                 220

Ser Arg Asp Glu Asp Leu Glu Asn Cys Ser His His Leu
225                 230                 235

<210> SEQ ID NO 33
<211> LENGTH: 224
<212> TYPE: PRT
<213> ORGANISM: Mus sp.

<400> SEQUENCE: 33

Met Ala Leu Leu Ile Ser Leu Pro Gly Gly Thr Pro Ala Met Ala Gln
1               5                   10                  15

Val Leu Leu Leu Ser Ser Gly Cys Leu His Ala Gly Asn Ser Glu
                20                  25                  30

Arg Tyr Asn Arg Lys Asn Gly Phe Gly Val Asn Gln Pro Glu Arg Cys
            35                  40                  45

Ser Gly Val Gln Gly Gly Ser Ile Asp Ile Pro Phe Ser Phe Tyr Phe
50                  55                  60

Pro Trp Lys Leu Ala Lys Asp Pro Gln Met Ser Ile Ala Trp Lys Trp
65                  70                  75                  80

Lys Asp Phe His Gly Glu Val Ile Tyr Asn Ser Ser Leu Pro Phe Ile
                85                  90                  95

His Glu His Phe Lys Gly Arg Leu Ile Leu Asn Trp Thr Gln Gly Gln
            100                 105                 110

Thr Ser Gly Val Leu Arg Ile Leu Asn Leu Lys Glu Ser Asp Gln Ala
            115                 120                 125

Gln Tyr Phe Ser Arg Val Asn Leu Gln Ser Thr Glu Gly Met Lys Leu
            130                 135                 140

Trp Gln Ser Ile Pro Gly Thr Gln Leu Asn Val Thr Gln Ala Leu Asn
145                 150                 155                 160

Thr Thr Met Arg Ser Pro Phe Ile Val Thr Ser Glu Phe Thr Thr Ala
                165                 170                 175

Gly Leu Glu His Thr Ser Asp Gln Arg Asn Pro Ser Leu Met Asn Leu
            180                 185                 190

Gly Ala Met Val Thr Met Leu Leu Ala Lys Val Leu Ile Val Leu
            195                 200                 205

Val Tyr Gly Trp Met Ile Phe Leu Arg Trp Lys Gln Arg Pro Ala His
210                 215                 220

<210> SEQ ID NO 34
<211> LENGTH: 196
<212> TYPE: PRT
<213> ORGANISM: Mus sp.

<400> SEQUENCE: 34
```

```
Gly Asn Ser Glu Arg Tyr Asn Arg Lys Asn Gly Phe Gly Val Asn Gln
1               5                   10                  15

Pro Glu Arg Cys Ser Gly Val Gln Gly Gly Ser Ile Asp Ile Pro Phe
            20                  25                  30

Ser Phe Tyr Phe Pro Trp Lys Leu Ala Lys Asp Pro Gln Met Ser Ile
        35                  40                  45

Ala Trp Lys Trp Lys Asp Phe His Gly Glu Val Ile Tyr Asn Ser Ser
50                  55                  60

Leu Pro Phe Ile His Glu His Phe Lys Gly Arg Leu Ile Leu Asn Trp
65                  70                  75                  80

Thr Gln Gly Gln Thr Ser Gly Val Leu Arg Ile Leu Asn Leu Lys Glu
                85                  90                  95

Ser Asp Gln Ala Gln Tyr Phe Ser Arg Val Asn Leu Gln Ser Thr Glu
            100                 105                 110

Gly Met Lys Leu Trp Gln Ser Ile Pro Gly Thr Gln Leu Asn Val Thr
        115                 120                 125

Gln Ala Leu Asn Thr Thr Met Arg Ser Pro Phe Ile Val Thr Ser Glu
130                 135                 140

Phe Thr Thr Ala Gly Leu Glu His Thr Ser Asp Gln Arg Asn Pro Ser
145                 150                 155                 160

Leu Met Asn Leu Gly Ala Met Val Thr Met Leu Leu Ala Lys Val Leu
                165                 170                 175

Val Ile Val Leu Val Tyr Gly Trp Met Ile Phe Leu Arg Trp Lys Gln
                180                 185                 190

Arg Pro Ala His
        195

<210> SEQ ID NO 35
<211> LENGTH: 227
<212> TYPE: PRT
<213> ORGANISM: Homo sapiens

<400> SEQUENCE: 35

Met Gly Arg Pro Leu Leu Leu Pro Leu Leu Leu Leu Gln Pro Pro
1               5                   10                  15

Ala Phe Leu Gln Pro Gly Gly Ser Thr Gly Ser Gly Pro Ser Tyr Leu
            20                  25                  30

Tyr Gly Val Thr Gln Pro Lys His Leu Ser Ala Ser Met Gly Gly Ser
        35                  40                  45

Val Glu Ile Pro Phe Ser Phe Tyr Tyr Pro Trp Glu Leu Ala Ile Val
50                  55                  60

Pro Asn Val Arg Ile Ser Trp Arg Arg Gly His Phe His Gly Gln Ser
65                  70                  75                  80

Phe Tyr Ser Thr Arg Pro Pro Ser Ile His Lys Asp Tyr Val Asn Arg
                85                  90                  95

Leu Phe Leu Asn Trp Thr Glu Gly Gln Glu Ser Gly Phe Leu Arg Ile
            100                 105                 110

Ser Asn Leu Arg Lys Glu Asp Gln Ser Val Tyr Phe Cys Arg Val Glu
        115                 120                 125

Leu Asp Thr Arg Arg Ser Gly Arg Gln Gln Leu Gln Ser Ile Lys Gly
130                 135                 140

Thr Lys Leu Thr Ile Thr Gln Ala Val Thr Thr Thr Thr Trp Arg
145                 150                 155                 160

Pro Ser Ser Thr Thr Thr Ile Ala Gly Leu Arg Val Thr Glu Ser Lys
                165                 170                 175
```

Gly His Ser Glu Ser Trp His Leu Ser Leu Asp Thr Ala Ile Arg Val
            180                 185                 190

Ala Leu Ala Val Ala Val Leu Lys Thr Val Ile Leu Gly Leu Leu Cys
        195                 200                 205

Leu Leu Leu Leu Trp Trp Arg Arg Lys Gly Ser Arg Ala Pro Ser
210                 215                 220

Ser Asp Phe
225

<210> SEQ ID NO 36
<211> LENGTH: 208
<212> TYPE: PRT
<213> ORGANISM: Homo sapiens

<400> SEQUENCE: 36

Gln Pro Gly Gly Ser Thr Gly Ser Gly Pro Ser Tyr Leu Tyr Gly Val
1               5                   10                  15

Thr Gln Pro Lys His Leu Ser Ala Ser Met Gly Gly Ser Val Glu Ile
            20                  25                  30

Pro Phe Ser Phe Tyr Tyr Pro Trp Glu Leu Ala Ile Val Pro Asn Val
        35                  40                  45

Arg Ile Ser Trp Arg Arg Gly His Phe His Gly Gln Ser Phe Tyr Ser
    50                  55                  60

Thr Arg Pro Pro Ser Ile His Lys Asp Tyr Val Asn Arg Leu Phe Leu
65                  70                  75                  80

Asn Trp Thr Glu Gly Gln Glu Ser Gly Phe Leu Arg Ile Ser Asn Leu
                85                  90                  95

Arg Lys Glu Asp Gln Ser Val Tyr Phe Cys Arg Val Glu Leu Asp Thr
            100                 105                 110

Arg Arg Ser Gly Arg Gln Gln Leu Gln Ser Ile Lys Gly Thr Lys Leu
        115                 120                 125

Thr Ile Thr Gln Ala Val Thr Thr Thr Thr Trp Arg Pro Ser Ser
    130                 135                 140

Thr Thr Thr Ile Ala Gly Leu Arg Val Thr Glu Ser Lys Gly His Ser
145                 150                 155                 160

Glu Ser Trp His Leu Ser Leu Asp Thr Ala Ile Arg Val Ala Leu Ala
                165                 170                 175

Val Ala Val Leu Lys Thr Val Ile Leu Gly Leu Leu Cys Leu Leu Leu
            180                 185                 190

Leu Trp Trp Arg Arg Arg Lys Gly Ser Arg Ala Pro Ser Ser Asp Phe
        195                 200                 205

<210> SEQ ID NO 37
<211> LENGTH: 5
<212> TYPE: PRT
<213> ORGANISM: Mus sp.

<400> SEQUENCE: 37

Pro Lys Ala Pro Thr
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic 8xHis tag

```
<400> SEQUENCE: 38

His His His His His His His
1               5

<210> SEQ ID NO 39
<211> LENGTH: 15
<212> TYPE: PRT
<213> ORGANISM: Mus sp.

<400> SEQUENCE: 39

Asn Met Lys Pro Thr Pro Lys Ala Pro Thr Pro Lys Lys Pro Ser
1               5                   10                  15

<210> SEQ ID NO 40
<211> LENGTH: 26
<212> TYPE: PRT
<213> ORGANISM: Homo sapiens

<400> SEQUENCE: 40

Ala Pro Asp Gly Gly Phe Leu Asp Leu Ser Asp Ala Leu Pro Asp Asn
1               5                   10                  15

Glu Asn Lys Lys Pro Thr Ala Ile Pro Lys
            20                  25

<210> SEQ ID NO 41
<211> LENGTH: 11
<212> TYPE: PRT
<213> ORGANISM: Homo sapiens

<400> SEQUENCE: 41

Gly Pro Thr Ile Lys Pro Cys Pro Pro Cys Lys
1               5                   10

<210> SEQ ID NO 42
<211> LENGTH: 9
<212> TYPE: PRT
<213> ORGANISM: Herpes simplex virus

<400> SEQUENCE: 42

Pro Pro Asn Pro Thr Pro Pro Pro
1               5

<210> SEQ ID NO 43
<211> LENGTH: 9
<212> TYPE: PRT
<213> ORGANISM: Herpes simplex virus

<400> SEQUENCE: 43

Gly Gly Pro Ala Thr Pro Ala Pro Pro
1               5

<210> SEQ ID NO 44
<211> LENGTH: 9
<212> TYPE: PRT
<213> ORGANISM: Mus sp.

<400> SEQUENCE: 44

Asn Met Lys Pro Thr Pro Lys Ala Pro
1               5

<210> SEQ ID NO 45
<211> LENGTH: 9
<212> TYPE: PRT
<213> ORGANISM: Mus sp.
```

<400> SEQUENCE: 45

Pro Lys Ala Pro Thr Pro Lys Lys Pro
1               5

<210> SEQ ID NO 46
<211> LENGTH: 6
<212> TYPE: PRT
<213> ORGANISM: Homo sapiens

<400> SEQUENCE: 46

Ala Ile Pro Lys Lys Pro
1               5

<210> SEQ ID NO 47
<211> LENGTH: 9
<212> TYPE: PRT
<213> ORGANISM: Homo sapiens

<400> SEQUENCE: 47

Pro Lys Ala Pro Thr Pro Lys Lys Pro
1               5

<210> SEQ ID NO 48
<211> LENGTH: 14
<212> TYPE: PRT
<213> ORGANISM: Mus sp.

<400> SEQUENCE: 48

Asn Met Lys Pro Thr Pro Lys Ala Pro Thr Pro Lys Lys Pro
1               5                   10

<210> SEQ ID NO 49
<211> LENGTH: 14
<212> TYPE: PRT
<213> ORGANISM: Homo sapiens

<400> SEQUENCE: 49

Asn Lys Lys Pro Thr Ala Ile Pro Lys Lys Pro Ser Ala Gly
1               5                   10

<210> SEQ ID NO 50
<211> LENGTH: 19
<212> TYPE: PRT
<213> ORGANISM: Artificial Sequence
<220> FEATURE:
<223> OTHER INFORMATION: Synthetic peptide

<400> SEQUENCE: 50

Asn Lys Lys Pro Thr Pro Lys Ala Pro Thr Ala Ile Pro Lys Lys Pro
1               5                   10                  15

Ser Ala Gly

<210> SEQ ID NO 51
<211> LENGTH: 120
<212> TYPE: PRT
<213> ORGANISM: Homo sapiens

<400> SEQUENCE: 51

Tyr Leu Tyr Gly Val Thr Gln Pro Lys His Leu Ser Ala Ser Met Gly
1               5                   10                  15

Gly Ser Val Glu Ile Pro Phe Ser Phe Tyr Tyr Pro Trp Glu Leu Ala
            20                  25                  30

```
Thr Ala Pro Asp Val Arg Ile Ser Trp Arg Arg Gly His Phe His Arg
         35                  40                  45

Gln Ser Phe Tyr Ser Thr Arg Pro Ser Ile His Lys Asp Tyr Val
 50                  55                  60

Asn Arg Leu Phe Leu Asn Trp Thr Glu Gly Gln Lys Ser Gly Phe Leu
 65                  70                  75                  80

Arg Ile Ser Asn Leu Gln Lys Gln Asp Gln Ser Val Tyr Phe Cys Arg
                 85                  90                  95

Val Glu Leu Asp Thr Arg Ser Ser Gly Arg Gln Gln Trp Gln Ser Ile
                100                 105                 110

Glu Gly Thr Lys Leu Ser Ile Thr
            115                 120

<210> SEQ ID NO 52
<211> LENGTH: 120
<212> TYPE: PRT
<213> ORGANISM: Pan sp.

<400> SEQUENCE: 52

Tyr Pro Tyr Gly Val Thr Gln Pro Lys His Leu Ser Ala Ser Met Gly
 1               5                  10                  15

Gly Ser Val Glu Ile Pro Phe Ser Phe Tyr Tyr Pro Trp Glu Leu Ala
                20                  25                  30

Thr Ala Pro Asp Val Arg Ile Ser Trp Arg Arg Gly His Phe His Gly
         35                  40                  45

Gln Ser Phe Tyr Ser Thr Arg Pro Ser Ile His Lys Asp Tyr Val
 50                  55                  60

Asn Arg Leu Phe Leu Asn Trp Thr Glu Gly Gln Lys Ser Gly Phe Leu
 65                  70                  75                  80

Arg Ile Ser Asn Leu Arg Lys Gln Asp Gln Ser Val Tyr Phe Cys Arg
                 85                  90                  95

Val Glu Leu Asp Thr Arg Ser Ser Gly Arg Gln Gln Trp Gln Ser Ile
                100                 105                 110

Glu Gly Thr Lys Leu Ser Ile Thr
            115                 120

<210> SEQ ID NO 53
<211> LENGTH: 120
<212> TYPE: PRT
<213> ORGANISM: Bos sp.

<400> SEQUENCE: 53

Gln His Tyr Glu Met Lys Gln Pro Arg Asp Leu Ser Ala Pro Glu Gly
 1               5                  10                  15

Gly Ser Ile Leu Ile Pro Phe Ser Phe Ser His Pro Gly Glu Leu Ala
                20                  25                  30

Lys Val Pro Asn Met Arg Ile Phe Trp Arg Trp Lys His Phe His Gly
         35                  40                  45

Glu Phe Ile Tyr Asn Thr Ser Pro Leu Phe Thr His Lys Asn Phe Lys
 50                  55                  60

Asn Arg Leu Ile Leu Asn Trp Lys Glu Pro Glu Lys Asn Gly Ser Leu
 65                  70                  75                  80

Gln Ile Ser Asn Leu Arg Arg Glu Asp Gln Ser Met Tyr Phe Cys Arg
                 85                  90                  95

Val Gln Leu Asp Thr Leu Arg Asp Gly Lys Gln Lys Trp Gln Ser Ile
                100                 105                 110
```

```
Glu Gly Thr Lys Leu Thr Ile Thr
        115                 120
```

<210> SEQ ID NO 54
<211> LENGTH: 120
<212> TYPE: PRT
<213> ORGANISM: Canis sp.

<400> SEQUENCE: 54

```
Met Asp Phe Arg Met Asp Gln Pro Glu His Leu Ser Ala Pro Lys Gly
1               5                   10                  15

Gly Thr Val His Ile Asn Phe Thr Phe Tyr Tyr Cys Gly Ala Leu Ala
            20                  25                  30

Lys Asp Pro Arg Val Ser Ile Ala Leu Lys Arg Thr His Phe His Gly
        35                  40                  45

Glu Val Ile Tyr Asn Ser Thr Arg His Phe Val His Glu Asp Tyr Lys
    50                  55                  60

Asp Arg Ile Ile Leu Asn Leu Pro Glu Gly Gln Lys Ser Gly Phe Leu
65                  70                  75                  80

Gln Ile Leu Asn Leu Arg Glu Glu Asp Glu Asn Met Tyr Phe Cys Arg
                85                  90                  95

Val Gln Leu Lys Thr Gln Arg Phe Gly Leu Gln Val Trp Gln Ser Ile
            100                 105                 110

Leu Gly Thr Lys Leu Thr Ile Asn
        115                 120
```

<210> SEQ ID NO 55
<211> LENGTH: 119
<212> TYPE: PRT
<213> ORGANISM: Rattus sp.

<400> SEQUENCE: 55

```
Tyr Asp Tyr Gly Val Asp Gln Pro Ala Val Leu Ser Gly Val Gln Gly
1               5                   10                  15

Ser Ser Ile Glu Ile Pro Phe Ser Phe Tyr Phe Pro Trp Asn Leu Thr
            20                  25                  30

Lys Asp Pro Gln Met Ser Ile Ala Trp Arg Trp Lys Asn Phe His Gly
        35                  40                  45

Glu Phe Ile Tyr Asn Ser Thr Gln Pro Phe Ile His Glu His Phe Lys
    50                  55                  60

Asp Arg Leu Ile Met Asn Trp Thr Gln Gly Gln Thr Ser Gly Val Leu
65                  70                  75                  80

Arg Ile Leu Asn Phe Lys Lys Asn Asp Gln Ala Thr Tyr Phe Gly Arg
                85                  90                  95

Val Leu Leu Gln Thr Thr Glu Gly Met Lys Val Trp Gln Ser Ile Pro
            100                 105                 110

Gly Thr Asn Leu Thr Val Thr
        115
```

<210> SEQ ID NO 56
<211> LENGTH: 119
<212> TYPE: PRT
<213> ORGANISM: Mus sp.

<400> SEQUENCE: 56

```
Asn Gly Phe Gly Val Asn Gln Pro Glu Ser Cys Ser Gly Val Gln Gly
1               5                   10                  15

Gly Ser Ile Asp Ile Pro Phe Ser Phe Tyr Phe Pro Trp Lys Leu Ala
```

```
            20                  25                  30
Lys Asp Pro Gln Met Ser Ile Ala Trp Arg Trp Lys Asp Phe His Gly
        35                  40                  45

Glu Phe Ile Tyr Asn Ser Ser Leu Pro Phe Ile His Glu His Phe Lys
    50                  55                  60

Gly Arg Leu Ile Leu Asn Trp Thr Gln Gly Gln Thr Ser Gly Val Leu
65                  70                  75                  80

Arg Ile Leu Asn Leu Lys Glu Ser Asp Gln Thr Arg Tyr Phe Gly Arg
                85                  90                  95

Val Phe Leu Gln Thr Thr Glu Gly Ile Gln Phe Trp Gln Ser Ile Pro
            100                 105                 110

Gly Thr Gln Leu Asn Val Thr
            115

<210> SEQ ID NO 57
<211> LENGTH: 120
<212> TYPE: PRT
<213> ORGANISM: Homo sapiens

<400> SEQUENCE: 57

Tyr Leu Tyr Gly Val Thr Gln Pro Lys His Leu Ser Ala Ser Met Gly
1               5                   10                  15

Gly Ser Val Glu Ile Pro Phe Ser Phe Tyr Tyr Pro Trp Glu Leu Ala
            20                  25                  30

Ile Val Pro Asn Val Arg Ile Ser Trp Arg Arg Gly His Phe His Gly
        35                  40                  45

Gln Ser Phe Tyr Ser Thr Arg Pro Pro Ser Ile His Lys Asp Tyr Val
    50                  55                  60

Asn Arg Leu Phe Leu Asn Trp Thr Glu Gly Gln Glu Ser Gly Phe Leu
65                  70                  75                  80

Arg Ile Ser Asn Leu Arg Lys Glu Asp Gln Ser Val Tyr Phe Cys Arg
                85                  90                  95

Val Glu Leu Asp Thr Arg Arg Ser Gly Arg Gln Gln Leu Gln Ser Ile
            100                 105                 110

Lys Gly Thr Lys Leu Thr Ile Thr
        115                 120

<210> SEQ ID NO 58
<211> LENGTH: 119
<212> TYPE: PRT
<213> ORGANISM: Mus sp.

<400> SEQUENCE: 58

Asn Gly Phe Gly Val Asn Gln Pro Glu Arg Cys Ser Gly Val Gln Gly
1               5                   10                  15

Gly Ser Ile Asp Ile Pro Phe Ser Phe Tyr Phe Pro Trp Lys Leu Ala
            20                  25                  30

Lys Asp Pro Gln Met Ser Ile Ala Trp Lys Trp Lys Asp Phe His Gly
        35                  40                  45

Glu Val Ile Tyr Asn Ser Ser Leu Pro Phe Ile His Glu His Phe Lys
    50                  55                  60

Gly Arg Leu Ile Leu Asn Trp Thr Gln Gly Gln Thr Ser Gly Val Leu
65                  70                  75                  80

Arg Ile Leu Asn Leu Lys Glu Ser Asp Gln Ala Gln Tyr Phe Ser Arg
                85                  90                  95

Val Asn Leu Gln Ser Thr Glu Gly Met Lys Leu Trp Gln Ser Ile Pro
```

-continued

```
                    100                 105                 110

Gly Thr Gln Leu Asn Val Thr
        115

<210> SEQ ID NO 59
<211> LENGTH: 118
<212> TYPE: PRT
<213> ORGANISM: Homo sapiens

<400> SEQUENCE: 59

Ala Ser Trp Gly Val Ser Ser Pro Gln Asp Val Gln Gly Val Lys Gly
1               5                   10                  15

Ser Cys Leu Leu Ile Pro Cys Ile Phe Ser Phe Pro Ala Asp Val Glu
            20                  25                  30

Val Pro Asp Gly Ile Thr Ala Ile Trp Tyr Tyr Asp Tyr Ser Gly Gln
        35                  40                  45

Arg Gln Val Val Ser His Ser Ala Asp Pro Lys Leu Val Glu Ala Arg
    50                  55                  60

Phe Arg Gly Arg Thr Glu Phe Met Gly Asn Pro Glu His Arg Val Cys
65                  70                  75                  80

Asn Leu Leu Leu Lys Asp Leu Gln Pro Glu Asp Ser Gly Ser Tyr Asn
                85                  90                  95

Phe Arg Phe Glu Ile Ser Glu Val Asn Arg Trp Ser Asp Val Lys Gly
            100                 105                 110

Thr Leu Val Thr Val Thr
        115

<210> SEQ ID NO 60
<211> LENGTH: 118
<212> TYPE: PRT
<213> ORGANISM: Mus sp.

<400> SEQUENCE: 60

Thr Thr Trp Gly Val Ser Ser Pro Lys Asn Val Gln Gly Leu Ser Gly
1               5                   10                  15

Ser Cys Leu Leu Ile Pro Cys Ile Phe Ser Tyr Pro Ala Asp Val Pro
            20                  25                  30

Val Ser Asn Gly Ile Thr Ala Ile Trp Tyr Tyr Asp Tyr Ser Gly Lys
        35                  40                  45

Arg Gln Val Val Ile His Ser Gly Asp Pro Lys Leu Val Asp Lys Arg
    50                  55                  60

Phe Arg Gly Arg Ala Glu Leu Met Gly Asn Met Asp His Lys Val Cys
65                  70                  75                  80

Asn Leu Leu Leu Lys Asp Leu Lys Pro Glu Asp Ser Gly Thr Tyr Asn
                85                  90                  95

Phe Arg Phe Glu Ile Ser Asp Ser Asn Arg Trp Leu Asp Val Lys Gly
            100                 105                 110

Thr Thr Val Thr Val Thr
        115

<210> SEQ ID NO 61
<211> LENGTH: 230
<212> TYPE: PRT
<213> ORGANISM: Homo sapiens

<400> SEQUENCE: 61

Met Gly Arg Pro Leu Leu Leu Pro Leu Leu Pro Leu Leu Leu Pro Pro
1               5                   10                  15
```

```
Ala Phe Leu Gln Pro Ser Gly Ser Thr Gly Ser Gly Pro Ser Tyr Leu
            20                  25                  30

Tyr Gly Val Thr Gln Pro Lys His Leu Ser Ala Ser Met Gly Gly Ser
        35                  40                  45

Val Glu Ile Pro Phe Ser Phe Tyr Tyr Pro Trp Glu Leu Ala Thr Ala
 50                  55                  60

Pro Asp Val Arg Ile Ser Trp Arg Arg Gly His Phe His Arg Gln Ser
 65                  70                  75                  80

Phe Tyr Ser Thr Arg Pro Pro Ser Ile His Lys Asp Tyr Val Asn Arg
                85                  90                  95

Leu Phe Leu Asn Trp Thr Glu Gly Gln Lys Ser Gly Phe Leu Arg Ile
            100                 105                 110

Ser Asn Leu Gln Lys Gln Asp Gln Ser Val Tyr Phe Cys Arg Val Glu
            115                 120                 125

Leu Asp Thr Arg Ser Ser Gly Arg Gln Gln Trp Gln Ser Ile Glu Gly
130                 135                 140

Thr Lys Leu Ser Ile Thr Gln Gly Gln Gln Arg Thr Lys Ala Thr Thr
145                 150                 155                 160

Pro Ala Arg Glu Pro Phe Gln Asn Thr Glu Glu Pro Tyr Glu Asn Ile
                165                 170                 175

Arg Asn Glu Gly Gln Asn Thr Asp Pro Lys Leu Asn Pro Lys Asp Asp
            180                 185                 190

Gly Ile Val Tyr Ala Ser Leu Ala Leu Ser Ser Ser Thr Ser Pro Arg
            195                 200                 205

Ala Pro Pro Ser His Arg Pro Leu Lys Ser Pro Gln Asn Glu Thr Leu
            210                 215                 220

Tyr Ser Val Leu Lys Ala
225                 230

<210> SEQ ID NO 62
<211> LENGTH: 226
<212> TYPE: PRT
<213> ORGANISM: Homo sapiens

<400> SEQUENCE: 62

Met Gly Arg Pro Leu Leu Leu Pro Leu Leu Pro Leu Leu Leu Pro Pro
 1               5                  10                  15

Ala Phe Leu Gln Pro Ser Gly Ser Thr Gly Ser Gly Pro Ser Tyr Leu
            20                  25                  30

Tyr Gly Val Thr Gln Pro Lys His Leu Ser Ala Ser Met Gly Gly Ser
        35                  40                  45

Val Glu Ile Pro Phe Ser Phe Tyr Tyr Pro Trp Glu Leu Ala Thr Ala
 50                  55                  60

Pro Asp Val Arg Ile Ser Trp Arg Arg Gly His Phe His Gly Gln Ser
 65                  70                  75                  80

Phe Tyr Ser Thr Arg Pro Pro Ser Ile His Lys Asp Tyr Val Asn Arg
                85                  90                  95

Leu Phe Leu Asn Trp Thr Glu Gly Gln Lys Ser Gly Phe Leu Arg Ile
            100                 105                 110

Ser Asn Leu Gln Lys Gln Asp Gln Ser Val Tyr Phe Cys Arg Val Glu
            115                 120                 125

Leu Asp Thr Arg Ser Ser Gly Arg Gln Gln Trp Gln Ser Ile Glu Gly
130                 135                 140

Thr Lys Leu Ser Ile Thr Gln Gly Gln Gln Arg Thr Lys Ala Thr Thr
```

```
                145                 150                 155                 160
Pro Ala Arg Glu Pro Phe Gln Asn Thr Glu Glu Pro Tyr Glu Asn Ile
                    165                 170                 175

Arg Asn Glu Gly Gln Asn Thr Asp Pro Lys Leu Asn Pro Lys Leu His
                180                 185                 190

Leu Thr Gln Ser Thr Ser Gln Pro Ser Pro Gln Glu Pro Pro Glu
                195                 200                 205

Arg Asp Pro Val Leu Cys Leu Lys Gly Leu Thr Asn Gly Gln Pro Ser
210                 215                 220

Gln Asp
225

<210> SEQ ID NO 63
<211> LENGTH: 175
<212> TYPE: PRT
<213> ORGANISM: Homo sapiens

<400> SEQUENCE: 63

Met Gly Arg Pro Leu Leu Pro Leu Leu Pro Leu Leu Leu Pro Pro
1               5                   10                  15

Ala Phe Leu Gln Pro Ser Gly Ser Thr Gly Ser Gly Pro Ser Tyr Leu
                20                  25                  30

Tyr Gly Val Thr Gln Pro Lys His Leu Ser Ala Ser Met Gly Gly Ser
            35                  40                  45

Val Glu Ile Pro Phe Ser Phe Tyr Tyr Pro Trp Glu Leu Ala Thr Ala
        50                  55                  60

Pro Asp Val Arg Ile Ser Trp Arg Arg Gly His Phe His Arg Gln Ser
65                  70                  75                  80

Phe Tyr Ser Thr Arg Pro Pro Ser Ile His Lys Asp Tyr Val Asn Arg
                85                  90                  95

Leu Phe Leu Asn Trp Thr Glu Gly Gln Lys Ser Gly Phe Leu Arg Ile
                100                 105                 110

Ser Asn Leu Gln Lys Gln Asp Gln Ser Val Tyr Phe Cys Arg Val Glu
            115                 120                 125

Leu Asp Thr Arg Ser Ser Gly Arg Gln Gln Trp Gln Ser Ile Glu Gly
        130                 135                 140

Thr Lys Leu Ser Ile Thr Gln Gly Asn Pro Ser Lys Thr Gln Arg Ser
145                 150                 155                 160

His Met Arg Ile Ser Gly Met Lys Asp Lys Ile Gln Ile Pro Ser
                165                 170                 175

<210> SEQ ID NO 64
<211> LENGTH: 15
<212> TYPE: PRT
<213> ORGANISM: Homo sapiens

<400> SEQUENCE: 64

Asn Met Lys Pro Thr Pro Lys Ala Pro Thr Pro Lys Lys Pro Ser
1               5                   10                  15

<210> SEQ ID NO 65
<211> LENGTH: 26
<212> TYPE: PRT
<213> ORGANISM: Homo sapiens

<400> SEQUENCE: 65

Ala Pro Asp Gly Gly Phe Leu Asp Leu Ser Asp Ala Leu Pro Asp Asn
1               5                   10                  15
```

Glu Asn Lys Lys Pro Thr Ala Ile Pro Lys
            20                  25

<210> SEQ ID NO 66
<211> LENGTH: 11
<212> TYPE: PRT
<213> ORGANISM: Homo sapiens

<400> SEQUENCE: 66

Gly Pro Thr Ile Lys Pro Cys Pro Pro Cys Lys
1               5                   10

<210> SEQ ID NO 67
<211> LENGTH: 9
<212> TYPE: PRT
<213> ORGANISM: Homo sapiens

<400> SEQUENCE: 67

Pro Pro Asn Pro Thr Pro Pro Pro Pro
1               5

<210> SEQ ID NO 68
<211> LENGTH: 9
<212> TYPE: PRT
<213> ORGANISM: Homo sapiens

<400> SEQUENCE: 68

Gly Gly Pro Ala Thr Pro Ala Pro Pro
1               5

<210> SEQ ID NO 69
<211> LENGTH: 9
<212> TYPE: PRT
<213> ORGANISM: Mus sp.

<400> SEQUENCE: 69

Asn Met Lys Pro Thr Pro Lys Ala Pro
1               5

<210> SEQ ID NO 70
<211> LENGTH: 9
<212> TYPE: PRT
<213> ORGANISM: Mus sp.

<400> SEQUENCE: 70

Pro Lys Ala Pro Thr Pro Lys Lys Pro
1               5

<210> SEQ ID NO 71
<211> LENGTH: 6
<212> TYPE: PRT
<213> ORGANISM: Homo sapiens

<400> SEQUENCE: 71

Ala Ile Pro Lys Lys Pro
1               5

<210> SEQ ID NO 72
<211> LENGTH: 9
<212> TYPE: PRT
<213> ORGANISM: Homo sapiens

<400> SEQUENCE: 72

Pro Lys Ala Pro Thr Pro Lys Lys Pro

```
<210> SEQ ID NO 73
<211> LENGTH: 120
<212> TYPE: PRT
<213> ORGANISM: Homo sapiens

<400> SEQUENCE: 73

Tyr Leu Tyr Gly Val Thr Gln Pro Lys His Leu Ser Ala Ser Met Gly
1               5                   10                  15

Gly Ser Val Glu Ile Pro Phe Ser Phe Tyr Tyr Pro Trp Glu Leu Ala
            20                  25                  30

Thr Ala Pro Asp Val Arg Ile Ser Trp Arg Arg Gly His Phe His Arg
        35                  40                  45

Gln Ser Phe Tyr Ser Thr Arg Pro Pro Ser Ile His Lys Asp Tyr Val
    50                  55                  60

Asn Arg Leu Phe Leu Asn Trp Thr Glu Gly Gln Lys Ser Gly Phe Leu
65                  70                  75                  80

Arg Ile Ser Asn Leu Gln Lys Gln Asp Gln Ser Val Tyr Phe Cys Arg
                85                  90                  95

Val Glu Leu Asp Thr Arg Ser Ser Gly Arg Gln Gln Trp Gln Ser Ile
            100                 105                 110

Glu Gly Thr Lys Leu Ser Ile Thr
        115                 120

<210> SEQ ID NO 74
<211> LENGTH: 120
<212> TYPE: PRT
<213> ORGANISM: Pan troglodytes

<400> SEQUENCE: 74

Tyr Pro Tyr Gly Val Thr Gln Pro Lys His Leu Ser Ala Ser Met Gly
1               5                   10                  15

Gly Ser Val Glu Ile Pro Phe Ser Phe Tyr Tyr Pro Trp Glu Leu Ala
            20                  25                  30

Thr Ala Pro Asp Val Arg Ile Ser Trp Arg Arg Gly His Phe His Gly
        35                  40                  45

Gln Ser Phe Tyr Ser Thr Arg Pro Pro Ser Ile His Lys Asp Tyr Val
    50                  55                  60

Asn Arg Leu Phe Leu Asn Trp Thr Glu Gly Gln Lys Ser Gly Phe Leu
65                  70                  75                  80

Arg Ile Ser Asn Leu Arg Lys Gln Asp Gln Ser Val Tyr Phe Cys Arg
                85                  90                  95

Val Glu Leu Asp Thr Arg Ser Ser Gly Arg Gln Gln Trp Gln Ser Ile
            100                 105                 110

Glu Gly Thr Lys Leu Ser Ile Thr
        115                 120

<210> SEQ ID NO 75
<211> LENGTH: 120
<212> TYPE: PRT
<213> ORGANISM: Bos taurus

<400> SEQUENCE: 75

Gln His Tyr Glu Met Lys Gln Pro Arg Asp Leu Ser Ala Pro Glu Gly
1               5                   10                  15

Gly Ser Ile Leu Ile Pro Phe Ser Phe Ser His Pro Gly Glu Leu Ala
            20                  25                  30
```

```
Lys Val Pro Asn Met Arg Ile Phe Trp Arg Trp Lys His Phe His Gly
            35                  40                  45

Glu Phe Ile Tyr Asn Thr Ser Pro Leu Phe Thr His Lys Asn Phe Lys
        50                  55                  60

Asn Arg Leu Ile Leu Asn Trp Lys Glu Pro Glu Lys Asn Gly Ser Leu
 65                  70                  75                  80

Gln Ile Ser Asn Leu Arg Arg Glu Asp Gln Ser Met Tyr Phe Cys Arg
                85                  90                  95

Val Gln Leu Asp Thr Leu Arg Asp Gly Lys Gln Lys Trp Gln Ser Ile
            100                 105                 110

Glu Gly Thr Lys Leu Thr Ile Thr
            115                 120

<210> SEQ ID NO 76
<211> LENGTH: 120
<212> TYPE: PRT
<213> ORGANISM: Canis familiaris

<400> SEQUENCE: 76

Met Asp Phe Arg Met Asp Gln Pro Glu His Leu Ser Ala Pro Lys Gly
  1               5                  10                  15

Gly Thr Val His Ile Asn Phe Thr Phe Tyr Tyr Cys Gly Ala Leu Ala
             20                  25                  30

Lys Asp Pro Arg Val Ser Ile Ala Leu Lys Arg Thr His Phe His Gly
            35                  40                  45

Glu Val Ile Tyr Asn Ser Thr Arg His Phe Val His Glu Asp Tyr Lys
        50                  55                  60

Asp Arg Ile Ile Leu Asn Leu Pro Glu Gly Gln Lys Ser Gly Phe Leu
 65                  70                  75                  80

Gln Ile Leu Asn Leu Arg Glu Glu Asp Glu Asn Met Tyr Phe Cys Arg
                85                  90                  95

Val Gln Leu Lys Thr Gln Arg Phe Gly Leu Gln Val Trp Gln Ser Ile
            100                 105                 110

Leu Gly Thr Lys Leu Thr Ile Asn
            115                 120

<210> SEQ ID NO 77
<211> LENGTH: 119
<212> TYPE: PRT
<213> ORGANISM: Rattus sp.

<400> SEQUENCE: 77

Tyr Asp Tyr Gly Val Asp Gln Pro Ala Val Leu Ser Gly Val Gln Gly
  1               5                  10                  15

Ser Ser Ile Glu Ile Pro Phe Ser Phe Tyr Phe Pro Trp Asn Leu Thr
             20                  25                  30

Lys Asp Pro Gln Met Ser Ile Ala Trp Arg Trp Lys Asn Phe His Gly
            35                  40                  45

Glu Phe Ile Tyr Asn Ser Thr Gln Pro Phe Ile His Glu His Phe Lys
        50                  55                  60

Asp Arg Leu Ile Met Asn Trp Thr Gln Gly Thr Ser Gly Val Leu
 65                  70                  75                  80

Arg Ile Leu Asn Phe Lys Lys Asn Asp Gln Ala Thr Tyr Phe Gly Arg
                85                  90                  95

Val Leu Leu Gln Thr Thr Glu Gly Met Lys Val Trp Gln Ser Ile Pro
            100                 105                 110
```

Gly Thr Asn Leu Thr Val Thr
        115

<210> SEQ ID NO 78
<211> LENGTH: 119
<212> TYPE: PRT
<213> ORGANISM: Mus sp.

<400> SEQUENCE: 78

Asn Gly Phe Gly Val Asn Gln Pro Glu Ser Cys Ser Gly Val Gln Gly
1               5                   10                  15

Gly Ser Ile Asp Ile Pro Phe Ser Phe Tyr Phe Pro Trp Lys Leu Ala
            20                  25                  30

Lys Asp Pro Gln Met Ser Ile Ala Trp Arg Trp Lys Asp Phe His Gly
        35                  40                  45

Glu Phe Ile Tyr Asn Ser Ser Leu Pro Phe Ile His Glu His Phe Lys
    50                  55                  60

Gly Arg Leu Ile Leu Asn Trp Thr Gln Gly Gln Thr Ser Gly Val Leu
65                  70                  75                  80

Arg Ile Leu Asn Leu Lys Glu Ser Asp Gln Thr Arg Tyr Phe Gly Arg
                85                  90                  95

Val Phe Leu Gln Thr Thr Glu Gly Ile Gln Phe Trp Gln Ser Ile Pro
            100                 105                 110

Gly Thr Gln Leu Asn Val Thr
        115

<210> SEQ ID NO 79
<211> LENGTH: 120
<212> TYPE: PRT
<213> ORGANISM: Homo sapiens

<400> SEQUENCE: 79

Tyr Leu Tyr Gly Val Thr Gln Pro Lys His Leu Ser Ala Ser Met Gly
1               5                   10                  15

Gly Ser Val Glu Ile Pro Phe Ser Phe Tyr Tyr Pro Trp Glu Leu Ala
            20                  25                  30

Ile Val Pro Asn Val Arg Ile Ser Trp Arg Arg Gly His Phe His Gly
        35                  40                  45

Gln Ser Phe Tyr Ser Thr Arg Pro Pro Ser Ile His Lys Asp Tyr Val
    50                  55                  60

Asn Arg Leu Phe Leu Asn Trp Thr Glu Gly Gln Glu Ser Gly Phe Leu
65                  70                  75                  80

Arg Ile Ser Asn Leu Arg Lys Glu Asp Gln Ser Val Tyr Phe Cys Arg
                85                  90                  95

Val Glu Leu Asp Thr Arg Arg Ser Gly Arg Gln Gln Leu Gln Ser Ile
            100                 105                 110

Lys Gly Thr Lys Leu Thr Ile Thr
        115                 120

<210> SEQ ID NO 80
<211> LENGTH: 119
<212> TYPE: PRT
<213> ORGANISM: Mus sp.

<400> SEQUENCE: 80

Asn Gly Phe Gly Val Asn Gln Pro Glu Arg Cys Ser Gly Val Gln Gly
1               5                   10                  15

-continued

Gly Ser Ile Asp Ile Pro Phe Ser Phe Tyr Phe Pro Trp Lys Leu Ala
            20                  25                  30

Lys Asp Pro Gln Met Ser Ile Ala Trp Lys Trp Lys Asp Phe His Gly
        35                  40                  45

Glu Val Ile Tyr Asn Ser Ser Leu Pro Phe Ile His Glu His Phe Lys
 50                  55                  60

Gly Arg Leu Ile Leu Asn Trp Thr Gln Gly Gln Thr Ser Gly Val Leu
 65                  70                  75                  80

Arg Ile Leu Asn Leu Lys Glu Ser Asp Gln Ala Gln Tyr Phe Ser Arg
                85                  90                  95

Val Asn Leu Gln Ser Thr Glu Gly Met Lys Leu Trp Gln Ser Ile Pro
            100                 105                 110

Gly Thr Gln Leu Asn Val Thr
        115

<210> SEQ ID NO 81
<211> LENGTH: 118
<212> TYPE: PRT
<213> ORGANISM: Homo sapiens

<400> SEQUENCE: 81

Ala Ser Trp Gly Val Ser Ser Pro Gln Asp Val Gln Gly Val Lys Gly
 1               5                  10                  15

Ser Cys Leu Leu Ile Pro Cys Ile Phe Ser Phe Pro Ala Asp Val Glu
            20                  25                  30

Val Pro Asp Gly Ile Thr Ala Ile Trp Tyr Tyr Asp Tyr Ser Gly Gln
        35                  40                  45

Arg Gln Val Val Ser His Ser Ala Asp Pro Lys Leu Val Glu Ala Arg
 50                  55                  60

Phe Arg Gly Arg Thr Glu Phe Met Gly Asn Pro Glu His Arg Val Cys
 65                  70                  75                  80

Asn Leu Leu Leu Lys Asp Leu Gln Pro Glu Asp Ser Gly Ser Tyr Asn
                85                  90                  95

Phe Arg Phe Glu Ile Ser Glu Val Asn Arg Trp Ser Asp Val Lys Gly
            100                 105                 110

Thr Leu Val Thr Val Thr
        115

<210> SEQ ID NO 82
<211> LENGTH: 118
<212> TYPE: PRT
<213> ORGANISM: Mus sp.

<400> SEQUENCE: 82

Thr Thr Trp Gly Val Ser Ser Pro Lys Asn Val Gln Gly Leu Ser Gly
 1               5                  10                  15

Ser Cys Leu Leu Ile Pro Cys Ile Phe Ser Tyr Pro Ala Asp Val Pro
            20                  25                  30

Val Ser Asn Gly Ile Thr Ala Ile Trp Tyr Tyr Asp Tyr Ser Gly Lys
        35                  40                  45

Arg Gln Val Val Ile His Ser Gly Asp Pro Lys Leu Val Asp Lys Arg
 50                  55                  60

Phe Arg Gly Arg Ala Glu Leu Met Gly Asn Met Asp His Lys Val Cys
 65                  70                  75                  80

Asn Leu Leu Leu Lys Asp Leu Lys Pro Glu Asp Ser Gly Thr Tyr Asn
                85                  90                  95

Phe Arg Phe Glu Ile Ser Asp Ser Asn Arg Trp Leu Asp Val Lys Gly
            100                 105                 110

Thr Thr Val Thr Val Thr
        115

<210> SEQ ID NO 83
<211> LENGTH: 303
<212> TYPE: PRT
<213> ORGANISM: Homo sapiens

<400> SEQUENCE: 83

Met Gly Arg Pro Leu Leu Leu Pro Leu Leu Pro Leu Leu Leu Pro Pro
1               5                   10                  15

Ala Phe Leu Gln Pro Ser Gly Ser Thr Gly Ser Gly Pro Ser Tyr Leu
            20                  25                  30

Tyr Gly Val Thr Gln Pro Lys His Leu Ser Ala Ser Met Gly Gly Ser
        35                  40                  45

Val Glu Ile Pro Phe Ser Phe Tyr Tyr Pro Trp Glu Leu Ala Thr Ala
    50                  55                  60

Pro Asp Val Arg Ile Ser Trp Arg Arg Gly His Phe His Arg Gln Ser
65                  70                  75                  80

Phe Tyr Ser Thr Arg Pro Pro Ser Ile His Lys Asp Tyr Val Asn Arg
                85                  90                  95

Leu Phe Leu Asn Trp Thr Glu Gly Gln Lys Ser Gly Phe Leu Arg Ile
            100                 105                 110

Ser Asn Leu Gln Lys Gln Asp Gln Ser Val Tyr Phe Cys Arg Val Glu
        115                 120                 125

Leu Asp Thr Arg Ser Ser Gly Arg Gln Gln Trp Gln Ser Ile Glu Gly
    130                 135                 140

Thr Lys Leu Ser Ile Thr Gln Ala Val Thr Thr Thr Thr Gln Arg Pro
145                 150                 155                 160

Ser Ser Met Thr Thr Thr Trp Arg Leu Ser Ser Thr Thr Thr Thr Thr
                165                 170                 175

Gly Leu Arg Val Thr Gln Gly Lys Arg Arg Ser Asp Ser Trp His Ile
            180                 185                 190

Ser Leu Glu Thr Ala Val Gly Val Gln Ala Val Thr Thr Thr Thr Gln
        195                 200                 205

Arg Pro Ser Ser Met Thr Thr Thr Trp Arg Leu Ser Ser Thr Thr Thr
    210                 215                 220

Thr Thr Gly Leu Arg Val Thr Gln Gly Lys Arg Arg Ser Asp Ser Trp
225                 230                 235                 240

His Ile Ser Leu Glu Thr Ala Val Gly Val Asn Glu Gly Gln Asn Thr
                245                 250                 255

Asp Pro Lys Leu Asn Pro Lys Asp Gly Ile Val Tyr Ala Ser Leu
            260                 265                 270

Ala Leu Ser Ser Thr Ser Pro Arg Ala Pro Pro Ser His Arg Pro
        275                 280                 285

Leu Lys Ser Pro Gln Asn Glu Thr Leu Tyr Ser Val Leu Lys Ala
    290                 295                 300

<210> SEQ ID NO 84
<211> LENGTH: 230
<212> TYPE: PRT
<213> ORGANISM: Homo sapiens

<400> SEQUENCE: 84

```
Met Gly Arg Pro Leu Leu Leu Pro Leu Leu Leu Pro Pro
1               5                   10                  15

Ala Phe Leu Gln Pro Ser Gly Ser Gly Pro Ser Tyr Leu
                20                  25                  30

Tyr Gly Val Thr Gln Pro Lys His Leu Ser Ala Ser Met Gly Gly Ser
                35                  40                  45

Val Glu Ile Pro Phe Ser Phe Tyr Tyr Pro Trp Glu Leu Ala Thr Ala
50                      55                      60

Pro Asp Val Arg Ile Ser Trp Arg Arg Gly His Phe His Arg Gln Ser
65                      70                      75                      80

Phe Tyr Ser Thr Arg Pro Pro Ser Ile His Lys Asp Tyr Val Asn Arg
                85                      90                      95

Leu Phe Leu Asn Trp Thr Glu Gly Gln Lys Ser Gly Phe Leu Arg Ile
                100                     105                     110

Ser Asn Leu Gln Lys Gln Asp Gln Ser Val Tyr Phe Cys Arg Val Glu
                115                     120                     125

Leu Asp Thr Arg Ser Ser Gly Arg Gln Gln Trp Gln Ser Ile Glu Gly
                130                     135                     140

Thr Lys Leu Ser Ile Thr Gln Gly Gln Gln Arg Thr Lys Ala Thr Thr
145                     150                     155                     160

Pro Ala Arg Glu Pro Phe Gln Asn Thr Glu Glu Pro Tyr Glu Asn Ile
                165                     170                     175

Arg Asn Glu Gly Gln Asn Thr Asp Pro Lys Leu Asn Pro Lys Asp Asp
                180                     185                     190

Gly Ile Val Tyr Ala Ser Leu Ala Leu Ser Ser Ser Thr Ser Pro Arg
                195                     200                     205

Ala Pro Pro Ser His Arg Pro Leu Lys Ser Pro Gln Asn Glu Thr Leu
210                     215                     220

Tyr Ser Val Leu Lys Ala
225                     230

<210> SEQ ID NO 85
<211> LENGTH: 226
<212> TYPE: PRT
<213> ORGANISM: Homo sapiens

<400> SEQUENCE: 85

Met Gly Arg Pro Leu Leu Leu Pro Leu Leu Leu Pro Pro
1               5                   10                  15

Ala Phe Leu Gln Pro Ser Gly Ser Gly Pro Ser Tyr Leu
                20                  25                  30

Tyr Gly Val Thr Gln Pro Lys His Leu Ser Ala Ser Met Gly Gly Ser
                35                  40                  45

Val Glu Ile Pro Phe Ser Phe Tyr Tyr Pro Trp Glu Leu Ala Thr Ala
50                      55                      60

Pro Asp Val Arg Ile Ser Trp Arg Arg Gly His Phe His Gly Gln Ser
65                      70                      75                      80

Phe Tyr Ser Thr Arg Pro Pro Ser Ile His Lys Asp Tyr Val Asn Arg
                85                      90                      95

Leu Phe Leu Asn Trp Thr Glu Gly Gln Lys Ser Gly Phe Leu Arg Ile
                100                     105                     110

Ser Asn Leu Gln Lys Gln Asp Gln Ser Val Tyr Phe Cys Arg Val Glu
                115                     120                     125

Leu Asp Thr Arg Ser Ser Gly Arg Gln Gln Trp Gln Ser Ile Glu Gly
                130                     135                     140
```

```
Thr Lys Leu Ser Ile Thr Gln Gly Gln Gln Arg Thr Lys Ala Thr Thr
145                 150                 155                 160

Pro Ala Arg Glu Pro Phe Gln Asn Thr Glu Glu Pro Tyr Glu Asn Ile
                165                 170                 175

Arg Asn Glu Gly Gln Asn Thr Asp Pro Lys Leu Asn Pro Lys Leu His
            180                 185                 190

Leu Thr Gln Ser Thr Ser Gln Pro Pro Ser Pro Gln Glu Pro Pro Glu
        195                 200                 205

Arg Asp Pro Val Leu Cys Leu Lys Gly Leu Thr Asn Gly Gln Pro Ser
    210                 215                 220

Gln Asp
225

<210> SEQ ID NO 86
<211> LENGTH: 175
<212> TYPE: PRT
<213> ORGANISM: Homo sapiens

<400> SEQUENCE: 86

Met Gly Arg Pro Leu Leu Leu Pro Leu Leu Pro Leu Leu Pro Pro Pro
1               5                   10                  15

Ala Phe Leu Gln Pro Ser Gly Ser Thr Gly Ser Gly Pro Ser Tyr Leu
                20                  25                  30

Tyr Gly Val Thr Gln Pro Lys His Leu Ser Ala Ser Met Gly Gly Ser
            35                  40                  45

Val Glu Ile Pro Phe Ser Phe Tyr Tyr Pro Trp Glu Leu Ala Thr Ala
        50                  55                  60

Pro Asp Val Arg Ile Ser Trp Arg Arg Gly His Phe His Arg Gln Ser
65                  70                  75                  80

Phe Tyr Ser Thr Arg Pro Pro Ser Ile His Lys Asp Tyr Val Asn Arg
                85                  90                  95

Leu Phe Leu Asn Trp Thr Glu Gly Gln Lys Ser Gly Phe Leu Arg Ile
                100                 105                 110

Ser Asn Leu Gln Lys Gln Asp Gln Ser Val Tyr Phe Cys Arg Val Glu
            115                 120                 125

Leu Asp Thr Arg Ser Ser Gly Arg Gln Gln Trp Gln Ser Ile Glu Gly
    130                 135                 140

Thr Lys Leu Ser Ile Thr Gln Gly Asn Pro Ser Lys Thr Gln Arg Ser
145                 150                 155                 160

His Met Arg Ile Ser Gly Met Lys Asp Lys Ile Gln Ile Pro Ser
                165                 170                 175
```

METHODS OF TREATING INFLAMMATORY DISEASES BY ADMINISTERING ANTI-PILR-ALPHA ANTIBODY

RELATED APPLICATIONS

This application is a divisional of U.S. patent application Ser. No. 14/598,870, filed on Jan. 16, 2015, now U.S. Pat. No. 9,556,269, which is a continuation of U.S. patent application Ser. No. 13/921,557, filed on Jun. 19, 2013, now abandoned, which is a continuation of International Application No. PCT/US2011/066753, having an international filing date of Dec. 22, 2011, which claims benefit of priority applications U.S. Provisional Application No. 61/510,453, filed Jul. 21, 2011, and U.S. Provisional Application No. 61/426,945, filed Dec. 23, 2010, the entire contents of each of which are incorporated herein by reference.

SEQUENCE LISTING

A sequence listing comprising SEQ ID NOS: 1-86 is attached hereto. Each sequence provided in the sequence listing is incorporated herein by reference, in its entirety, for all purposes.

TECHNICAL FIELD

Described herein is a novel receptor-ligand interaction and agents that may modify and/or block the interaction. Methods, uses, reagents and kits for the modulation of ligand activities related to its interaction with the novel receptor are disclosed. Also disclosed are therapeutic uses of reagents in treating inflammation-related disorders. Specifically, this disclosure relates to PILRα, its ligands and methods of modulating their interaction. Also disclosed herein are methods of treating PILRα-mediated inflammation and/or diseases, e.g., pathogenic infection, autoimmune arthritis, etc.

BACKGROUND

Immune function is regulated by the balance of activating and inhibitory signals mediated by immune cell-surface receptors (Lanier, Nature Immunol. (2001) 2:23-27; Smith et al., Immunol. Rev. (2001) 181:115-125; Moretta et al., Annu. Rev. Immunol. (2001) 19:197-223; Diefenbach & Raulet, Curr. Opin. Immunol. (2003) 15:37-44.). Among these receptors, there are families that harbor extracellular regions that have a highly conserved amino-acid sequence but have different intracellular domains responsible for activation and inhibitory signaling. Thus, activating and inhibitory members of these families can generally recognize the same or very similar ligands with slightly different specificities, presumably resulting in fine-tuning of immune regulation. Since they are involved in both the activation and inhibition of immune function, they are generally referred to as paired receptor families. Paired immunoglobulin-like (Ig-like) type 2 receptors (PILRs) are one of the paired receptor families. Inhibitory receptors possess immunoreceptor tyrosine-based inhibitory motifs (ITIMs) in their cytoplasmic domains and deliver inhibitory signals via tyrosine phosphatases, such as SHP-1. The ITIM-bearing receptor PILR-alpha recruits SHP-1 via its amino-terminal SH2 domain and is likely to have cellular inhibitory potential. The lack of a cytoplasmic tail and the presence of the transmembrane lysine residue in the second receptor, PILR-beta, suggest its potential activating function. See Fournier et al., J. Immunol. (2000) 165:1197-1209; Mousseau et al., J. Biol. Chem. (2000) 275:4467-4474.; Shiratori et al., J. Exp. Med. (2004) 199: 525-533. Although the ligand for mouse PILR-alpha and PILR-beta was identified as CD99 (Shiratori et al., J. Exp. Med. (2004) 199:525-533), to date no human ligand has been identified for human PILRs.

Herpes simplex virus type 1 (HSV-1) is a member of the alphaherpesvirus subfamily and can cause recurrent mucocutaneous lesions on the mouth, face, or genitalia and potentially meningitis or encephalitis. Membrane glycoprotein B (gB) of HSV-1 is a second ligand for PILR-alpha (Satoh et al., Cell (2008) 132:935-944). The interaction of HSV-1 gB with PILRa mediates viral entry and cell-cell fusion. Interestingly, expression of PILRa on cells enhances HSV-1 entry, whereas expression of PILRb does not (Fan and Longnecker, J. Virol. (2010) 84(17):8664-8672). This suggests HSV-1 gB is not a ligand of PILRb, and subtle amino acid differences between a and b play a role in ligand selectivity. Interestingly, binding of PILRa to HSV-1 gB also requires sialylated O-glycans (T53, T480) (Fan et al., J. Virol. (2009) 83(15):7384-7390). PILRa specifically associates with HSV-1 gB, but not with other HSV-1 glycoproteins, although some other envelope proteins are known to be O-glycosylated (Fan et al., J. Virol. (2009) 83(15):7384-7390).

Although PILR-alpha and PILR-beta are abundantly expressed on myeloid cells, very little is known about their role in host defense against extracellular bacterial infection or in immune function. Thus, elucidating the role for PILR-alpha and PILR-beta is a necessary prerequisite for the prevention/treatment of diseases/conditions associated with PILR-alpha and/or PILR-beta dysfunction. The present disclosure identifies sialidated glycans as necessary and sufficient for hPILRa binding. The present disclosure also provides a method and compositions, such as selective binding agents, to modulate the interactions of the PILR and its ligands. Specifically, described herein are novel reagents and methods based on the interaction of infective microorganisms and/or endogenous ligands for the prevention/treatment of diseases/conditions associated with PILR-alpha and/or PILR-beta activity.

BRIEF SUMMARY OF THE INVENTION

The present disclosure relates to various methods, uses, reagents, and kits based on modulation of the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA.

One embodiment of the invention relates to an agent that may block the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA.

Another embodiment of the present invention relates to a composition that may comprise (1) an agent that may block the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA, and (2) a pharmaceutically acceptable carrier.

Another embodiment of present invention further relates to a method for blocking the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA;

the method may comprise the step of administering an effective amount of an agent that may block the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA.

Another embodiment of the present invention provides an interaction occurring at the cell surface and a method for blocking the cell surface interaction between a PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA may comprise contacting cells (a cell expressing PILR-alpha and/or a cell expressing a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA) with an effective amount of an agent that may block the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA.

Another embodiment of the present invention provides a method for inhibiting production of an inflammatory mediator by a cell, the method may comprise blocking the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA.

Another embodiment of the present invention relates to the use of an agent that may block the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA for the preparation of a medicament that may block the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA.

Another embodiment of the present invention relates to the use of an agent for treating an inflammatory disease/condition in a subject and/or for the preparation of a medicament for treating an inflammatory disease in a subject, wherein the agent may block the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA.

Another embodiment of the present invention relates to a method for identifying a compound capable of blocking the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA; the method may comprise measuring the binding of PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA in the presence versus the absence of an agent, wherein a lower binding of PILR-alpha to said ligand in the presence of the agent (in comparison with the absence of the agent) may be indicative that the agent is capable of blocking the interaction between PILR-alpha and said ligand.

Another embodiment of the present invention relates to a method for identifying a compound capable of inhibiting and/or decreasing inflammation; the method may comprise measuring the binding of PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA in the presence versus the absence of the agent, wherein a lower binding of PILR-alpha to the ligand in the presence of the agent may be indicative that the agent is capable of inhibiting or decreasing inflammation.

Another embodiment of the present invention provides a method of treating an inflammatory disease or condition in a subject; the method may comprise blocking the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA in the subject.

Another embodiment of the present invention relates to a use of an agent capable of blocking the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA for treating an inflammatory disease or condition in a subject.

Another embodiment of the present invention relates to a use of an agent capable of blocking the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA for the preparation of a medicament for treating an inflammatory disease or condition in a subject.

Another embodiment of the present invention relates to a composition for treating an inflammatory disease or condition in a subject comprising (1) an agent capable of blocking the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA and (2) a pharmaceutically acceptable carrier.

Another embodiment of the present invention relates to an agent that may stimulate the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA.

Another embodiment of the present invention relates to a composition that may comprise (1) an agent that may stimulate the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA and (2) a pharmaceutically acceptable carrier.

Another embodiment of the present invention relates to a method for stimulating the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA; the method may comprise the step of administering an effective amount of an agent that may stimulate the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA.

In an embodiment of the present invention, the interaction may occur at the cell surface and a method for stimulating the cell surface interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA may comprise contacting cells (a cell expressing PILR-alpha and/or a cell expressing a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA) with an effective amount of an agent that may stimulate the interaction between PILR-alpha and said ligand.

An additional embodiment of the present invention provides a method for inhibiting production of an inflammatory mediator by a cell, the method may comprise stimulating the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA.

A further embodiment of the present invention relates to the use of an agent that may stimulate the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA for the preparation of a medicament that may stimulate the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA.

An embodiment of the present invention relates to the use of an agent for treating an inflammatory disease in a subject and/or for the preparation of a medicament for treating an inflammatory disease in a subject wherein the agent may stimulate the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA..

Another embodiment of the present invention relates to a method for identifying a compound capable of stimulating the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA; the method may comprise measuring the binding of PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA in the presence versus the absence of an agent, wherein an elevated binding of PILR-alpha and said ligand in the presence of the agent (in comparison with the absence of the agent) may be indicative that the agent is capable of stimulating the interaction between PILR-alpha and said ligand.

Another further embodiment of the present invention relates to a method for identifying a compound capable of stimulating the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA; the method may comprise measuring PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA activity in the presence or absence of the agent, wherein an elevated PILR-alpha activity in the presence of the agent may be indicative that the agent is stimulating the interaction between PILR-alpha and said ligand.

Another embodiment of the present invention relates to a method for identifying a compound capable of inhibiting and/or decreasing inflammation; the method may comprise measuring the binding of PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA in the presence versus the absence of the agent, wherein an elevated binding of PILR-alpha and said ligand in the presence of the agent may be indicative that the agent is capable of inhibiting or decreasing inflammation.

Yet another embodiment of the present invention provides a method of identifying a compound capable of inhibiting or decreasing inflammation; the method may comprise measuring PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA activity in the presence versus the absence of the agent, wherein an elevated PILR-alpha activity in the presence of the agent may be indicative that the agent is capable of inhibiting or decreasing inflammation.

A further embodiment of the present invention provides a method of treating an inflammatory disease or condition in a subject; the method may comprise stimulating the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA in the subject.

Another embodiment of the present invention relates to a use of an agent capable of stimulating the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA for treating an inflammatory disease or condition in a subject.

Another embodiment of the present invention relates to a use of an agent capable of stimulating the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA for the preparation of a medicament for treating an inflammatory disease or condition in a subject.

Another embodiment of the present invention relates to a composition for treating an inflammatory disease or condition in a subject comprising an agent capable of stimulating the interaction between PILR-alpha and a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA and a pharmaceutically acceptable carrier.

In some aspects of any of the foregoing embodiments the ligand may be any one of NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA.

One more embodiment of the present invention relates to variants of PILR-alpha. In one aspect, the variant comprises an alteration at a residue corresponding to R133 in SEQ ID NO:1. The alteration may be the addition, deletion or substitution of the residue. The variant may comprise a mutation corresponding R133A. In another aspect, the variant comprises an alteration at a residue corresponding to R126 in SEQ ID NO:3. The alteration may be the addition, deletion or substitution of the residue. The variant may comprise a mutation corresponding R126A. In a further aspect, the variant comprises an alteration that abrogates binding of PILRa to a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA. In a further aspect, the variant comprises an alteration that inhibits or decreases binding of PILRa to a ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA.

An additional embodiment of the present invention relates to a binding motif for ligands of PILR-alpha. In one aspect, the ligands comprise a sialidated glycan domain. In a second aspect, the human PILR-alpha binds to a ligand is via a sialoadhesin homology domain.

In a different embodiment, at least one ligand selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA interacts with PILR-beta. In an aspect, the ligand binds to PILR-beta but with lower affinity than to PILR-alpha.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE DRAWINGS

FIGS. 1A-1E illustrate that PILRα binds to mouse but not human CD99 and that transfer of mouse CD99 PKAPT motif to human CD99 restores PILRα binding. FIG. 1A: 293T cells were transfected with mouse and human CD99 expression vectors and the transfectants were stained with hPILRα-Fc (black line), mouse PILRα-Fc (black line) or control Ig (grey area). CD99 expressing cells were gated and their binding to PILRα-Fc was shown. FIG. 1B: Comparison of profiles of O-glycans from human and mouse CD99-Fc fusion proteins. O-glycans were released by reductive β-elimination and permethylated then analyzed by MALDI-TOF MS. FIG. 1C: shows the glycosylation motifs in mouse CD99 and the variant human CD99 where the mouse PKAPT motif was inserted (GB_HSV1/476-484: SEQ ID NO: 67, GB_HSV1/48-57: SEQ ID NO: 68, CD99_MOUSE/41-49: SEQ ID NO: 69, CD99_MOUSE/46-54: SEQ ID NO: 70, CD99_HUMAN/46-51: SEQ ID NO: 71, CD99_HUMAN/46-54: SEQ ID NO: 72). See FIG. 5A in Shiratori et al., *J. Exp. Med.* (2004) 199(4):525-533 for the mouse CD99 sequence. FIG. 1D: illustrates the recovery of binding of human CD99 with the PKAPT motif inserted (i.e., the PKAPT motif from mouse CD99 was inserted into the human CD99) to both mouse and human PILRa. Both human and mouse PILRa bind mouse CD99 (second row) but fail to bind human CD99 (third row). FIG. 1E: 293T cells were transfected with mouse, human CD99 or human CD99 with mouse PKAPT motif inserted after T41 and the transfectants were stained with hPILRα-Fc (black line), mouse PILRα-Fc (black line) or control Ig (grey area).

FIG. 2A: COS7 cells were transfected with hNPDC1 and hCOLEC12 expression vectors, stained with hPILRα-AP, mPILRα-AP and control supernatant followed with AP substrate. FIG. 2B: 293T cells were transfected with mCD99, hNPDC1 and hCOLEC12, and the transfectants were stained with isotype control, hPILRα-Fc or mouse PILRα-Fc (black line). Binding to mock transfectants (grey area) represents background binding. Transfected ligand expressing cells were gated and their binding to PILRα-Fc was shown. FIG. 2C: 293T cells were transfected with human and mouse PILRα, and the transfectants were stained with hNPDC1-Fc or hCOLEC12-his (black line). Binding to mock transfectants (grey area) represents background binding. PILRα positive cells were gated and ligand fusion staining was shown. FIG. 2D: Radioligand assay was used to determine the equilibrium binding affinity of hPILRα-Fc to hNPDC1 transiently expressed on 293T cells. $^{125}$I labeled hPILRaα-Fc was allowed to bind to cells in the presence of increasing amounts of unlabeled hPRILa-Fc. The average equilibrium $K_D$ from two replicate assays was 49 nM. FIG. 2E: SPR equilibrium binding analysis of hPILRα-Fc binding to immobilized hCOLEC12 is shown. The equilibrium $K_D$ for hPILRα/hCOLEC12 was 1.1 uM.

FIGS. 5A-5G illustrate that a conserved Arginine site in PILRα is required for its binding to ligand. FIG. 5A: Amino acid sequence alignment of PILRα from human (SEQ ID NO: 73), chimp (SEQ ID NO: 74), cow (SEQ ID NO: 75), dog (SEQ ID NO: 76), rat (SEQ ID NO: 77), and mouse (SEQ ID NO: 78); PILRβ from human (SEQ ID NO: 79) and mouse (SEQ ID NO: 80); and N-terminal of SIGLEC1 from human (SEQ ID NO: 81) and mouse (SEQ ID NO: 82). The positions of Ig fold residues are designated by an arrow above the sequence (↓) based on comparison with Igk/1 and TCRb V set Ig domains. Conserved non-Ig PILRα residues are designated by an § above the sequence. SIGLEC1 residues involved in the sialic acid-binding are boxed (dashed lines). Conserved Siglec residues across the family are boxed (solid lines). Asterisks represent PILRα amino acids that are important for sialic acid interaction. Solid arrows beneath the sequence denote the positions corresponding to active sites of SIGLEC1 crystal structure (and PILRα homology model). The underlined segments designate beta strands in PILR. Black circles represent the mutational binding analysis that have been done on PILRα. The pairwise-percentage-residue identity between PILRα and SIGLEC1 was 23%. FIG. 5B: 293T cells were transfected with wild type human and mouse PILRα (grey line), or human PILRαR126A and mouse PILRα133A (black line) expression constructs, and the transfectants were stained with mCD99-Fc, hNPDC1-Fc or hCOLEC12-his, their binding to mock transfectants (grey area) was shown as background binding. PILRα positive cells were gated and ligand fusion staining was shown. FIG. 5C: 293T cells were transfected with mouse CD99, human NPDC1, human COLEC12, or HSV1 gB expression vectors, and the transfectants were stained with hPILRα-Fc or mPILRα-Fc (grey line), hPILRαR126A-Fc or mPILRαR133A-Fc (black line), their binding to mock transfectants (grey area) was shown as background binding. Transfected ligand expressing cells were gated and PILRα-Fc staining was shown. FIG. 5D: 293T cells were infected with HSV1. Twenty-four hours later (FIG. 5D-1) glycoprotein B expression in HSV1 (black line) or mock (grey area) infected cells was shown; FIG. 5D-2, hPILRα-Fc or mPILRα-Fc (grey line), hPILRαR126A-Fc or mPILRαR133A-Fc (black line) binding to HSV1 infected cells was shown, their binding to mock transfectants (grey area) was shown as background binding. FIG. 5E: WT hPILRa-Fc and hPILRa R126-Fc were immobilized on a chip and their binding to hNPDC1, hCOLEC12, and mCD99 was compared. All three proteins showed strong binding to WT hPILRa (upper three dashed lines on the graph). Little or no binding was observed with mutant hPILRa, suggesting this conserved Arg site is necessary for binding of PILRa to its ligands (lower three lines on the graph with the Mut designation). FIG. 5F: The binding of ligand fusion proteins to wild type and Arginine mutated human PILRα. The binding of selected proteins to hPILRα was determined by SPR. Human PILRα-Fc and PILRαR126A-Fc was immobilized to a sensor chip. Fusion proteins were used as analytes (1 µM). F. The binding of hPILRα-Fc or mPILRα-Fc (grey line), hPILRαR126A-Fc or mPILRαR133A-Fc (black line) to human PBMC, T cells and monocytes (FIG. 5F-1), mouse thymocyte, CD8+T and B cells (FIG. 5F-2) was shown, the binding of isotype control to these cells (grey area) was shown as background binding. FIG. 5G: alignment of four human PILRa isoforms, NP_038467 (SEQ ID NO: 83), NP_840056 (SEQ ID NO: 84), AAH17812 (SEQ ID NO: 85), and NP_840057 (SEQ ID NO: 86).

FIG. 8C also shows the binding of mPILRb to the same ligands. Note that the variant mPILRa does not bind and that mPILRb binds to a lesser degree than mPILRa for CLEC4G and FceRII.

FIG. 9C also shows the binding of mPILRb to the same ligands. Note that the variant mPILRa does not bind and that mPILRb binds to a lesser degree than mPILRa for FcRII.

FIG. 10C also shows the binding of mPILRb to the same ligands. Note that the variant mPILRa does not bind and that mPILRb binds to a lesser degree than mPILRa for BR3.

FIG. 12 is a table showing the various tissue and/or cell types that express each of the listed ligands.

DETAILED DESCRIPTION

Figures 1A, 1C:
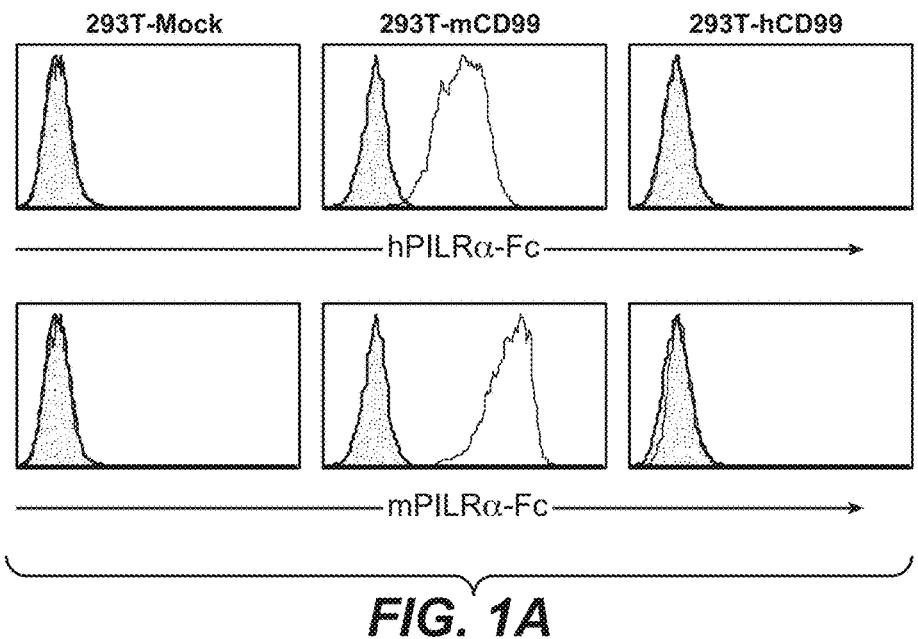

The invention will now be described in detail by way of reference only using the following definitions and examples.

All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

Numeric ranges are inclusive of the numbers defining the range.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

Definitions

PILR Family Members

As used herein, "PILR" refers to paired immunoglobulin-like receptors (PILR) alpha and beta. They are related type I transmembrane receptors bearing a highly similar (83% identity) extracellular Ig-like variable (V)-type domain but divergent intracellular signaling domains. When only one of the members is being referenced, it will be designated as either PILRα or PILRβ.

Mouse PILR-alpha (mPILRα) as used herein refers to the protein having the amino acid sequence of SEQ ID NO: 1, which includes a potential signal sequence. Human PILR-alpha (hPILRα) as used herein refers to the protein having the amino acid sequence of SEQ ID NO: 3, which includes a potential signal sequence. Paired immunoglobulin-like receptor alpha, ITIM-containing inhibitory receptor of the PILR family that associates with SHP-1 (PTPN6) and SHP-2 (PTPN11), involved in signaling and inhibits activation-dependent calcium mobilization in monocytic cells. PILR-alpha may also be referred to as PILRa or PILRα herein.

Mouse PILR-beta (mPILRb) as used herein refers to the protein having the amino acid sequence of SEQ ID NO:33 Human PILR-beta (hPILRb) as used herein refers to the protein having the amino acid sequence of SEQ ID NO:35, which includes a potential signal sequence. Paired immunoglobulin like type 2 receptor beta, may play a role in transmembrane receptor protein tyrosine kinase signaling pathway. Increased expression of the gene encoding the protein is associated with acute lymphoblastic leukemias. PILR-beta may also be referred to as PILRb or PILRβ herein.

PILR Ligands

NPDC1 as used herein refers to the protein having the amino acid sequence of SEQ ID NO: 5, which includes a potential signal sequence. Neural proliferation, differentiation and control, I (NPDC1) is specifically expressed in neural cells when they stop to divide and begin to differentiate. It may also regulate transcription, cell proliferation, neuron differentiation, and organ morphogenesis. Its expression is developmentally regulated and persists in the adult; it increases in the embryonic brain, in distinct, defined regions, and is correlated with growth arrest and terminal differentiation. NPDC1 has long hydrophobic stretch of amino acids (residues 13-29), a coiled-coil region (amino acids 93-120), a transmembrane domain (amino acids 191-207), an acidic domain (amino acids 277-307), and MAP-kinases consensus sites (amino acids 234-244) (Evrard and Rouget, (2005) *J. Neuro. Res.* 79:747-755). It may be clipped and exist in a soluble form.

COLEC12 as used herein refers to the protein having the amino acid sequence of SEQ ID NO: 7. Collectin subfamily member 12 (COLEC12) is a type II transmembrane glycoprotein that binds bacteria through its lectin domain and may play a role in host defense.

ETBR as used herein refers to the protein having the amino acid sequence of SEQ ID NO: 8, which includes a potential signal sequence. Endothelin receptor type B (ETBR) regulates angiogenesis, smooth muscle contraction, and cell migration; gene mutation correlates with melanoma, Waardenburg syndrome, and Hirschsprung disease, aberrantly expressed in asthma, atherosclerosis, and several cancers.

CLEC4G as used herein refers to the protein having the amino acid sequence of SEQ ID NO: 10, which includes a potential signal sequence. C type lectin superfamily 4 member G (CLEC4G) is a homodimerizing protein that functions as a pathogen associated molecular pattern receptor, may play a role in cell-cell adhesion, antigen processing, and presentation. See also, Liu et al., (2004) *J. Biol. Chem.* 279(18):18748-58.

BR3 as used herein refers to the protein having the amino acid sequence of SEQ ID NO: 12. BR3 is a 184-residue type III transmembrane protein expressed on the surface of B cells (Thompson, et al., (2001) *Science* 293:2108-2111; Yan, et al., (2001) *Curr. Biol.* 11:1547-1552). BR3 is expressed in a variety of disease tissue including multiple myeloma and non-Hodgkin Lymphoma (Novak, A J (2004) *Blood* 104:2247-2253; Novak, A J (2004) *Blood* 103:689-694). BR3 mediates NF-kappaB activation and IL10 production, elevated mRNA levels are associated with systemic lupus erythematosus and multiple sclerosis.

MAG as used herein refers to the protein having the amino acid sequence of SEQ ID NO: 13, which includes a potential signal sequence. Myelin associated glycoprotein (MAG, also called SIGLEC4A) may play a role in cell adhesion. An increase in autoimmune antibody correlates with autism, demyelinating diseases, and polyneuropathies associated with paraproteinemias. Gene polymorphism is associated with schizophrenia.

IL-2Ra as used herein refers to the protein having the amino acid sequence of SEQ ID NO: 15, which includes a potential signal sequence. Interleukin 2 receptor alpha, plays a role in regulation of T cell mediated immune response, expression is altered in several neoplasms, immune system and inflammatory diseases, Parkinson disease, asthma, and type I diabetes mellitus.

FceRII as used herein refers to the protein having the amino acid sequence of SEQ ID NO: 17. Fc fragment of IgE low affinity II receptor, acts in thymocyte maturation, histamine secretion, and TNF production, regulates NO production in monocytes, upregulated in hypogammaglobulinaemia, Kawasaki disease, Graves thyrotoxicosis, and chronic uremia.

LRRTM4 as used herein refers to the protein having the amino acid sequence of SEQ ID NO: 18, which includes a potential signal sequence. Leucine rich repeat transmembrane neuronal 4 may stimulate beta-secretase mediated processing of beta-amyloid-precursor protein, may play a role in brain development and is associated with Alzheimer disease. LRRTM4 contains nine leucine rich repeats.

DAG1 as used herein refers to the protein having the amino acid sequence of SEQ ID NO: 20, which includes a potential signal sequence. Dystroglycan 1 or dystrophin-associated glycoprotein 1 (DAG1) is an extracellular matrix glycoprotein that acts in muscle contraction, may be involved in synaptic transmission and establishment of cell polarity, aberrant protein expression correlates with muscular dystrophies and several neoplasms.

APLP1 as used herein refers to the protein having the amino acid sequence of SEQ ID NO: 22, which includes a potential signal sequence. Amyloid beta precursor like protein 1 (APLP1) is an alpha 2A adrenergic receptor binding protein that regulates proteolysis of amyloid precursor proteins, negatively regulates endocytosis; map position of corresponding gene correlates with Alzheimer disease.

PTPRN as used herein refers to the protein having the amino acid sequence of SEQ ID NO: 24, which includes a potential signal sequence. Protein tyrosine phosphatase receptor-type N (PTPRN) is a putative transmembrane receptor protein tyrosine phosphatase that acts as an autoantigen in type 1 diabetes mellitus.

WDR31 as used herein refers to the protein having the amino acid sequence of SEQ ID NO: 26, which includes a potential signal sequence. WD repeat domain 31 (WDR31) contains five WD domain G-beta repeats, has low similarity to *S. pombe* Cpc2p, which is required for normal mating, sporulation, and protein translation and is a putative receptor for *S. pombe* Pck2p during cell wall synthesis and morphogenesis.

PSS8 as used herein refers to the protein having the amino acid sequence of SEQ ID NO: 27, which includes a potential signal sequence. Protease serine 8 or prostasin (PSS8) is a serine protease that plays a role in regulation of the amiloride-sensitive epithelial sodium channel, overexpressed in ovarian cancer cells; corresponding gene expression is downregulated in prostate cancers.

SIGLEC7 as used herein refers to the protein having the amino acid sequence of SEQ ID NO: 29, which includes a potential signal sequence. Sialic acid binding Ig-like lectin 7 (SIGLEC7) is a disialoganglioside-binding inhibitory receptor in natural killer cells that may act in myelopoiesis. It interacts with the lipooligosaccharide (LOS) on the surface of *Campylobacter jejuni*.

IL15-RA as used herein refers to the protein having the amino acid sequence of SEQ ID NO: 31, which includes a potential signal sequence. Interleukin 15 receptor alpha (IL15-RA), the interleukin-15 (IL15)-binding subunit of the receptor, functions in signal transduction, cell proliferation, and natural killer cell survival, may be involved in the cellular defense response to various pathogens.

The term "antibody" herein is used in the broadest sense and refers to any immunoglobulin (Ig) molecule comprising two heavy chains and two light chains, and any fragment, mutant, variant or derivation thereof which so long as they exhibit the desired biological activity (e.g., epitope binding activity). Examples of antibodies include monoclonal antibodies, polyclonal antibodies, multispecific antibodies and antibody fragments.

The Kabat numbering system is generally used when referring to a residue in the variable domain (approximately residues 1-107 of the light chain and residues 1-113 of the heavy chain) (e.g, Kabat et al., *Sequences of Immunological Interest*. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

The term "multispecific antibody" is used in the broadest sense and specifically covers an antibody that has poly-epitopic specificity. Such multispecific antibodies include, but are not limited to, an antibody comprising a heavy chain variable domain ($V_H$) and a light chain variable domain ($V_L$), where the $V_H V_L$ unit has polyepitopic specificity, antibodies having two or more $V_L$ and $V_H$ domains with each $V_H V_L$ unit binding to a different epitope, antibodies having two or more single variable domains with each single variable domain binding to a different epitope, full length antibodies, antibody fragments such as Fab, Fv, dsFv, scFv, diabodies, bispecific diabodies and triabodies, antibody fragments that have been linked covalently or non-covalently. "Polyepitopic specificity" refers to the ability to specifically bind to two or more different epitopes on the same or different target(s). "Monospecific" refers to the ability to bind only one epitope. According to one embodiment the multispecific antibody is an IgG antibody that binds to each epitope with an affinity of 5 µM to 0.001 pM, 3 µM to 0.001 pM, 1 µM to 0.001 pM, 0.5 µM to 0.001 pM, or 0.1 µM to 0.001 pM.

In the studies described herein, Applicants have demonstrated that PILR is a functional receptor for sialidated glycan ligands. Specifically, the ligand is selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA.

Other Definitions

The terms "PILR gene" or "PILR nucleic acid molecule" or "polynucleotide" refers to a nucleic acid molecule comprising or consisting of a nucleotide sequence encoding a specific PILR polypeptide. Exemplary nucleotide sequences are set forth in FIG. 1A of Fournier et al., *J. Immunol.* (2000) 165:1197-1209 and NM_013439 for human PILRa; multiple cDNAs have been identified for PILRβ (Wilson et al., (2006) Physiol. Genomics 27:201-18.) and annotated by NCBI, e.g., NM_178238.1, NM_178238.2, for human PILRb.

The term "polypeptide allelic variant" refers to the polypeptide encoded by one of several possible naturally occurring alternate forms of a gene occupying a given locus on a chromosome of an organism or a population of organisms.

The term "polypeptide derivatives" refers to a polypeptide that has been chemically modified.

The term "polypeptide fragment" refers to a polypeptide that comprises a truncation at the amino terminus (with or without a leader sequence) and/or a truncation at the carboxy terminus of the polypeptide whose sequence is as defined herein. Polypeptide fragments may result from alternative RNA splicing or from in vivo protease activity. For transmembrane or membrane-bound forms of the polypeptides, preferred fragments include soluble forms such as those lacking a transmembrane or membrane-binding domain.

In preferred embodiments, truncations comprise about 10 amino acids, or about 20 amino acids, or about 50 amino acids, or about 75 amino acids, or about 100 amino acids, or more than about 100 amino acids. The polypeptide fragments so produced will comprise about 25 contiguous amino acids, or about 50 amino acids, or about 75 amino acids, or about 100 amino acids, or about 150 amino acids, or about 200 amino acids. Such polypeptide fragments may optionally comprise an amino terminal methionine residue. It will be appreciated that such fragments can be used, for example, to generate antibodies to the polypeptides.

The term "PILR fusion polypeptide" refers to a fusion of one or more amino acids (such as a heterologous peptide or polypeptide) at the amino or carboxy terminus of a PILR polypeptide. In an aspect the heterologous polypeptide is an Fc region of on IgG.

The term "polypeptide ortholog" refers to a polypeptide from another species that corresponds to an polypeptide as defined herein. For example, mouse and human PILRa polypeptides are considered orthologs of each other. For ease of reference, the human and mouse PILRa polypeptide sequences are aligned and shown in FIG. 1C of Fournier et al., (2000) supra.

The term "polypeptide variants" refers to, for example, PILRa polypeptides comprising amino acid sequences having one or more amino acid sequence substitutions, deletions (such as internal deletions and/or PILRa polypeptide fragments), and/or additions (such as internal additions and/or PILRa fusion polypeptides) as compared to the PILRa polypeptide as defined above. Variants may be naturally occurring (e.g., PILRa polypeptide allelic variants, PILRa polypeptide orthologs and PILRa polypeptide splice variants) or may be artificially constructed. Such PILRa polypeptide variants may be prepared from the corresponding nucleic acid molecules having a DNA sequence that varies accordingly from the DNA sequence as defined above for the PILRa gene. In preferred embodiments, the variants have from 1 to 3, or from 1 to 5, or from 1 to 10, or from 1 to 15, or from 1 to 20, or from 1 to 25, or from 1 to 50, or from 1 to 75, or from 1 to 100, or more than 100 amino acid substitutions, insertions, additions and/or deletions, wherein the substitutions may be conservative, or non-conservative, or any combination thereof.

In general, a polypeptide "variant" (i.e. a variant of any polypeptide disclosed herein) means a biologically active polypeptide having at least about 80% amino acid sequence identity with the corresponding native sequence polypeptide. Such variants include, for instance, polypeptides wherein one or more amino acid (naturally occurring amino acid and/or a non-naturally occurring amino acid) residues are added, or deleted, at the N- and/or C-terminus of the polypeptide. Ordinarily, a variant will have at least about 80% amino acid sequence identity, or at least about 90% amino acid sequence identity, or at least about 95% or more amino acid sequence identity with the native sequence polypeptide. Variants also include polypeptide fragments (e.g., subsequences, truncations, etc.), typically biologically active, of the native sequence.

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2. The ALIGN-2 sequence comparison computer program was authored by Genentech, Inc. has been filed with user documentation in the U.S. Copyright Office, Washington D.C., 20559, where it is registered under U.S. Copyright Registration No. TXU510087, and is publicly available through Genentech, Inc., South San Francisco, Calif. The ALIGN-2 program should be compiled for use on a UNIX operating system, e.g., digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous protein will often refer to two or more subsequences that are not found in the same relationship to each other in nature (e.g., a fusion protein).

"Essentially pure" protein means a composition comprising at least about 90% by weight of the protein, based on total weight of the composition, preferably at least about 95% by weight, more preferably at least about 90% by weight, even more preferably at least about 95% by weight. "Essentially homogeneous" protein means a composition comprising at least about 99% by weight of protein, based on total weight of the composition.

The term "antagonist" when used herein refers to a molecule capable of neutralizing, blocking, inhibiting, abrogating, reducing or interfering with the activities of a protein of the invention including its binding to one or more receptors in the case of a ligand or binding to one or more ligands in case of a receptor. Antagonists include antibodies and antigen-binding fragments thereof, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. Antagonists also include small molecule inhibitors of a protein of the invention, and fusions proteins, receptor molecules and derivatives which bind specifically to protein thereby sequestering its binding to its target, antagonist variants of the protein, antisense molecules directed to a protein of the invention, RNA aptamers, and ribozymes against a protein of the invention.

A "blocking" antibody or an "antagonist" antibody is one which inhibits or reduces biological activity of the antigen it binds. Certain blocking antibodies or antagonist antibodies substantially or completely inhibit the biological activity of the antigen.

The term "antigen" refers to a molecule or a portion of a molecule capable of being bound by a selective binding agent, such as an antibody, and additionally capable of being used in an animal to produce antibodies capable of binding to an epitope of each antigen. An antigen may have one or more epitopes.

The terms "active" and "biologically active" polypeptides refer to polypeptides having at least one activity characteristic of the reference polypeptide. For example, the enzymatic activity associated with a protease is proteolysis and, thus, an active protease has proteolytic activity. It follows that the biological activity of a given protein refers to any biological activity typically attributed to that protein by those of skill in the art. as defined above.

As used herein, the term "immunoadhesin" designates antibody-like molecules that combine the binding specificity of a heterologous protein (an "adhesin") with the effector functions of immunoglobulin constant domains. Structurally, the immunoadhesins comprise a fusion of an amino acid sequence with the desired binding specificity that is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand—such as a PILRa, for example. The immunoglobulin constant domain sequence in the immunoadhesin can be obtained from any immunoglobulin, such as IgG-1, IgG-2, IgG-3, or IgG-4 subtypes, IgA (including IgA-1 and IgA-2), IgE, IgD, or IgM.

In one aspect thereof, the present invention relates to an agent that may block the interaction between a ligand (as defined herein) and a PILR family member. In another aspect, the present invention relates to an agent that may modulate the interaction between a ligand (as defined herein) and a PILR family member.

As used herein, an "agent" that may block the interaction between a ligand (as defined herein) and PILRa may be a protein. For example, such protein may be an (isolated) antibody, or antigen-binding fragment (portion) thereof, that may specifically bind to a ligand (as defined herein) and/or PILRa. The antibody may be, for example, a monoclonal antibody and/or a polyclonal antibody. Monoclonal antibodies (MAbs) may be made by one of several procedures available to one of skill in the art, for example, by fusing antibody producing cells with immortalized cells and thereby making a hybridoma. The general methodology for fusion of antibody producing B cells to an immortal cell line is well within the province of one skilled in the art. Another example is the generation of MAbs from mRNA extracted from bone marrow and spleen cells of immunized animals using combinatorial antibody library technology. One drawback of MAbs derived from animals or from derived cell lines is that although they may be administered to a patient for diagnostic or therapeutic purposes, they are often recognized as foreign antigens by the immune system and are unsuitable for continued use. Antibodies that are not recognized as foreign antigens by the human immune system have greater potential for both diagnosis and treatment. Methods for generating human and humanized antibodies are now well known in the art.

Polyclonal antibodies may be obtained by immunizing a selected animal with a protein or polypeptide (for example without limitation a ligand or PILRa or PILRb). Serum from the animal may be collected and treated according to known procedures. Polyclonal antibodies to the protein or polypeptide of interest may then be purified by affinity chromatography. Techniques for producing polyclonal antisera are well known in the art.

Antibodies may originate for example, from a mouse, rat or any other mammal. The antibody may also be a human antibody which may be obtained, for example, from a transgenic non-human mammal capable of expressing human immunoglobulin genes. The antibody may also be a humanized antibody which may comprise, for example, one or more complementarity determining regions of non-human origin. It may also comprise a surface residue of a human antibody and/or framework regions of a human antibody. The antibody may also be a chimeric antibody which may comprise, for example, variable domains of a non-human antibody and constant domains of a human antibody. Suitable antibodies may also include, for example, an antigen-binding fragment, a Fab fragment; a F(ab')2 fragment, and Fv fragment; or a single-chain antibody comprising an antigen-binding fragment (e.g., a single chain Fv). An antibody encompassed in the present invention may be an antibody binding specifically to PILRa. In an embodiment, an antibody encompassed in the present invention may be an antibody binding specifically to a ligand (as described herein).

Anti-PILR agents (e.g. antibodies) may be experimentally tested and validated using in vivo and in vitro assays. Suitable assays include, but are not limited to, activity assays and binding assays.

The activity of a ligand interaction with PILR may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3. 1-3.19; Chapter 7, Immunologic studies in Humans); Herrmann, et al., *Proc. Natl. Acad. Sci. USA* 78:2488-2492 (1981); Herrmann, et al., *J. Immunol.* 128:1968-1974 (1982); Handa, et al., *J. Immunol.* 135:1564-1572 (1985); Takai, et al., *J. Immunol.* 137:3494-3500 (1986); Takai, et al., *J. Immunol.* 140:508-512 (1988); Bowman, et al., *J. Virology* 61:1992-1998; Bertagnolli, et al., *Cellular Immunology* 133:327-341 (1991); Brown, et al., *J. Immunol.* 153:3079-3092 (1994).

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, *J. Immunol.* 144:3028-3033 (1990); and Assays for B cell function: In vitro antibody production, Mond, J. J. and Brunswick, M. In Current Protocols in Immunology. J. E. e.a. Coligan eds. Vol 1 pp. 3.8.1-3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1-3.19; Chapter 7, Immunologic studies in Humans); Takai, et al., *J. Immunol.* 137:3494-3500 (1986); Takai, et al., *J. Immunol.* 140:508-512 (1988); Bertagnolli, et al., *J. Immunol.* 149:3778-3783 (1992).

Dendritic cell-dependent assays (which will identify, among others, proteins expressed by dendritic cells that activate naive T-cells) include, without limitation, those described in: Guery et al., *J. Immunol.* 134:536-544 (1995); Inaba et al., *J. Exp. Med.* 173:549-559 (1991); Macatonia, et al., *J. Immunol.* 154:5071-5079 (1995); Porgador, et al., *J. Exp. Med.* 182:255-260 (1995); Nair, et al., *J. Virology* 67:4062-4069 (1993); Huang, et al., *Science* 264:961-965 (1994); Macatonia, et al., *J. Exp. Med.* 169:1255-1264 (1989); Bhardwaj, et al., *J. Clin. Invest.* 94:797-807 (1994); and Inaba, et al., *J. Exp. Med.* 172:631-640 (1990).

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., *Cytometry* 13:795-808 (1992); Gorczyca, et al., *Leukemia* 7:659-670 (1993); Gorczyca, et al., *Cancer Res.* 53:1945-1951 (1993); Itoh, et al., *Cell* 66:233-243 (1991); Zacharchuk, *J. Immunol.* 145:4037-4045 (1990); Zamai, et al., *Cytometty* 14:891-897 (1993); Gorczyca, et al., *Int. J. Oncol.* 1:639-648 (1992).

Assays for proteins that influence early steps of T-cell commitment and development include, without limitation, those described in: Antica, et al., *Blood* 84:111-117 (1994); Fine, et al., *Cell. Immunol.* 155:111-122, (1994); Galy, et al., *Blood* 85:2770-2778 (1995); Toki, et al., *Proc. Nat. Acad. Sci. USA* 88:7548-7551 (1991).

According to the present invention, a (protein) agent may also be a "soluble protein". Soluble proteins (purified) of the invention may be obtained from any techniques well known in the art. For example, a soluble protein may be obtained by transfecting a recombinant DNA molecule expressing solely the extracellular region of a molecule and/or portion thereof followed by purification. In another example, a protein and/or a portion of a protein (for example an extracellular region exempt of its transmembrane and cytoplasmic domains) may be fused to a constant domain (Fc portion) of an immunoglobulin. A (purified) soluble protein of the present invention may be soluble PILR and/or portion thereof. By "portion" (of soluble protein for example) it is meant a portion that exhibits similar (biological) activity yet is smaller in size. An agent of the present invention may be soluble PILRa. An agent of the present invention may be portions of soluble PILRa. Human PILRa (SEQ ID NO: 3) is a 303 amino acid protein. Its extracellular domain is approximately 170 amino acids in length. A (purified) soluble human PILRa may have a sequence that may consist from about residue 20 to residue 207 of SEQ ID NO:3. The present invention relates to and explicitly incorporates herein each and every specific member and combination of sub-ranges therein whatsoever. Thus, any specified range or group is to be understood as a shorthand way of referring to each and every member of a range or group individually as well as each and every possible sub-ranges or sub-groups encompassed therein; and similarly with respect to any sub-ranges or sub-groups therein.

As used herein, the term "block" or "inhibit" refers to a decrease in one or more given measurable activity by at least 10% relative to a reference and/or control. Where inhibition is desired, such inhibition is preferably at least 20%, 30%, 40%, 50%, 60%, 70%, 80%, 90% or more, up to and including 100%, i.e., complete inhibition or absence of the given activity. As used herein, the term "substantially inhibits/blocks" refers to a decrease in a given measurable activity by at least 50% relative to a reference. For example, "substantially inhibits" refers to a decrease in a given measurable activity of at least 50%, 55%, 60%, 65%, 70%, 75%, 80%, 85%, 90%, 95% and up to and including 100% relative to a reference. As used herein, "blocks/prevents/inhibits/impairs/lowers the interaction", with reference to the binding of a ligand that binds to a receptor refers to a decrease in binding by at least 10% relative to a reference. An agent may block the binding of a ligand to a receptor-expressing cells. "Inhibits the interaction" and/or "block the binding" preferably refers to a decrease in binding of at least 20%, 30%, 40%, 50%, 60%, 70%, 80%, 90% or more, up to and including 100%. A "receptor" as provided for herein means PILRa or PILRb. A "ligand" as provided for herein is selected from NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA. A general feature of a ligand is glycan modification, e.g., sialidated glycans.

A "composition" of the invention including an agent may be manufactured in a conventional manner. In particular, it is formulated with a pharmaceutically acceptable diluent or carrier, e.g., water or a saline solution such as phosphate buffer saline. In general, a diluent or carrier is selected on the basis of the mode and route of administration, as well as standard pharmaceutical practice. Therapeutic compositions typically must be sterile and stable under the conditions of manufacture and storage. The composition can be formulated as a solution, microemulsion, liposome, or other ordered structure suitable to high drug concentration. The proper fluidity can be maintained, for example, by the use of a coating such as lecithin, by the maintenance of the required particle size in the case of dispersion and by the use of surfactants. In many cases, it may be preferable to include isotonic agents, for example, sugars, polyalcohols such as mannitol, sorbitol, or sodium chloride in the composition. Prolonged absorption of compositions may be brought about by including in the composition an agent which delays absorption, for example, monostearate salts and gelatin. Moreover, an agent of the invention may be administered in a time release formulation, for example in a composition which includes a slow release polymer. The active agents may be prepared with carriers that will protect the agent against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the relevant art. The present invention relates to compositions that may comprise an agent capable of modulating PILR (e.g., PILRa or PILRb) activity and a pharmacologically acceptable carrier. In one embodiment, such compositions include an agent that may block the interaction between a ligand and PILRa to treat an PILRa-related disease (for example an immune-related disease and/or inflammatory disease and/or microbial infection).

As used herein "pharmaceutically acceptable carrier" or excipient includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier may be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media is incompatible with the active agent, use thereof in the pharmaceutical compositions of the invention is contemplated. Supplementary active compounds may also be incorporated into the compositions.

"Administration" of a composition may be performed by any suitable routes. Such routes may include parenteral, pulmonary, nasal and/or oral routes. In one embodiment, the pharmaceutical composition may be intra-muscular (IM), subcutaneous (SC), intra-dermal (ID), intra-venous (IV) and/or intra-peritoneal (IP) routes using any suitable means.

The term "effective amount" is intended to mean an amount of an agent sufficient to substantially block the interaction between a ligand (as defined herein) and PILR (e.g., PILRa or PILRb). An effective amount may also encompass either "therapeutically effective amount" and/or "prophylactically effective amount". A "therapeutically effective amount" refers to an amount effective, at dosages and for periods of time necessary, to achieve the desired therapeutic result, such as a reduction in disease progression and/or alleviation of the symptoms associated with a disease. A therapeutically effective amount of modulators of a PILR activity may vary according to factors such as the disease state, age, sex, and weight of the individual, and the ability of the agent to elicit a desired response in the individual. Dosage regimens may be adjusted to provide the optimum therapeutic response. A therapeutically effective amount is also one in which any toxic or detrimental effects of the agent are outweighed by the therapeutically beneficial effects. A "prophylactically effective amount" refers to an amount effective, at dosages and for periods of time necessary, to achieve the desired prophylactic result, such as preventing and/or inhibiting (reducing) the rate of disease onset or progression. A prophylactically effective amount may be determined as described above for the therapeutically effective amount. For any particular subject, specific dosage regimens may be adjusted over time according to the individual need and the professional judgment of the person administering of the compositions.

During inflammation, various molecules may be secreted by cells. Such molecules may be referred to as "inflammatory mediators". As will be appreciated by one skilled in the art, these inflammatory mediators may be, for example and without limitation, amines, eicosanoids, growth factors, reactive oxygen species, enzymes (for example a proteinase), chemokines, cytokines, etc.

Measuring the binding of a ligand (as defined herein) to PILRa may be performed using (without limitation) such suitable assays as quantitative comparisons comparing kinetic and equilibrium binding constants. The kinetic association rate ($k_{on}$) and dissociation rate ($k_{off}$), and the equilibrium binding constants ($K_d$) may be determined using surface plasmon resonance on a BIAcore™ instrument following the standard procedure in the literature. Binding properties of these interactions may also be assessed by flow cytometry and/or by solid phase binding assay.

The present invention also relates to a method of identifying a compound capable of blocking the interaction between a ligand and PILRa; the method may comprise measuring a ligand-mediated PILRa activity in the presence or absence of the agent, wherein a lower PILRa activity in the presence of the agent may be indicative that the agent is blocking the interaction between a ligand and PILRa.

As used herein, "an activity mediated by a ligand" or "a ligand-mediated PILRa activity" is an activity involving or resulting from the binding of a ligand to PILRa, and includes, but is not limited to, binding to PILRa, the induction of T cells to produce and secrete cytokines (for example IL-2, IL-10, IFN-γ and TNF-α), the synthesis of inflammatory molecules (inflammatory mediators) such as IL-6, IL-8 and metalloproteinases and T-cell proliferation (or inhibition thereof), etc. It will be understood that the ligand-mediated activity may depend on the specific ligand, e.g., NPCD1, BR3, etc., being evaluated.

In an embodiment the use may be for the treatment or prevention of inflammatory-related diseases or condition, or a microbial infection in the subject.

One of skill in the art will recognize that while the some definitions have been written with reference to a specific polypeptide they are equally applicable to other polypeptides described herein.

Although various embodiments of the invention are disclosed herein, many adaptations and modifications may be made within the scope of the invention in accordance with the common general knowledge of those skilled in the relevant art. Such modifications include the substitution of known equivalents for any aspect of the invention in order to achieve the same result in substantially the same way. Furthermore, numeric ranges are inclusive of the numbers defining the range. In the claims, the word "comprising" is used as an open-ended term, substantially equivalent to the phrase "including, but not limited to". The following examples are illustrative of various aspects of the invention, and do not limit the broad aspects of the invention as disclosed herein.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); kg (kilograms); μg (micrograms); L (liters); ml (milliliters); μl (microliters); cm (centimeters); mm (millimeters); μm (micrometers); nm (nanometers); ° C. (degrees Centigrade); h (hours); min (minutes); sec (seconds); msec (milliseconds); Ci (Curies) mCi (milliCuries); μCi (microCuries); TLC (thin layer achromatography); CIA (Collagen Induced Arthritis); EAE (Experimental allergy encephalitis); AIA (Antibody induced arthritis); DTH (Delayed Type Hypersensitivity)

EXAMPLES

The present invention is described in further detain in the following examples which are not in any way intended to limit the scope of the invention as claimed. The attached Figures are meant to be considered as integral parts of the specification and description of the invention. All references cited are herein specifically incorporated by reference for all that is described therein. The following examples are offered to illustrate, but not to limit the claimed invention.

Cells and Reagents used in the Examples were as follows: All transfections were performed with Fugene 6 (Roche) or Lipofectamine 2000 (Invitrogen) according to the manufacturers protocol. Mouse total RNA adult tissue panel was purchased from Zyagen (San Diego, Calif.). Recombinant human cytokines were from Peprotech (Rocky Hill, N.J.). The following anti-mouse antibodies were used for flow cytometry: anti-mPILRa, anti-mCD99 and anti-mCOLEC12 are all from R&D Systems (Minneapolis, Minn.), anti-FLAG (M2) monoclonal antibody was purchased from Sigma-Aldrich and labeled with Alexa Flour-647 monoclonal antibody labeling kit from Invitrogen, and anti-mouse IgG2a-FITC was from BD Biosciences (San Jose, Calif.).

Example 1

Recombinant Production of PILR, Ligands and Antibodies Thereof

This example illustrates preparation of potentially glycosylated forms of the desired ligands or PILR proteins (either of which is referred to in this example as a desired protein) by recombinant expression in mammalian cells. Preparations of PILR antibodies are also described.

The vector, pRK5 (see EP 307,247, published Mar. 15, 1989), was employed as the expression vector in all instances. Optionally, DNA encoding the desired protein was ligated into pRK5 with selected restriction enzymes to allow insertion of such DNA using ligation methods such as described in Sambrook et al., supra. Epitope-tagged variants of the desired protein may also be expressed in cells. The DNA encoding the desired protein was ligated into pRK5 containing the desired epitope tag (poly-His, FLAG, human IgG$_1$ Fc) in frame with the desired epitope tag.

The predicted extracellular domains of human and mouse PILR were cloned without the transmembrane domain into the pRK5 vector containing a C-terminal human IgG$_1$-Fc or 8×-His tag, or with the transmembrane domain into the pRK5 vector containing a C-terminal GFP tag.

Soluble forms of these proteins were produced in a CHO cell transient transfection and purified by affinity chromatography using anti-FLAG (M2) agarose affinity gel (Sigma-Aldrich) for FLAG-tagged proteins, Ni-NTA agarose (Qiagen) for 8×-His-tagged proteins, or protein-A Sepharose (Amersham Pharmacia) for IgG$_1$-Fc fusion proteins. Proteins were further separated from aggregates and contaminants with a Superdex 200 gel-filtration column and/or MonoQ/S ion exchange columns (Amersham). Protein purity was assessed by SDS-PAGE followed by SimplyBlue Safe Stain (Invitrogen) and purified proteins were aliqouted and frozen at −80° C. until needed.

In one embodiment, the selected host cells may be HEK293T cells. Human 293 cells (ATCC® CCL 1573) were grown to 50-80% confluence in tissue culture plates in medium such as DMEM supplemented with fetal calf serum and optionally, nutrient components and/or antibiotics. 1-10 μg of DNA encoding the desired protein ligated into pRK5 was introduced into HEK293T cells using commercially available transfection reagents SUPERFECT® (QIAGEN®), LIPOFECTAMINE® (INVITROGEN®) or FUGENE® (ROCHE®) according to manufacturer's instructions. 18-24 hours after the transfections, the culture medium was removed and tested in selected bioassays or cells were harvested using 10 mM EDTA in 20 mM Na phosphate buffer, pH7.4, and tested in selected bioassays.

Stable expression of the desired protein was achieved in HEK293T cells by cloning DNA encoding the desired protein into pRK5 vector with a selection marker that confers resistance to the antibiotic GENETICIN®. For stable expression of desired proteins, cells were transfected as described and allowed to grow in DMEM with a concentration of GENETICIN® that would permit growth of cells in which the desired vector had integrated into the genome (1-0.5 μg/ml).

In another embodiment, the epitope tagged versions of the desired protein can be expressed in host CHO cells. Twelve micrograms of the desired plasmid DNA was introduced into approximately 10 million CHO cells using commercially available transfection reagents SUPERFECT® (QIAGEN®), DOSPER®, LIPOFECTAMINE® (INVITROGEN®) or FUGENE® (Boehringer Mannheim) according to manufacturer's instructions. The cells are grown as described in Lucas et al. (*Nucl. Acids Res.* (1996) 24:9 1774-1779). Approximately $3 \times 10^{-7}$ cells are frozen in an ampule for further growth and production as described below.

The ampules containing the plasmid DNA are thawed by placement into a water bath and mixed by vortexing. The contents are pipetted into a centrifuge tube containing 10 mLs of media and centrifuged at 1000 rpm for 5 minutes. The supernatant was aspirated and the cells were resuspended in 10 mL of selective media (0.2 μm filtered PS20 with 5% 0.2 μm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3 \times 10^5$ cells/mL. The cell media was exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner was seeded at $1.2 \times 10^6$ cells/mL. On day 0, the cell number and pH was determined. On day 1, the spinner was sampled and sparging with filtered air was commenced. On day 2, the spinner was sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH was adjusted as necessary to keep it at around 7.2. After 10 days, or until the viability dropped below 70%, the cell culture was harvested by centrifugation and filtering through a 0.22 μm filter. The filtrate was either stored at 4° C. or immediately loaded onto columns for purification.

For the poly-His tagged constructs, the proteins are purified using a Ni-NTA column (Qiagen). Before purification, imidazole was added to the conditioned media to a concentration of 5 mM. The conditioned media was pumped onto a 6 ml Ni-NTA column equilibrated at 4° C., in 20 mM Hepes, pH 7.4, buffer containing 0.3 M NaCl and 5 mM imidazole at a flow rate of 4-5 ml/min. After loading, the column was washed with additional equilibration buffer and the protein eluted with equilibration buffer containing 0.25 M imidazole. The purified protein was then run over a Superdex S200 gel filtration column and/or a MonoQ/S ion exchange column (Applied Biosystems) to remove aggregated or proteolysed protein or any contaminants and subsequently concentrated and dialyzed into PBS. The homogeneity was assessed by SDS polyacrylamide gels and by N-terminal amino acid sequencing by Edman degradation. Proteins were stored at −80° C. until used in bioassays.

For the FLAG-epitope tagged constructs, the proteins are purified using an anti-FLAG (M2) agarose column (Sigma). The conditioned media was pumped onto a 6 ml anti-FLAG column equilibrated at 4° C. with 20 mM Na phosphate buffer, pH 7.4. After loading, the column was washed extensively with equilibration buffer before elution with 100 mM citric acid, pH 3.5. The eluted protein was immediately neutralized by collecting 1 ml fractions into tubes containing 275 μL of 1 M Tris buffer, pH 9. The highly purified protein was subsequently run over size exclusion chromatography, dialyzed, analyzed, and stored as above for the poly-His tagged proteins.

Immunoadhesin (Fc-containing) constructs are purified from the conditioned media as follows. The conditioned medium was pumped onto a 5 ml Protein A column (Pharmacia) which had been equilibrated in 20 mM Na phosphate buffer, pH 7.4. After loading, the column was washed extensively with equilibration buffer before elution with 100 mM citric acid, pH 3.5. The eluted protein was immediately neutralized by collecting 1 ml fractions into tubes containing 275 pt of 1 M Tris buffer, pH 9. The highly purified protein was subsequently run over size exclusion chromatography, dialyzed, analyzed, and stored as above for the poly-His tagged proteins.

4 to 6-week-old Armenian hamsters (Cytogen) or mice were immunized with 2 μg/injection each murine and human recombinant PILRα proteins. The immunogens are resuspended in monophosphoryl lipid A/trehalose dicorynomycolate adjuvant and injected via footpad or I.P. at 3 to 4 day intervals for a total of 10 boosts. Three days after the final boost, lymphocytes from immunized hamster spleens and lymph nodes were harvested for fusion with SP2/0 myeloma cells (American Type Culture Collection) by using the Cyto Pulse CEEF-50 apparatus (Cyto Pulse Sciences). Briefly, after washing twice with Cytofusion Medium C (Cyto Pulse Sciences), the isolated lymphocytes and SP2/0 cells were mixed at a 1:1 ratio and then resuspended at 10 million cells/ml in Cytofusion Medium C, electrofusion was performed according to manufacturer's guidance. Fused cells were cultured in ClonaCell-HY Medium C (StemCell Technologies) overnight at 37° C. in a 7% $CO_2$ incubator. The next day, fused cells were centrifuged and resuspended in 10 ml ClonaCell-HY Medium C and then gently mixed with 90 ml Methylcellulose-based ClonaCell-HY Medium D (StemCell Technologies) containing HAT components. The fused cells were plated into 100 mm Petri dishes (Becton Dickinson) and allowed to grow in 37° C. in a 7% $CO_2$ incubator. After 7-10 days incubation, the single hybridoma clones were picked by ClonePix (Genetix, United Kingdom) and transferred into 96-well cell culture plates (Becton Dickinson) with 200 μL/well ClonaCell-HY Medium E (StemCell Technologies). Hybridoma culture media was changed prior to ELISA screening. All ELISA positive clones were further screened by FACS. After at least 2 rounds of single cell subcloning by limiting dilution, final clones were scaled up and the supernatants were collected for antibody purification. The hybridoma supernatants were purified by Protein A affinity chromatography, then sterile filtered (0.2 μm pore size, Nalgene Nunc International, NY, USA) and stored at 4° C. in PBS. The purified mAbs were confirmed by ELISA and FACS before testing on functional assays. The isotypes of purified mAbs were determined by the mouse monoclonal antibody isotyping kit from Roche Diagnostics Corporation. The isotypes of purified hamster mAbs were determined by ELISA.

Example 2

Sialidation of PILRa Ligands

Figure 5B:
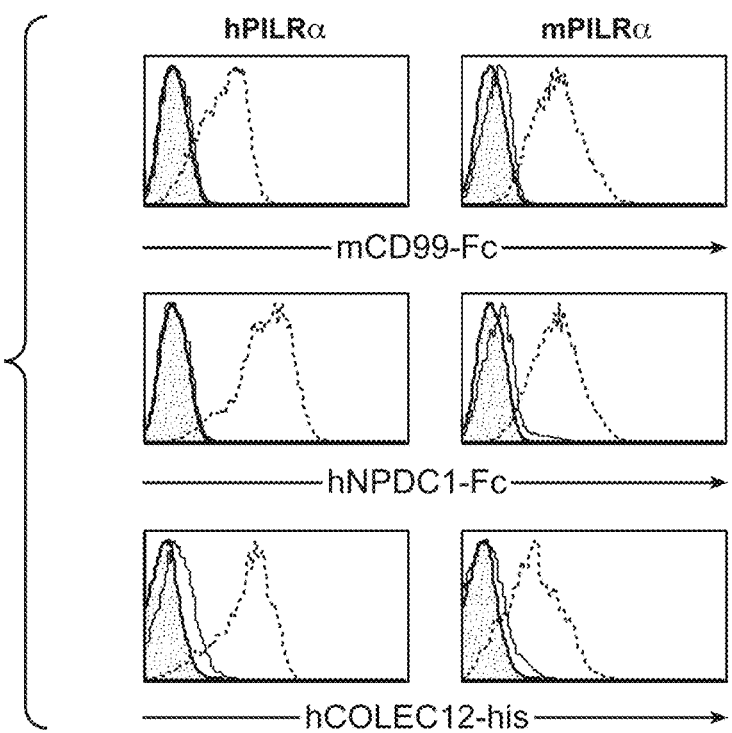
Figure 5C:
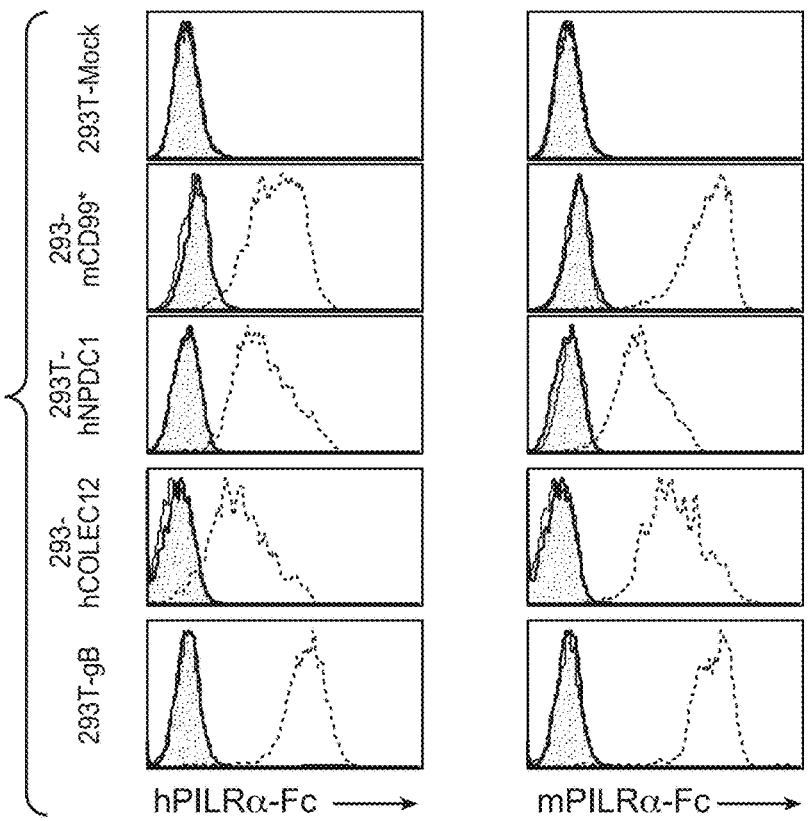
Figures 1, 5D:
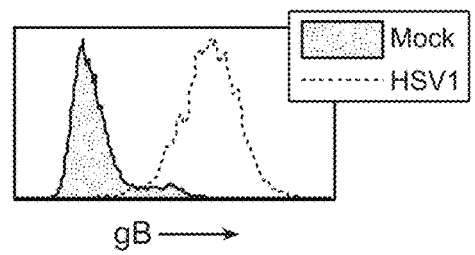

This example uses one PILRa ligand, mCD99, to illustrate the importance of sialidation on the ligand for PILRα binding. Mouse PILRα binds to mCD99 with relatively low affinity, however, it is unclear whether PILRα can bind human CD99. Shiratori et al. (2004) *J Exp Med* 199, 525-533; Tabata et al. (2008) *J Biol Chem* 283, 8893-8901. To test this, we expressed mouse or human CD99 in 293T cells to see whether they can bind to PILRα-mIgG2a (PILRα-Fc) fusion proteins. We found both mouse and human PILRα-Fc fusions bound mCD99 transfectants. However, neither protein bound to hCD99 transfectants (FIG. 1 A). This suggests that the CD99 interaction with PILRα is not conserved at least across human and mouse species. However a conserved PILRα interaction domain between mouse and human PILRα could mediate its binding to mCD99.

Figure 1B:
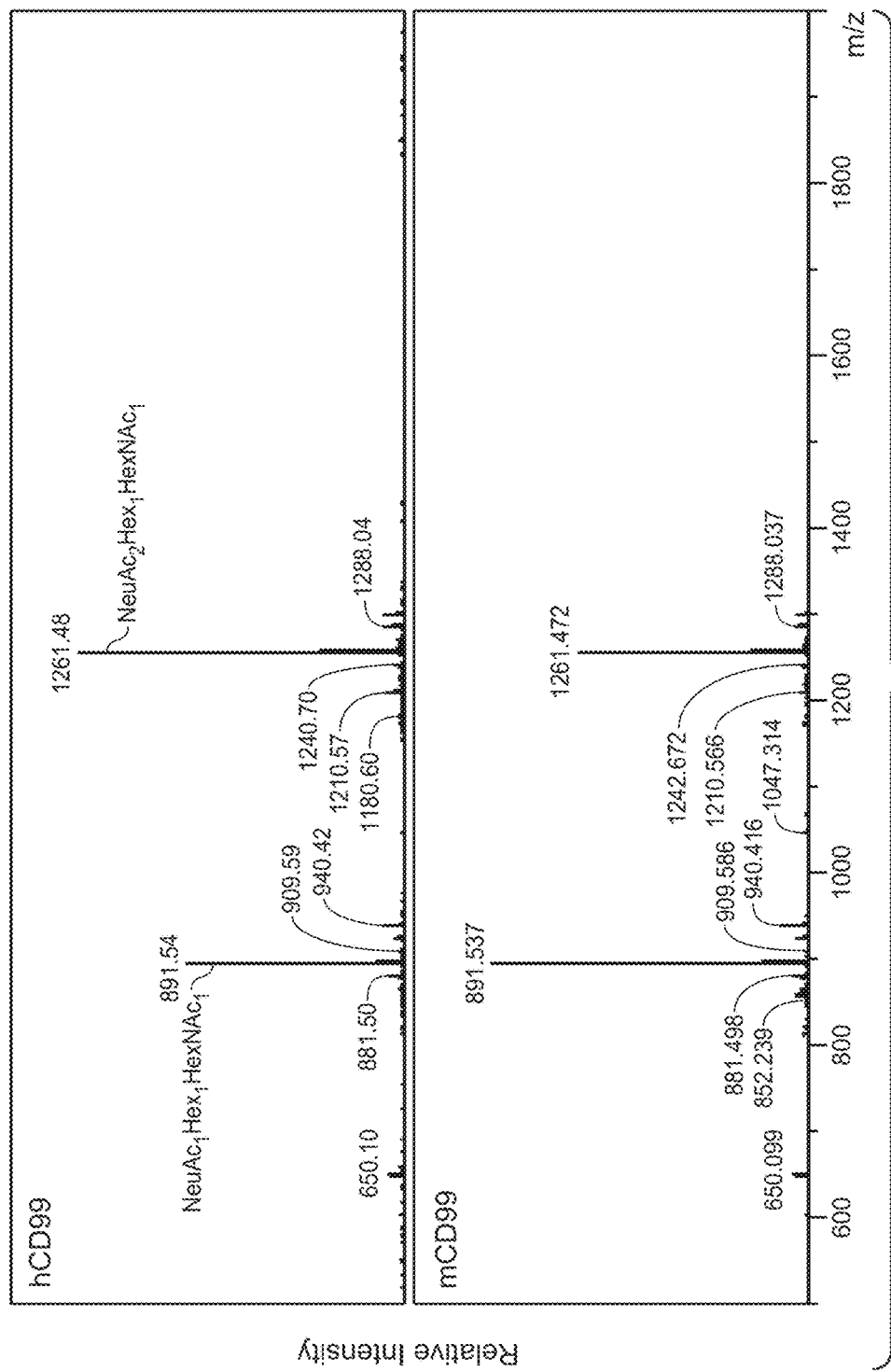
Figure 1D:
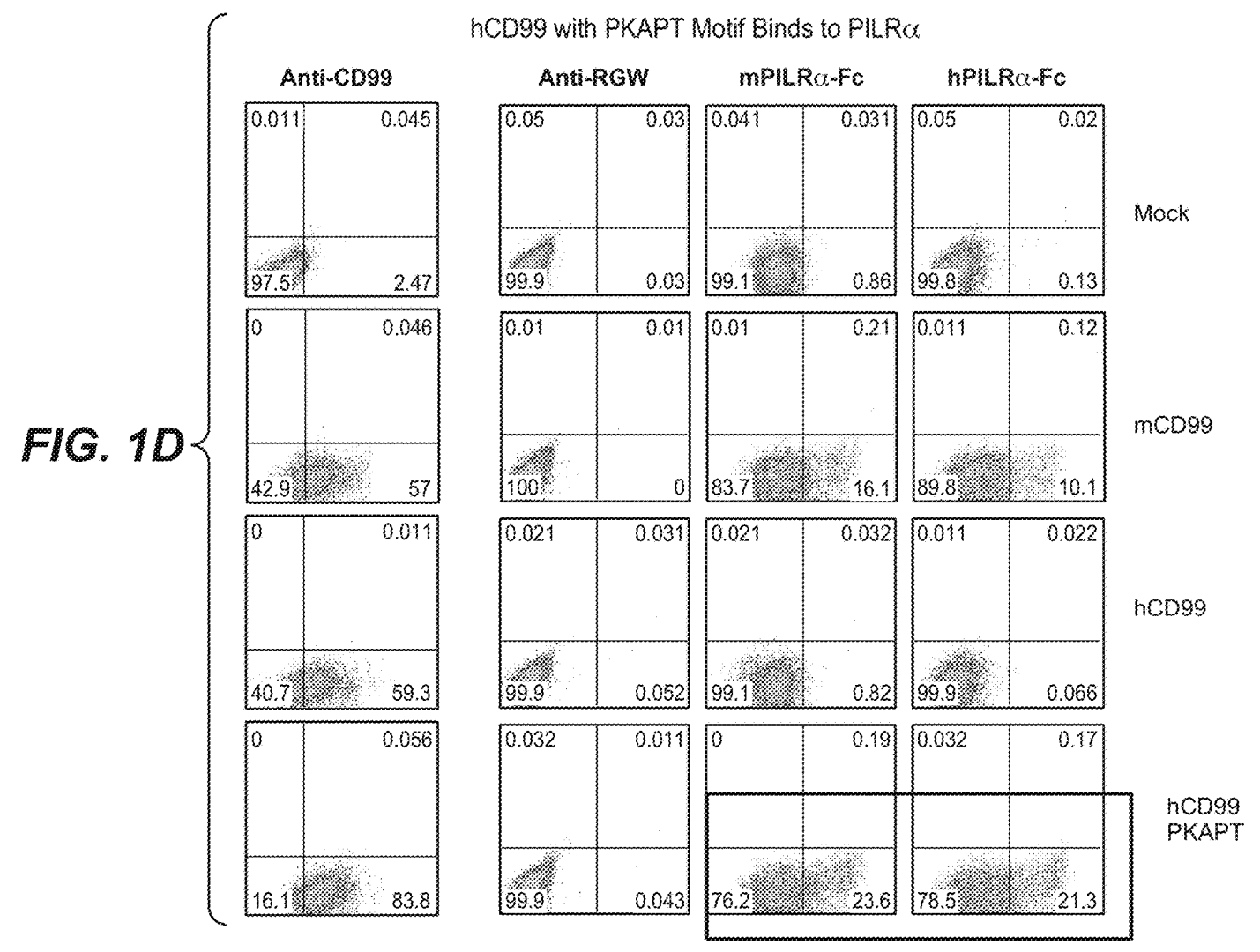
Figure 1E:
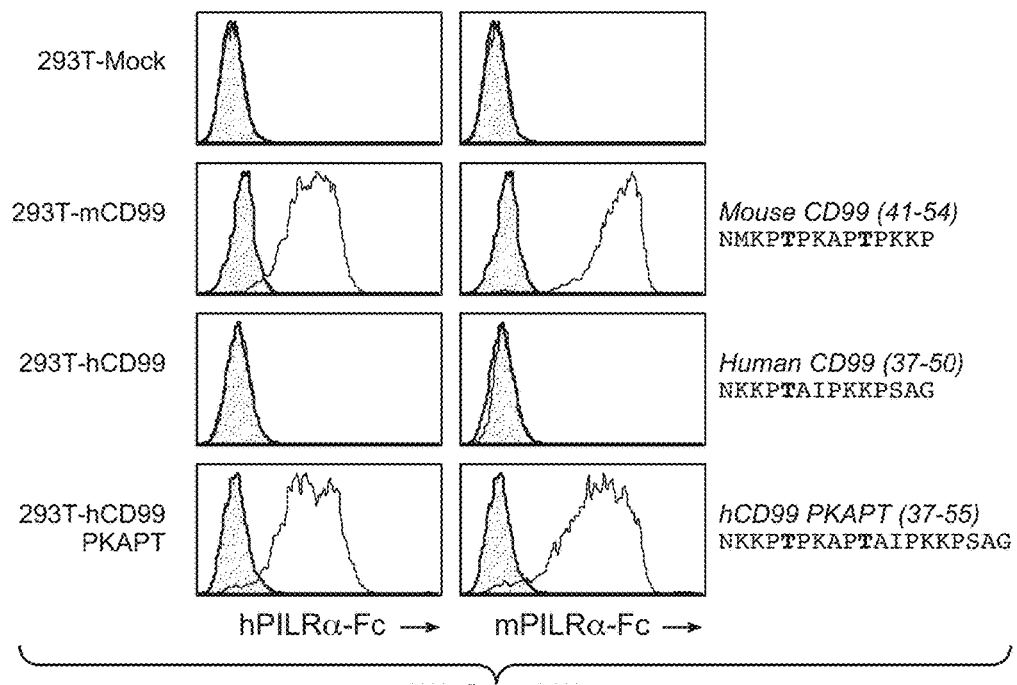

The differential binding of mouse and human CD99 to PILRα may be the result of the low sequence identity between CD99 homologs (about 41% in the extracellular domain) or the differences in glycosylation (type and/or a number of glycans). It has been shown that sialylated O-linked glycans in mCD99 play an essential role in PILRα binding to mCD99. Wang et al. (2008) *J Immunol* 180, 1686-1693. hCD99 has been reported to be O-glycosylated, and similarly to mCD99, does not have any potential N-glycosylation sites. Gelin et al. (1989) *EMBO J* 8, 3253-3259. Lack of binding of PILRα to hCD99 may therefore be related to the differences in its O-glycosylation pattern. To examine this possibility, we first compared profiles of O-glycans from human and mouse CD99-Fc fusion proteins. O-glycans were released by reductive β-elimination and permethylated prior to analysis by MALDI-TOF MS. Comparison of MALDI-TOF spectra (FIG. 1B), demonstrated qualitatively similar O-glycosylation profiles of human and mouse CD99. Two major mono- and di-sialylated O-glycans, having the following compositions: $NeuAc_1Hex_1HexNAc_1$ and $NeuAc_2Hex_1HexNAc_1$, were detected in both proteins. The composition of observed O-glycans is consistent with the presence of sialylated Galβ1-3GalNAc core 1 structures. North et al. (2010) *J Biol Chem* 285, 5759-5775; Olson et al. (2005) *Glycobiology* 15, 177-191.

Since O-glycans of human and mouse CD99 did not differ qualitatively, we next examined whether there might be a difference in the number of O-glycans present on each of the proteins. LC-MS analysis of reduced fusion proteins (with and without PNGase F and Sialidase digestion) showed that hCD99-Fc carried two O-glycans and mCD99-Fc carried three O-glycans with the following composition: $NeuAc_{1-2}Hex_1HexNAc_1$. In the case of mCD99, two adjacent O-glycosylation sites, Thr-45 and Thr-50 (NMKP$\underline{T}^{45}$PKAP$\underline{T}^{50}$PKKPS; SEQ ID NO: 64) are relevant for PILRα recognition. Wang et al. (2008). Sequence alignment of human and mouse CD99 showed that Thr-41 of hCD99 corresponds to the Thr-45 O-glycosylation site of mCD99 and that hCD99 lacks the second potential O-glycosylation site corresponding to Thr-50 of mCD99. Therefore, we performed LC-MS tryptic peptide mapping of hCD99-Fc to determine the localization of O-glycans and to examine whether the peptide containing Thr-41 is indeed O-glycosylated. Two sialylated glycopeptides with following sequence were detected: APDGGFLDLSDALPDNENKKPTAIPK (hCD99-derived; SEQ ID NO: 65) and GPTIKPCPPCK (mIgG2a Fc-derived; SEQ ID NO: 66). Each glycopeptide was glycosylated with a single $NeuAc_{1-2}Hex_1HexNAc_1$ O-glycan. The presence of two sialylated glycopeptides was consistent with the LC-MS analysis of reduced hCD99-Fc. The detected sialoglycopeptide APDGGFLDL SDALPDNENKKP$\underline{T}^{41}$AIPK (SEQ ID NO: 65) contained Thr-41 corresponding to Thr-45 O-glycosylation site of mCD99 and a Ser residue which potentially could be O-glycosylated. However, the exact site of O-glycosylation could not have been sequenced through the performed type of LC-MS experiment. The presence of an O-glycan on the GPTIKPCPPCK (SEQ ID NO: 66) peptide is consistent with the previous report of it being O-glycosylated in the truncated version of mouse IgG2a. Masuda et al. (1999) *Mol Immunol* 36, 993-1003.

Our results indicated that human and mouse CD99 have similar O-glycans but that the presence of a common core of 1 $NeuAc_{1-2}Hex_1HexNAc_1$ O-glycan per se on hCD99 is not sufficient for PILRα binding. A major difference between the mouse and human CD99 O-glycan modifications is that mCD99 has two O-glycosylation sites (Thr-45 and Thr-50) versus one in the human counterpart. Wang et al. (2008). We asked whether the introduction of the mCD99 region $P^{46}KAPT^{50}$ (PKAPT) into hCD99 can confer the binding of PILRα to hCD99. We expressed full-length mCD99, hCD99 and hCD99PKAPT in 293T cells, and again tested the binding of hPILRα-Fc or mPILRα-Fc by FACS. We found that the insertion of mCD99 PKAPT motif into hCD99, directly following the Thr-41 O-glycosylation site, was able to induce binding of human or mouse PILRα to hCD99PKAPT expressing cells. Surprisingly, this interaction was similar in magnitude to human or mouse PILRα binding to mCD99. This suggests the sialylated O-glycans are required for CD99 binding to PILRα (FIG. 1 C).

Example 3

Identification of Novel PILRa Ligands

This example demonstrates the identification of novel ligands for PILRa.

It has been shown that mCD99, HSV1 glycoprotein B and PANP are PILRα ligands. CD99 is expressed on T-cells, B-cells, NK cells, monocytes and neutrophils. However, hPILRa is expressed predominately in cells of the myelo-monocytic lineage, including monocytes/macrophages, granulocytes, and dendritic cells (DC). Discordant PILRa-Fc binding and CD99 expression as well as a low affinity interaction with CD99 (2.2 mM) suggested that there may be additional ligands for PILRa. To identify novel PILRa ligands and to further investigate the nature of PILRα interactions with its ligands as well as biological functions thereof, a cDNA expression library was screened with an Alkaline phosphatase (AP)-tagged PILRα construct.

The extracellular domains of hPILRα (Met1-196Thr) and mPILRα (Met1-197Val) were cloned into the expression vector pRK5 as fusions to C-terminal alkaline phosphatase (AP) tag. 293T cells were transfected with PILRα-AP-pRK5 constructs and Fugene 6 Transfection Reagent (Roche) according to the manufacturer's instructions. Three days after transfection, supernatants were collected for screening. COS7 cells were plated in a 24-well format and transfected with 10 ul of Origene library DNA (Origene, human DNA library containing 20 k genes) per well with Fugene 6 Reagent. Two days later, cells were incubated with human or mouse PILRα-Ap supernatants for 45 min at room temperature (RT). Then cells were fixed with 4% PFA for 15 min at RT. After removing fixation buffer, cells were blocked with 100 mM Glycine in HBS (20 mM Hepes, PH7.2, 150 mM NaCl) for 15 min at RT. Cells were then rinsed and incubated in HBS for 90 min at 65° C. HBS was removed and Western Blue Substrate (Promega) was added and color was developed for 30 min to 1 hr.

The resulting positive clones were identified and further analyzed using FACS. The ligands that bound hPILRa are NPDC1, COLEC12, ETBR, CLEC4G, BR3, MAG, IL-2Ra, FceRII, LRRTM4, DAG1, APLP1, PTPRN, WDR31, PSS8, SIGLEC7 and IL15-RA. See FIGS. 6-11. The expression of these newly identified PILRa ligands on various cell types are summarized in FIG. 12.

Figure 2A:
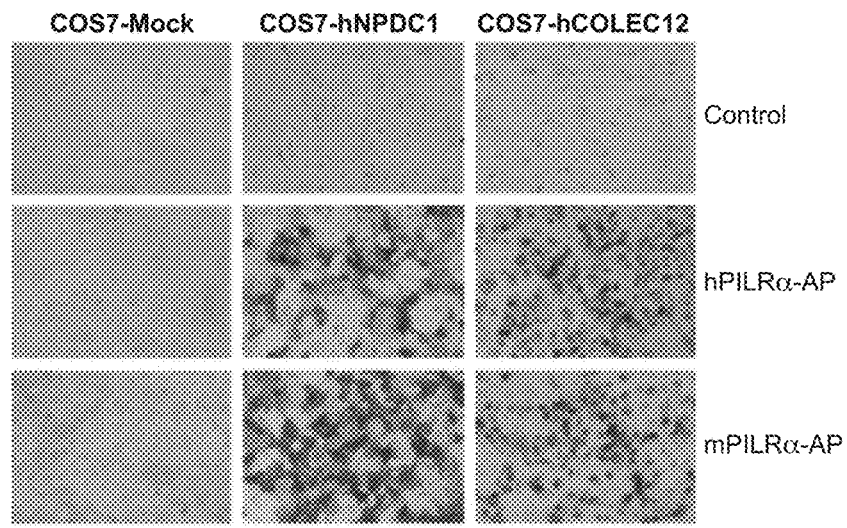
FIGS. 2A-2E illustrate novel PILRα ligands NPDC1 and COLEC12.

The hPILRα-AP binding to human NPDC1 and human COLEC12 expressing cells are subject to further analysis (FIG. 2A). Similar to mCD99, both mouse or human PILRα-AP were able to bind to hNPDC1 and hCOLEC12 expressing cells suggesting that a conserved interaction domain mediates PILRα binding to these ligands. NPDC1 is a type I transmembrane protein and has been identified as a neural-specific gene involved in the control of cell proliferation and differentiation. Galiana et al. (1995) *Proc Natl Acad Sci USA* 92, 1560-1564. COLEC12 is a type II transmembrane collectin family member as also known as collectin placenta 1 (CL-P1) and Scavenger Receptor with C-type Lectin (SRCL) type I. Ohtani et al. (2001) *J Biol Chem* 276, 44222-44228; Nakamura et al. (2001) *Biochem Biophy Res Commun* 280, 1028-1035.

Figure 2B:
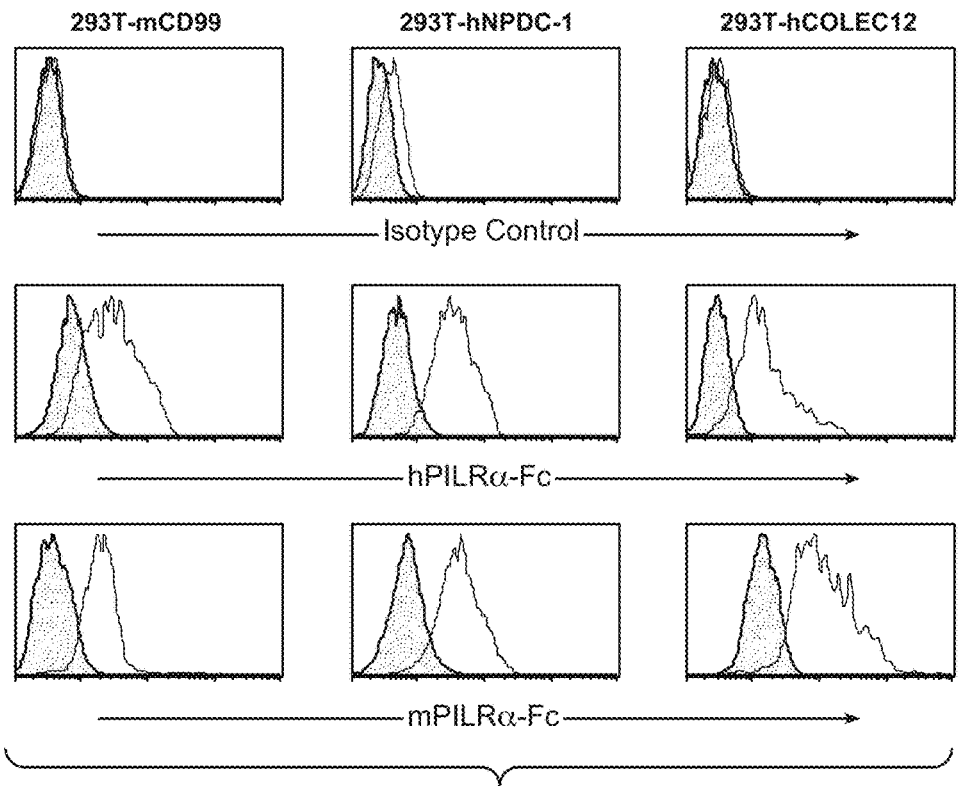
Figure 2C:
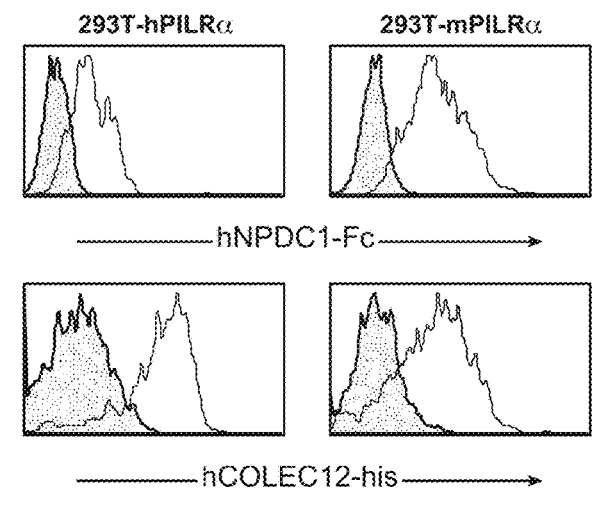
Figure 2D:
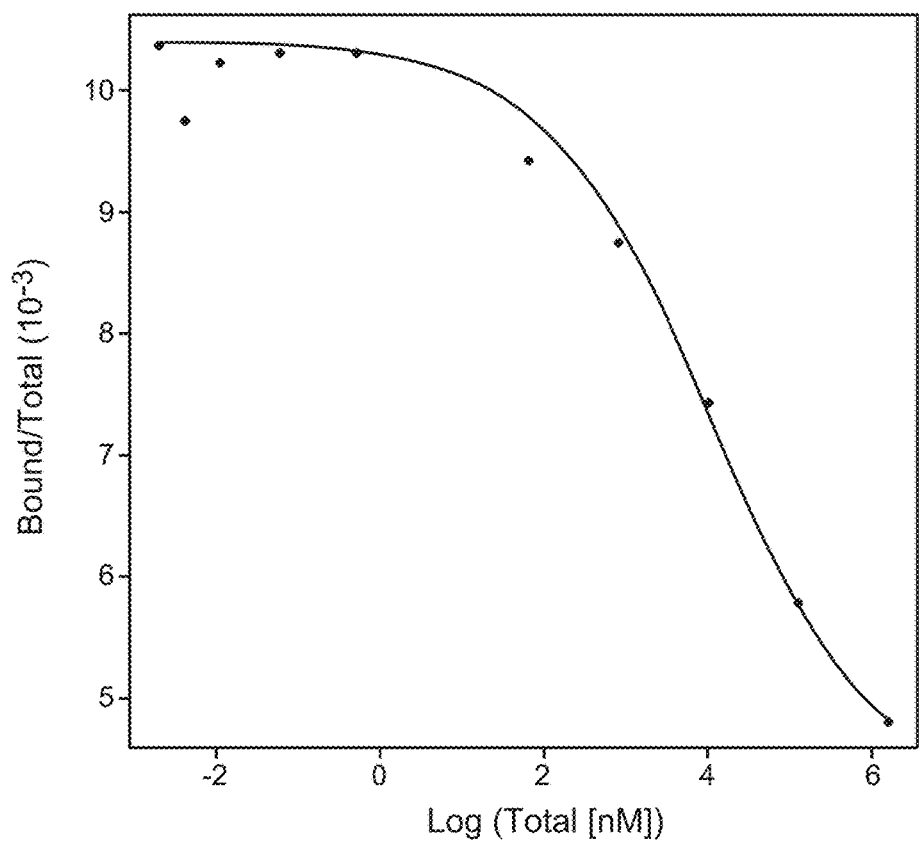
Figure 2E:
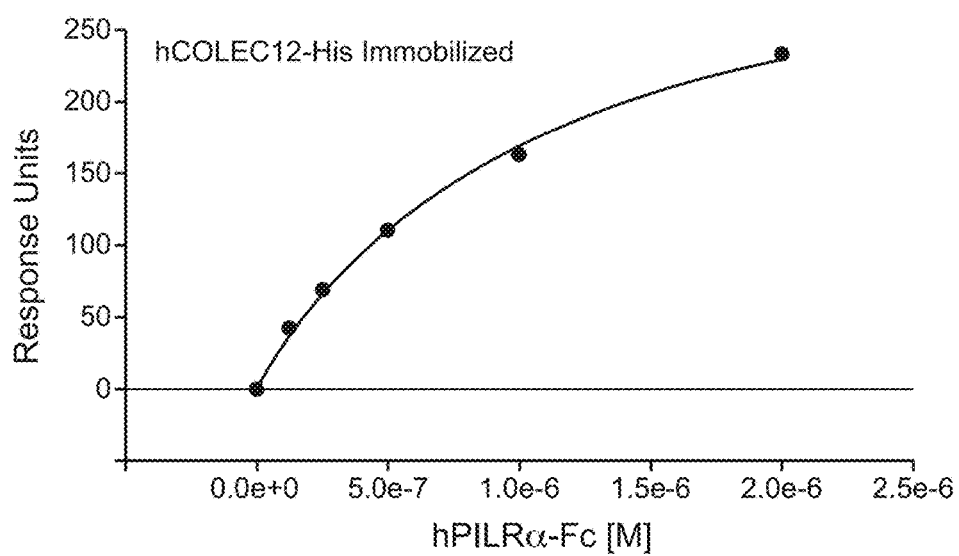

To confirm the binding of PILRα to hNPDC1 and hCOLEC12 on the cell surface, N-terminal flag-tagged hNPDC1 or C-terminal his tagged hCOLEC12 were expressed in 293T cells, and then tested for mPILRα-Fc and hPILRα-Fc binding. Mock transfected cells were used as a negative control and mCD99 transfected cells were used as positive control. Both mPILRα-Fc and hPILRα-Fc bound to mCD99, hNPDC1 and hCOLEC12 expressing cells (FIG. 2B). Similar results were also obtained by hNPDC1-Fc or hCOLEC12-his in PILRα transfectants by FACS analysis. Again, both hNPDC1-Fc and hCOLEC12-his bound to hPILRα as well as mPILRα transfectants, (FIG. 2C). Using an equilibrium competition radioligand assay, the affinity ($K_D$) of hPILRα-Fc binding to cell-surface expressed hNPCD1 was determined to be 49 nM (FIG. 2D). Because the sensitivity of the radioligand competition assay was too low to measure the lower affinity interaction between hPILRα-Fc and hCOLEC12, we used SPR instead (FIG. 2E). Using this method, the equilibrium $K_D$ of this interaction was found to be 1.1 uM. Taken together these studies demonstrate specific binding of PILRα to human NPDC1 and COLEC12.

Figure 3:
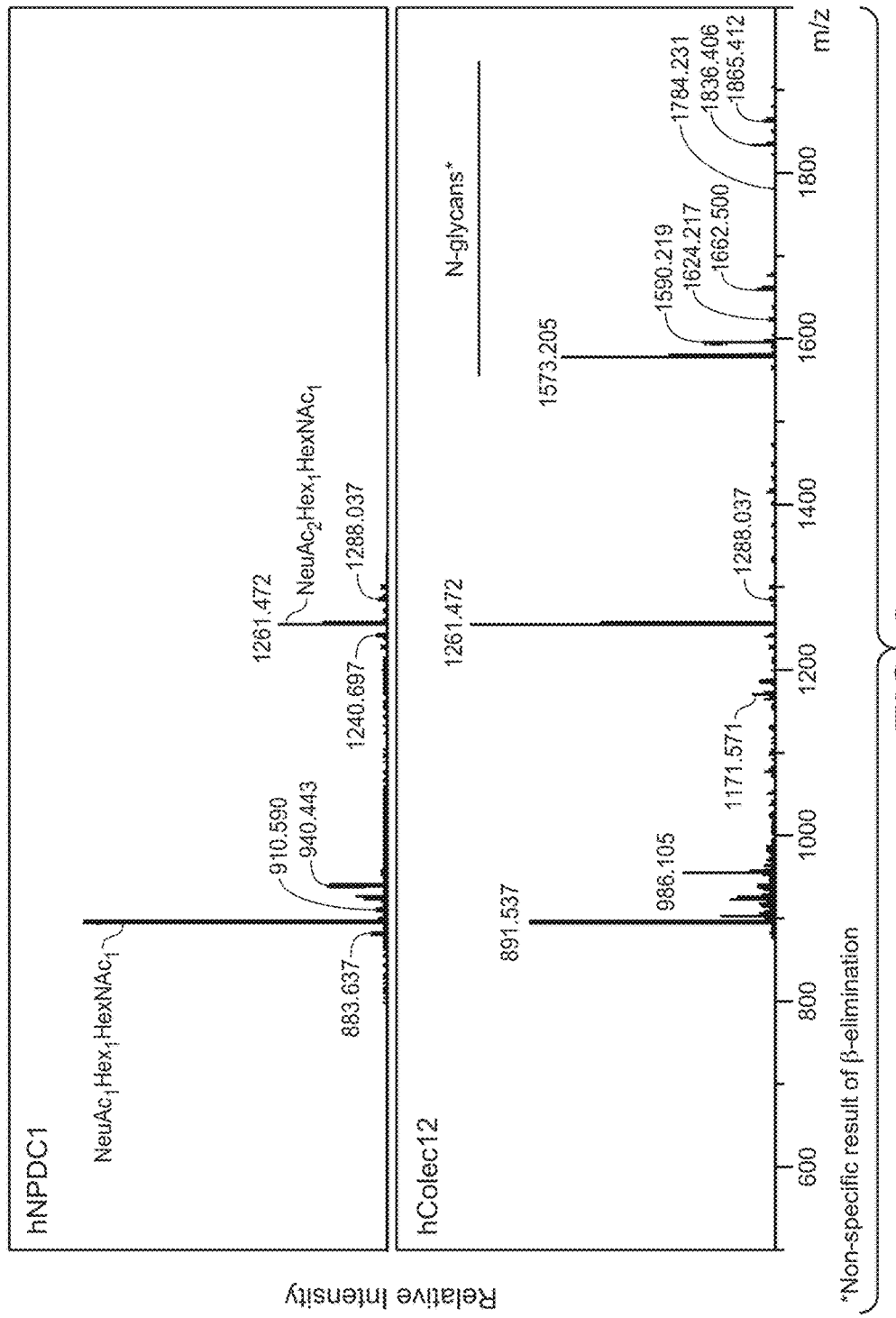
FIG. 3 shows that human NPDC1 and COLEC12 are glycosylated with sialylated glycans. Comparison of MALDI-TOF MS spectra of permethylated O-glycans, released by reductive β-elimination, from human NPDC1-Fc and human COLEC12-his. Molecular ions of permethylated glycans (glycan alditols) were detected in positive ion mode, as sodium adducts $(M+Na)^+$.

The presence of sialylated O-glycans is required for PILRα binding to its known ligands including mCD99, HSV1-gB and the recently identified PANP. Kogure et al. (2011) *Biochem Biophys Res Commun* 405, 428-533; Wang et al. (2008); Wang et al. (2009) *J Virol* 83, 13042-13045. Human NPDC1 and COLEC12 have multiple potential O-glycosylation sites when analyzed using the NetOGlyc 3.1 prediction server. Julenius et al. (2005) *Glycobiology* 15, 153-164. hNPDC1 does not have any potential N-glycosylation sites, while hCOLEC12 has multiple sites. To determine whether both proteins are indeed O-glycosylated, they were analyzed in similar manner to mouse and human CD99. MALDI-TOF MS analysis of permethylated O-glycans released by reductive β-elimination from hNPDC1-Fc and hCOLEC12-his confirmed the presence of O-glycans, qualitatively similar to those determined in mouse and human CD99 (FIG. 3). In addition, analysis of hCOLEC12 by a combination of HPLC charge profiling of fluorescent 2-aminobenzoic acid labeled glycans and MALDI-TOF of permethylated unlabeled glycans also demonstrated its complex N-glycosylation profile. Neutral glycans were mostly of the high-mannose type (predominantly Man-5) and complex afucosylated or core-fucosylated bi-, tri- and tetra-antennary glycans, galactosylated to various degrees. Negatively charged glycans were sialylated (0-4 NANA), complex type bi-, tri- and tetra-antennary N-glycans, core-fucosylated and mostly fully galactosylated.

Figure 4:
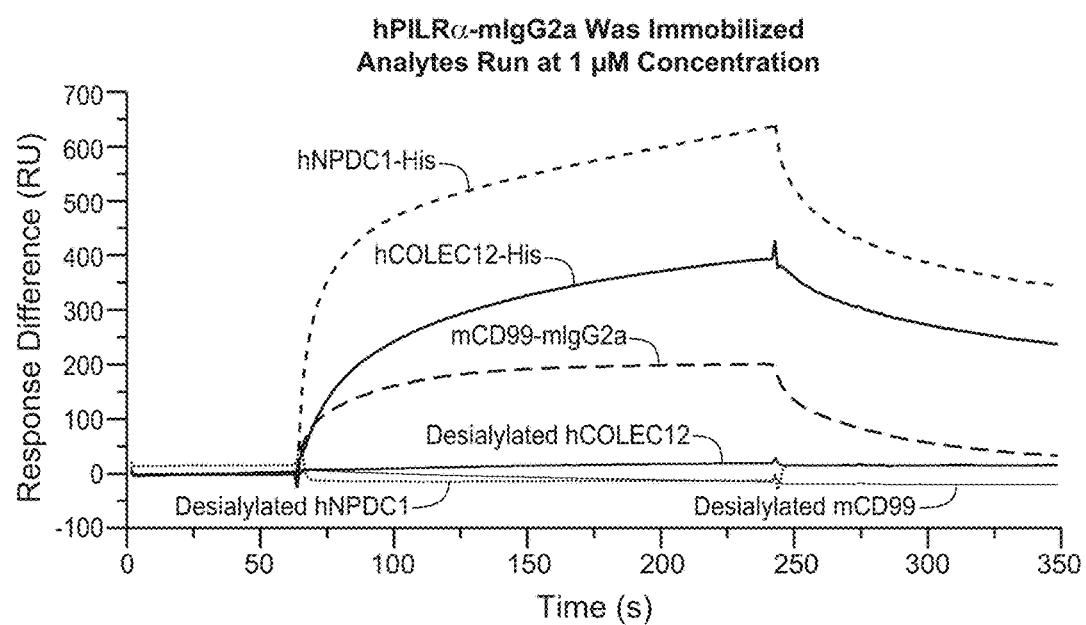
FIG. 4 shows that sialylated glycans on NPDC1 or COLEC12 are required for their binding to PILRα. The binding of selected proteins to hPILRα was determined by surface plasmon resonance. Human PILRα-Fc (25 ug/ml) was immobilized to a CM5 sensor chip. Fusion proteins with and without Sialidase A treatment were used as analytes (1 μM). The difference between the responses of negative control protein and the testing proteins was shown.

In order to test whether sialylated glycans on NPDC1 and COLEC12 are required for their binding to PILRα, we performed Surface Plasmon Resonance analysis using Biacore with hNPDC1 and hCOLEC12 fusion proteins with and without Sialidase A treatment. Before Sialidase A treatment, the proteins showed good binding affinity to hPILRα (FIG. 4). However, after Sialidase A treatment the proteins showed little or no binding to hPILRα (FIG. 4). mCD99 was used as a control and showed similar results to both hNPDC1 and hCOLEC12 (FIG. 4). These studies suggest that the sialyated glycans on hNPDC1 and hCOLEC12 are required for their binding to hPILRα.

Our binding analysis indicates that hNPDC1 binds with higher affinity ($K_D$=49 nM) than hCOLEC12 ($K_D$=1 μM). Although PILRα binds to NPDC1 with relative higher affinity, both hPILRα and mPILRα do not bind to mNPDC1. Similar to CD99, differences in NPDC1 glycosylation may be responsible for this observation. NPDC1 has been identified as a neuronal-specific gene involved in the control of cell proliferation and differentiation. Galiana et al. (1995) *Proc Natl Acad Sci USA* 92, 1560-1564. Our results suggest that PILRα recognizes several ligands, some of which are not conserved between mouse and human. The identification of multiple PILRα ligands in the neuronal system (PANP and NPDC1) suggests that PILRα might play a role in the CNS.

COLEC12 is the only member of the Collectin scavenger receptor family that is expressed as a cell surface transmembrane protein and its ECD contains coiled-coil, collagen-like, and C-type lectin/carbohydrate domains. Ohtani et al. (2001) *J Biol Chem* 276, 44222-44228. COLEC12 is expressed in vascular endothelia cells and monocytes to mediate the uptake of oxidized low density lipoprotein and microbes. Ohtani et al. (2001) *J Biol Chem* 276, 44222-44228; Nakamura et al. (2001) *Biochem Biophys Res Commun* 280, 1028-1035. Interestingly, Collectins have been shown to interact with other inhibitory receptors such as SIRPα to modulate lung pathophysiology. Janssen et al. (2008) *Am J Respir Crit Care Med* 178, 158-167. PILRα is emerging as a receptor that recognizes a specific group of ligands in cellular or pathogenic sources with unique sialic acid pattern. Correspondingly, we found that human and mouse PILRα-Fc fusions bind to mouse thymocytes, peripheral CD8+T and activated CD4+T, B, NK, NKT cells, granulocytes and monocytes, as well as a majority of human PBMC. These data suggest that PILRα ligands are broadly expressed in immune cells. Since the presence of sialylated glycans is a common feature of all known PILRα ligands, it is apparent that PILRα has additional cellular ligands.

Example 4

Conserved PILRα Domain for its Interaction with Diverse Sialylated Ligands

This example demonstrates a conserved domain on PILRa critical for its binding to sialylated ligands.

Figures 2, 5D:
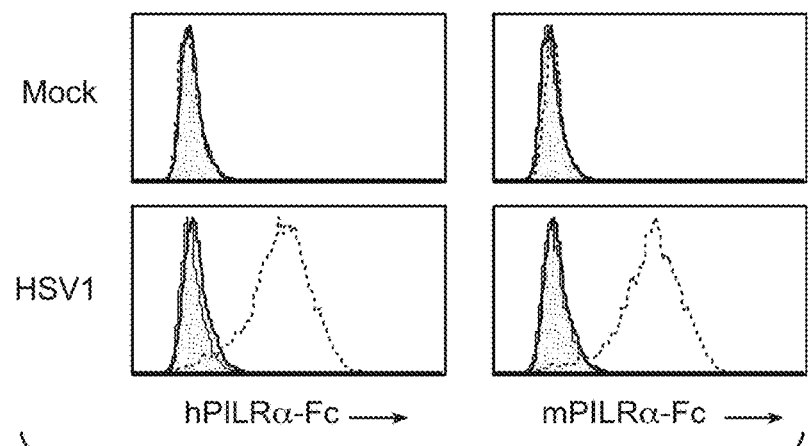

Sialylated glycan modifications appear to be a general feature of all identified PILRα ligands and coincidently few other receptors such as Siglecs. Kogure et al., (2011) *Biochem Biophys Res Commun* 405, 428-433; Wang et al. (2008); Crocker et al. (2007) *Nat Rev Immunol* 7, 255-266; Wang et al. (2009). A conserved Arg site in the ECD of Siglecs plays a critical role in their binding to sialic acid. May et al. (1998) *Mol Cell* 1, 719-728; Ikehara et al. (2004) *J Biol Chem* 279, 43117-43125; Vinson et al. (1996) *J Biol Chem* 271, 9267-9272. The PILRα ECD has two, similar Arg sites (human Arg 96, mouse arginine 103; human R126, mouse R133) that are highly conserved across species (FIG. 5 A). The second Arg site (mouse R133, human R126) corresponds to the critical Arg site that is required for the binding of Siglecs to sialic acid in the ligands. May et al. (1998) *Mol Cell* 1, 719-728. The hPILRα R126 is not an Ig fold stabilizing residue (FIG. 5A). We examined whether mutation of this Arg site in mouse or human PILRα affects their binding to ligands. First, we tested the binding of ligand fusion proteins including mCD99-Fc, hNPDC1-Fc and hCOLEC12-his to cell surface-expressed WT or Arg mutated hPILRαR126A and mPILRαR131A. The Arg mutation did not affect cell surface expression of human and mouse PILRα. We found that all fusion proteins bound to wild type human and mouse transfectants, but none of them bound to hPILRαR126A and mPILRαR133A transfectants (FIG. 5 B), suggesting Arg126 in hPILRα and Arg133 in mouse PILRα are required for PILRα binding to ligands. We also generated WT and Arg mutant human and mouse PILRα-Fc fusion proteins, and examined their binding to cell surface expressed ligands. The result showed that WT human and mouse PILRα-Fc bound to mCD99, hNPDC1, hCOLEC12 and HSV-1 gB transfectants, while hPILRαR126A-Fc and mPILRαR133A-Fc did not bind to these ligand transfectants (FIG. 5C). Glycoprotein B expression could be detected on HSV1 infected cells 24 hrs after infection (FIG. 5D-1), we therefore tested wild type and Arg mutant human and mouse PILRα-Fc binding to HSV1 infected cells. Again, we observed the binding of only WT hPILRα-Fc and mPILRα-Fc but not hPILRαR126A and mPILRαR133A to HSV1 infected 293T cells (FIG. 5D-2). These studies further support that this conserved Arg site is necessary for PILRα binding to its ligands.

Figure 5E:
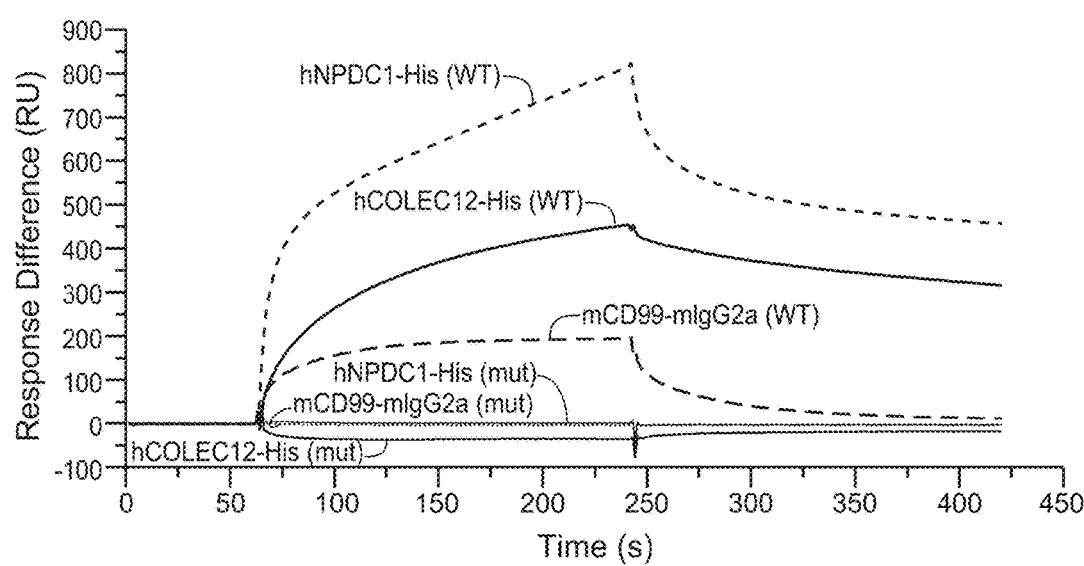

To better quantify the binding of WT versus Arg mutant PILRα binding to various ligands, we performed SPR analysis. The WT hPILRα-Fc and hPILRα R126-Fc were immobilized on a chip and their binding to hNPDC1, hCOLEC12, and mCD99 was compared (FIG. 5E). All three proteins showed strong binding with the WT hPILRα (FIG. 5E). However, little or no binding was observed with the mutant hPILRα, suggesting this conserved Arg site is necessary for binding of PILRα to its ligands (FIG. 5E).

Figures 1, 5F:
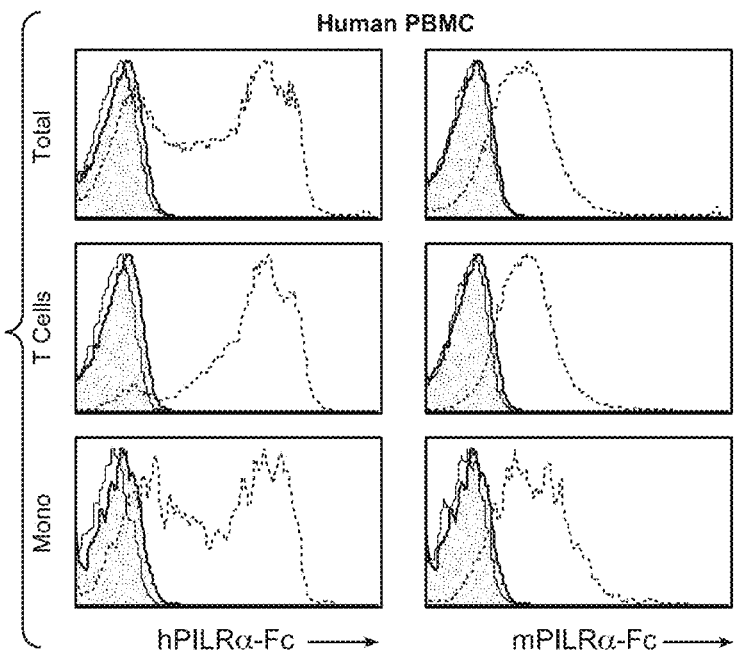
Figures 2, 5F:
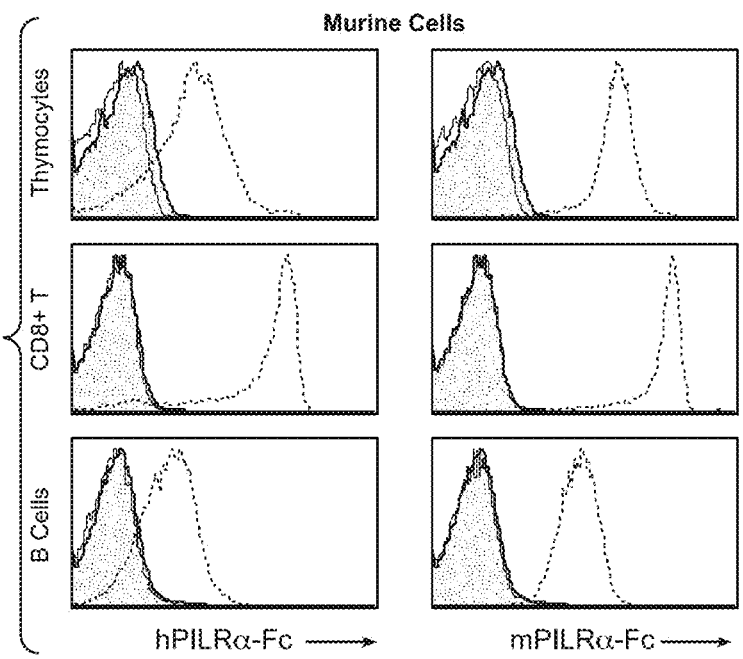
Figure 5G:
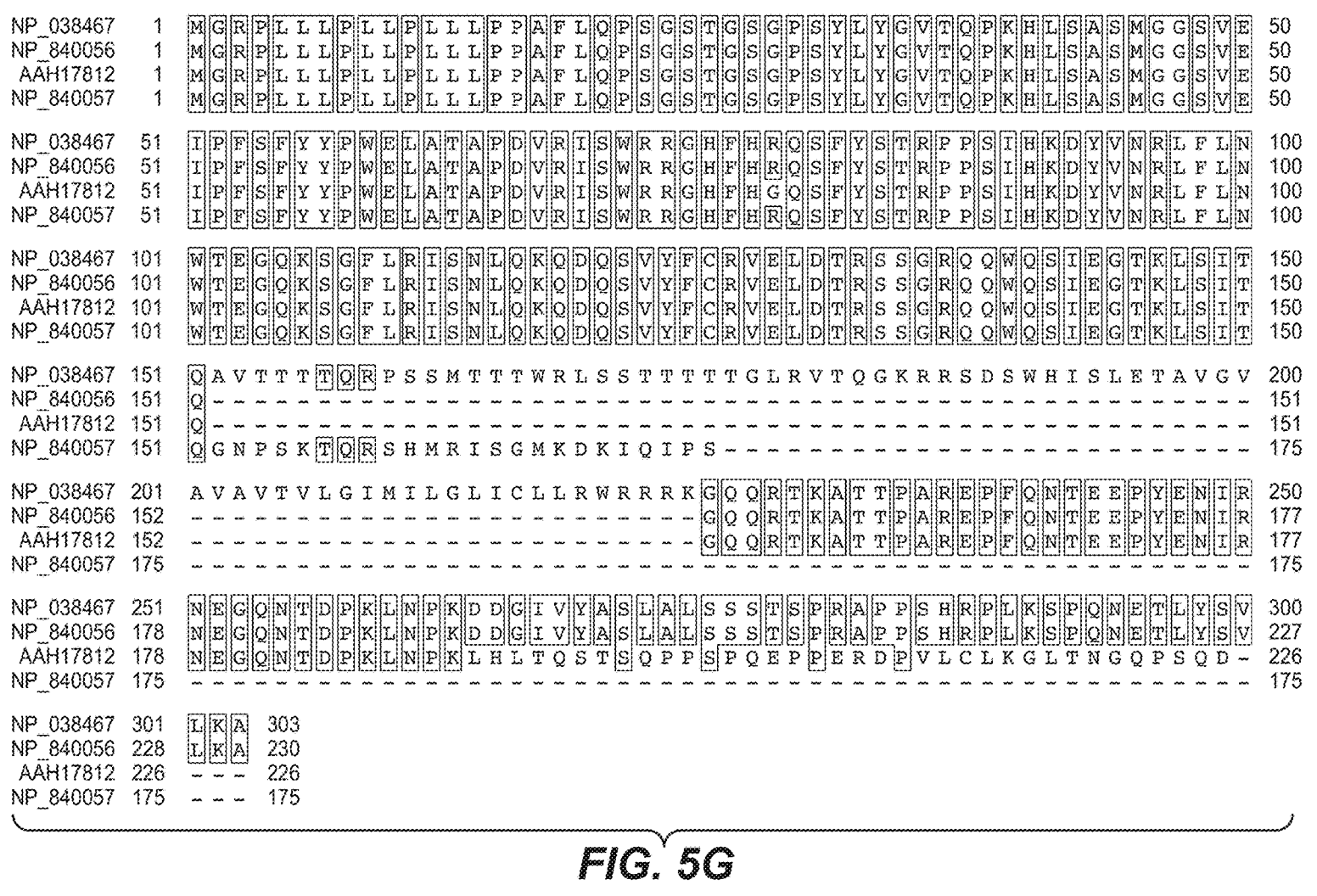
Figure 6:
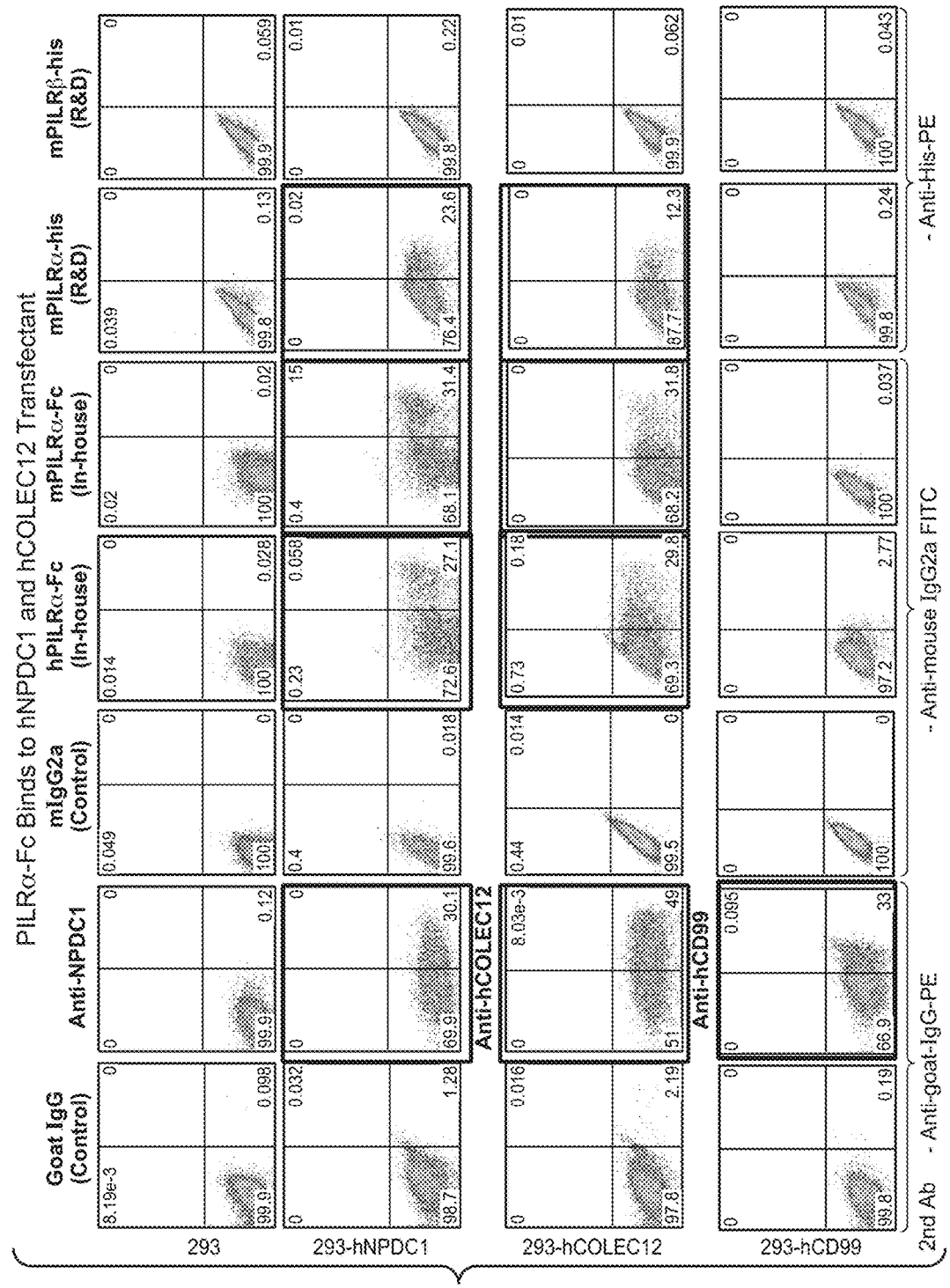
FIG. 6 illustrates the binding of PILRa-Fc to human NPDC1 and human COLEC12 expressing cells. HEK293T cells were transfected with human NPDC1, human COLEC12, human CD99 or vector. Transfected 293T cells were incubated with control immunoglobulins or the indicated the PILR constructs indicated on the top followed by an incubation with a second antibody and analyzed by flow cytometry.
Figure 7:
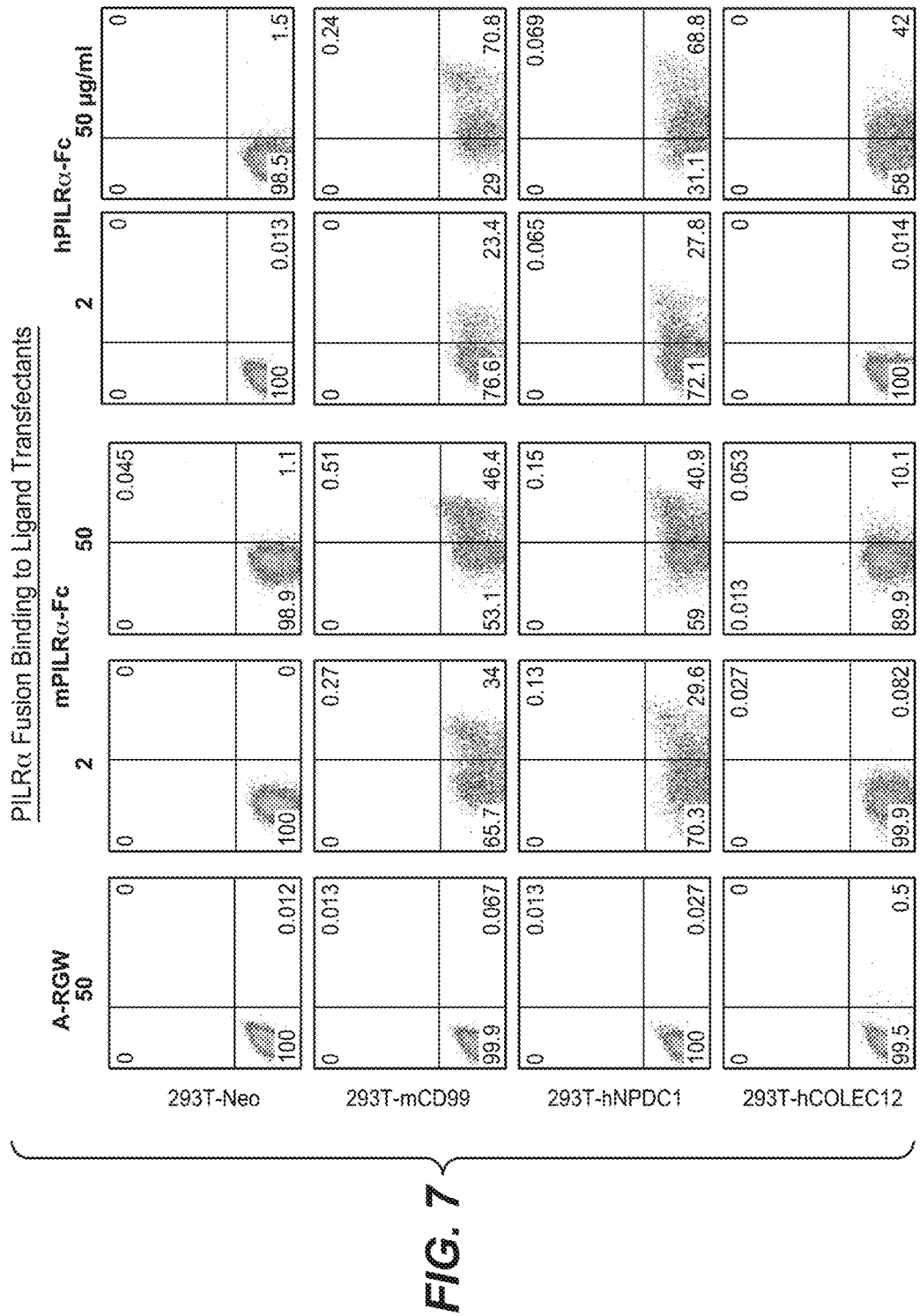
FIG. 7 illustrates the PILRa-Fc binding to ligand transfectants.
Figure 8A:
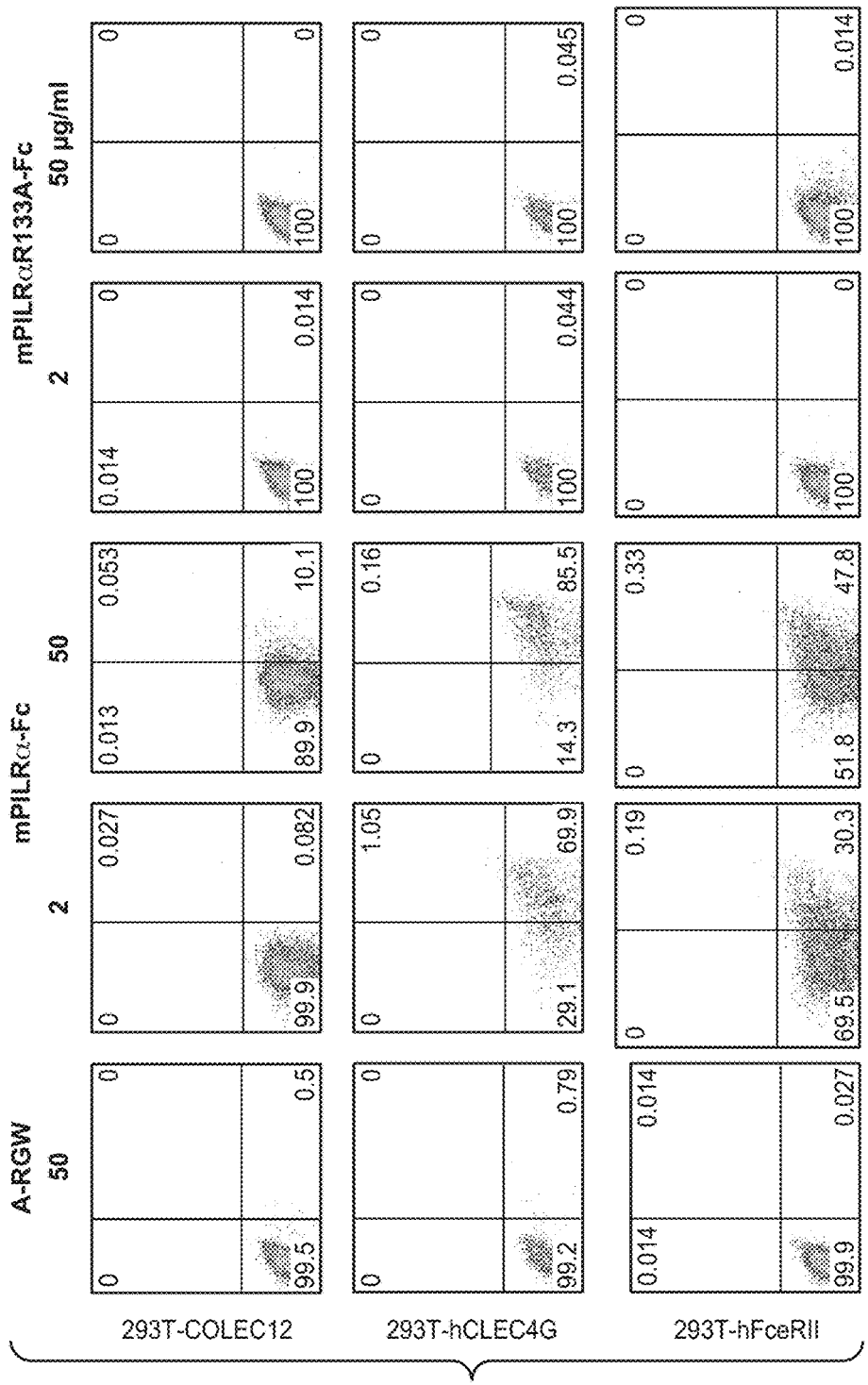
FIGS. 8A-8C illustrate the binding of (A) mouse and (B) human PILRa and the variant PILRa fusion proteins (i.e. R126A for human and R133A for mouse) to 3 different human ligands—COLEC12, CLEC4G and FceRII.
Figure 8B:
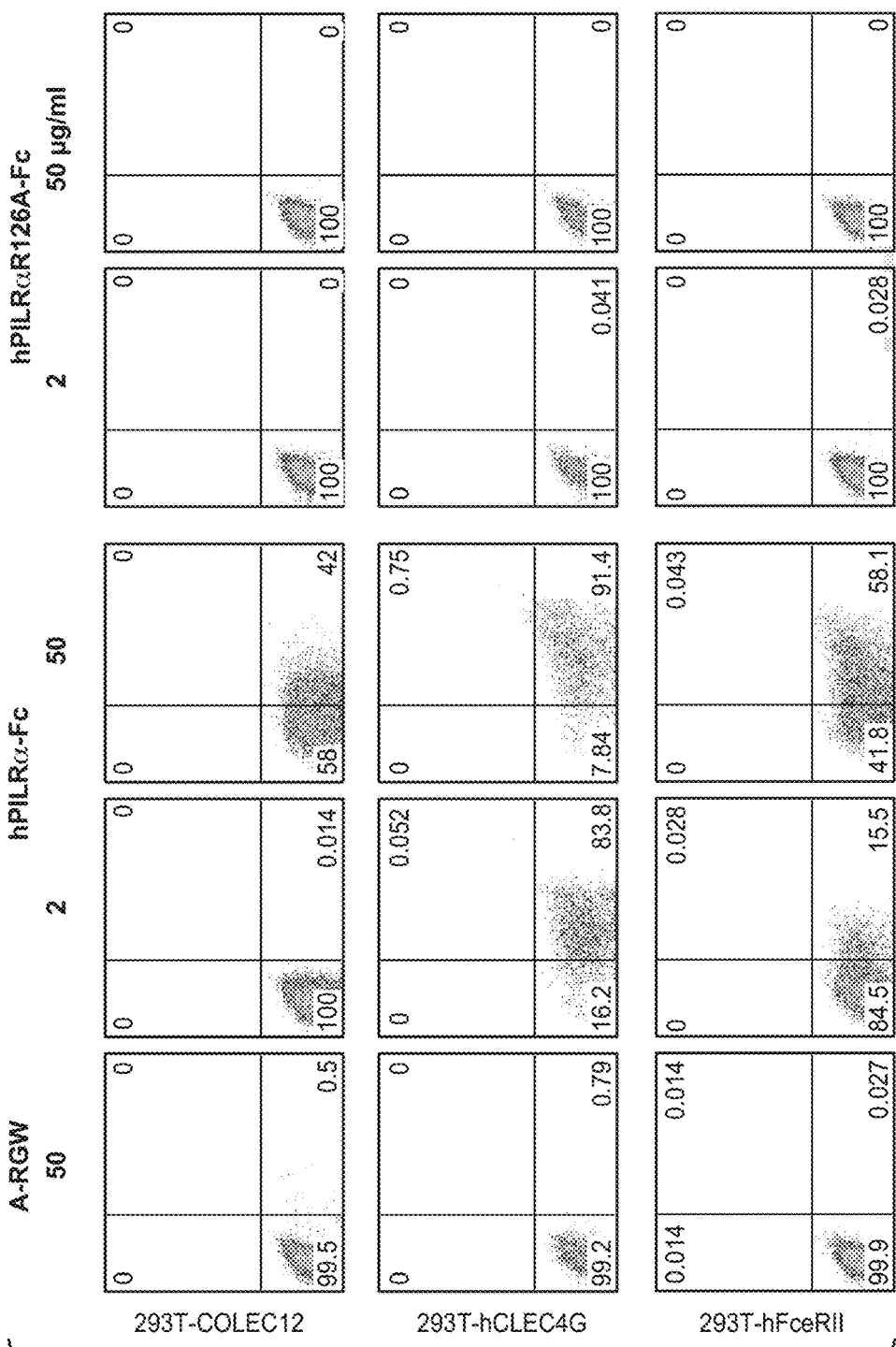
Figure 8C:
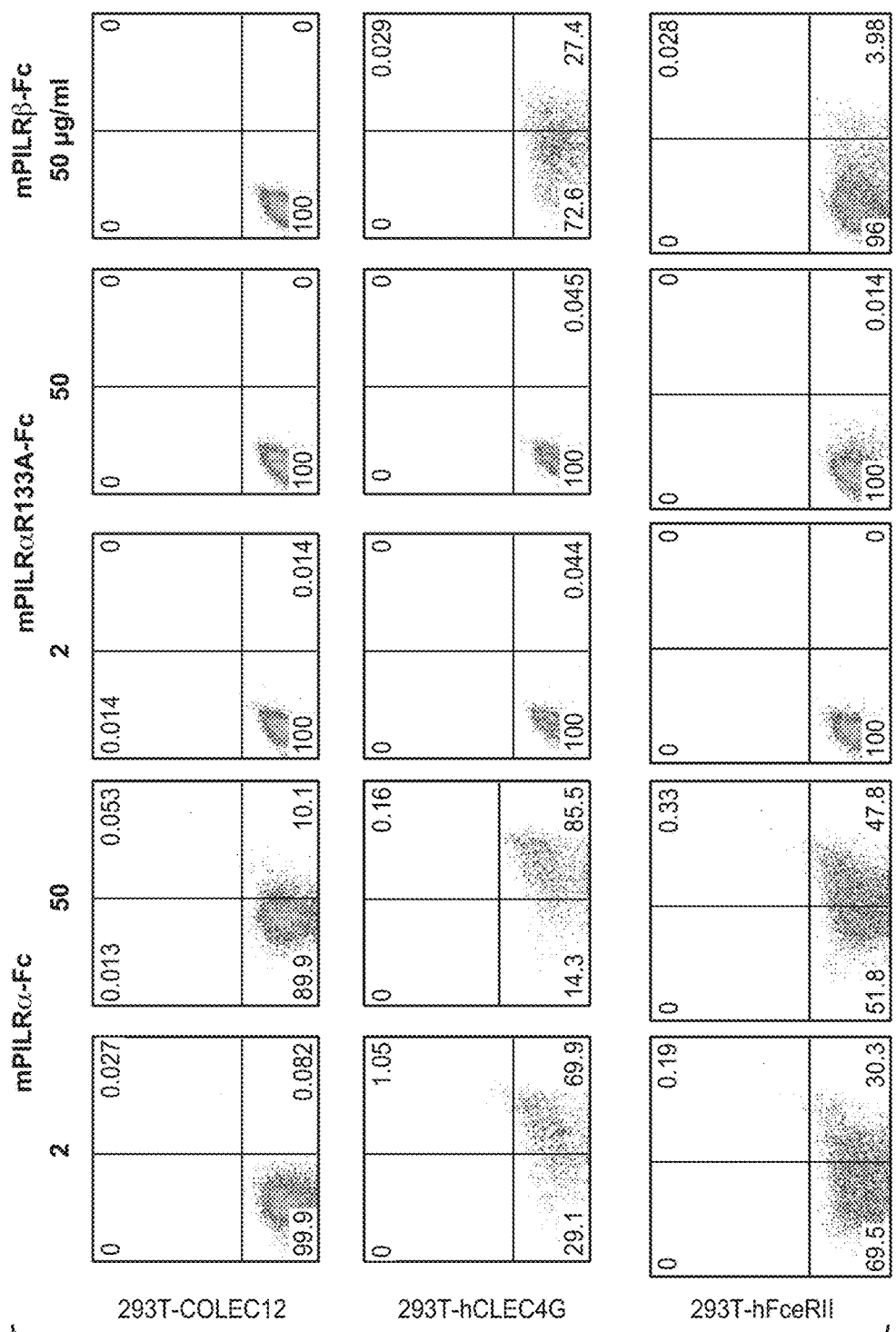
Figure 9A:
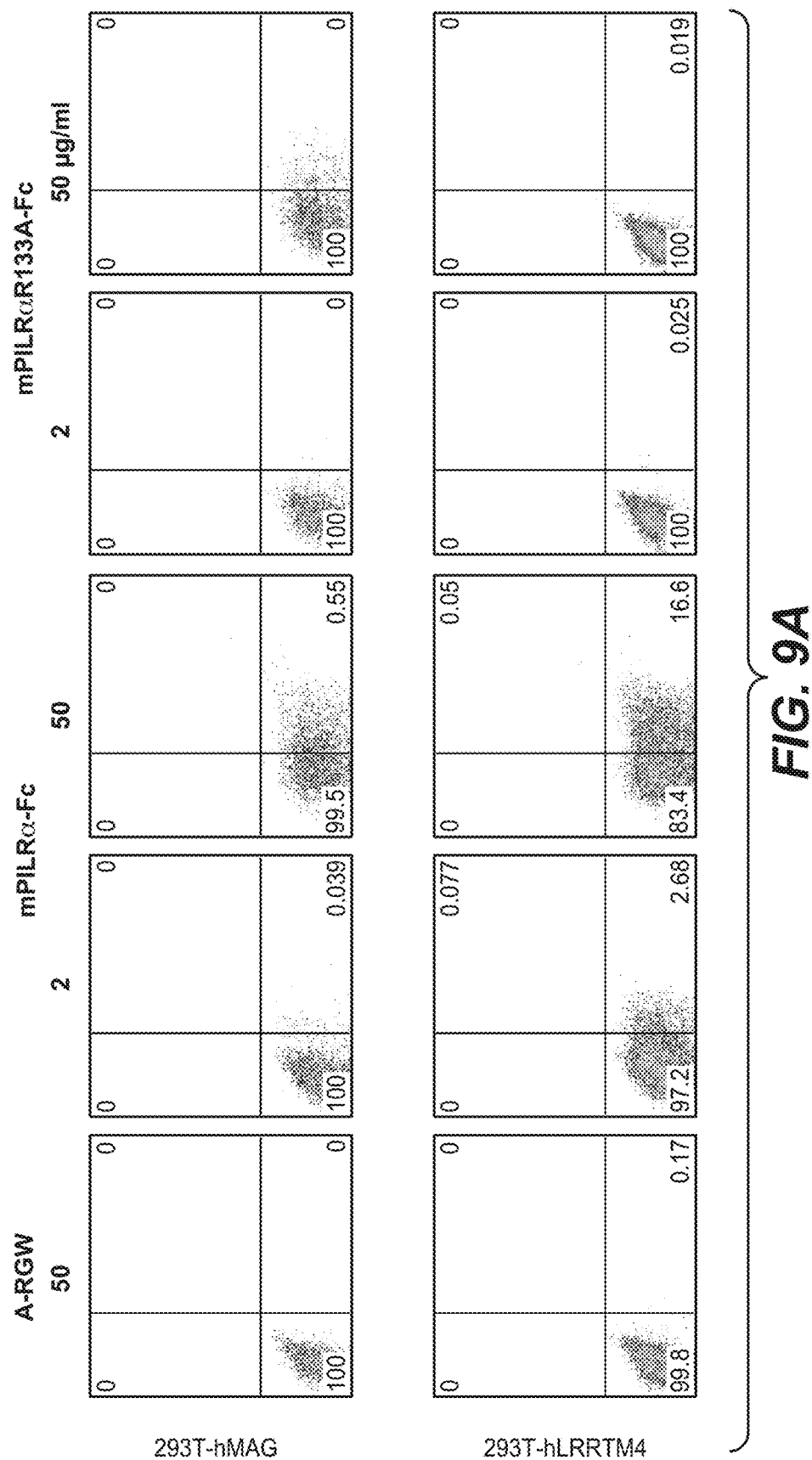
FIGS. 9A-9C illustrate the binding of (A) mouse and (B) human PILRa and the variant PILRa fusion proteins (i.e. R126A for human and R133A for mouse) to 3 different human ligands—MAG, FceRII and LRRTM4.
Figure 9B:
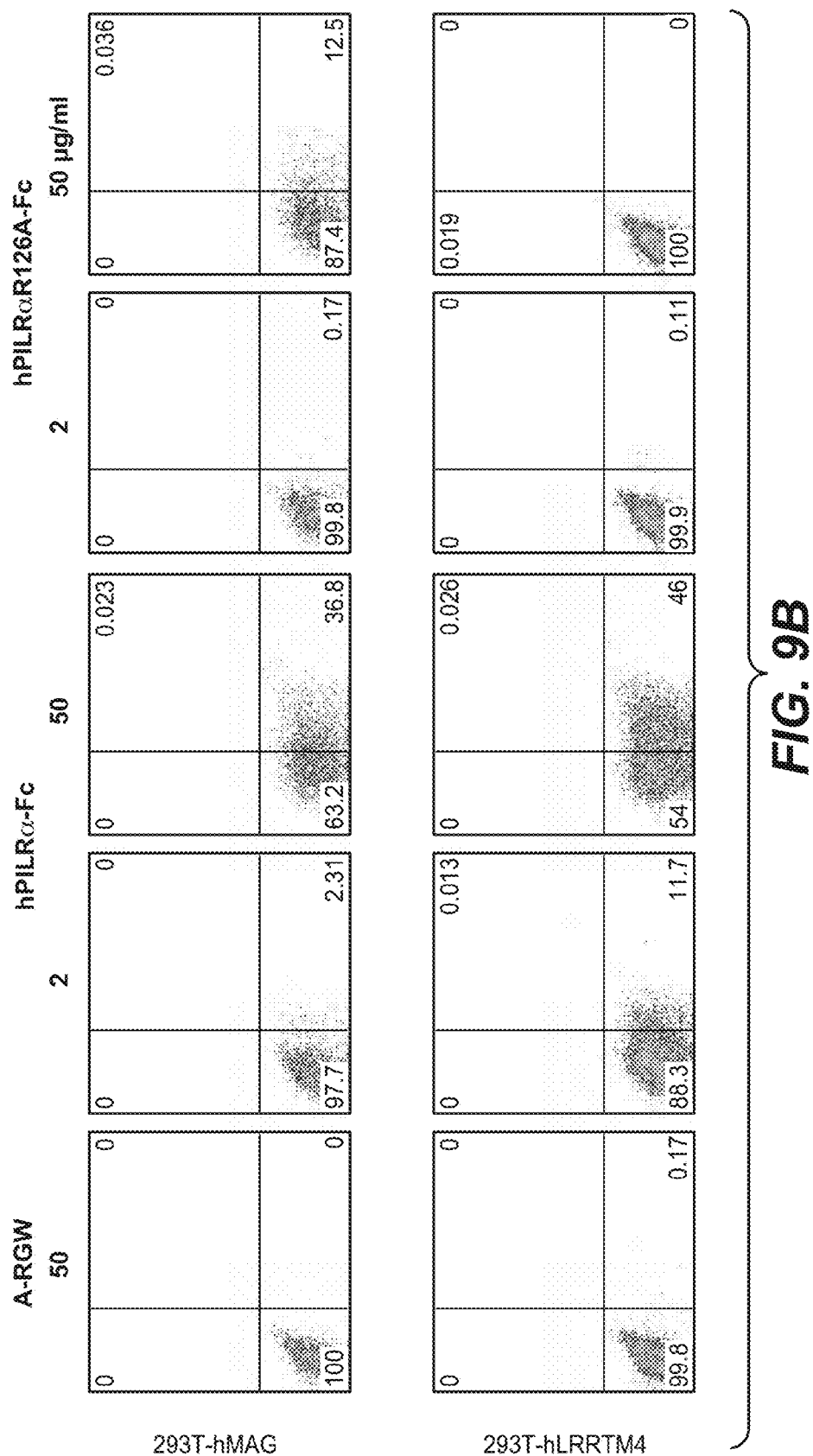
Figure 9C:
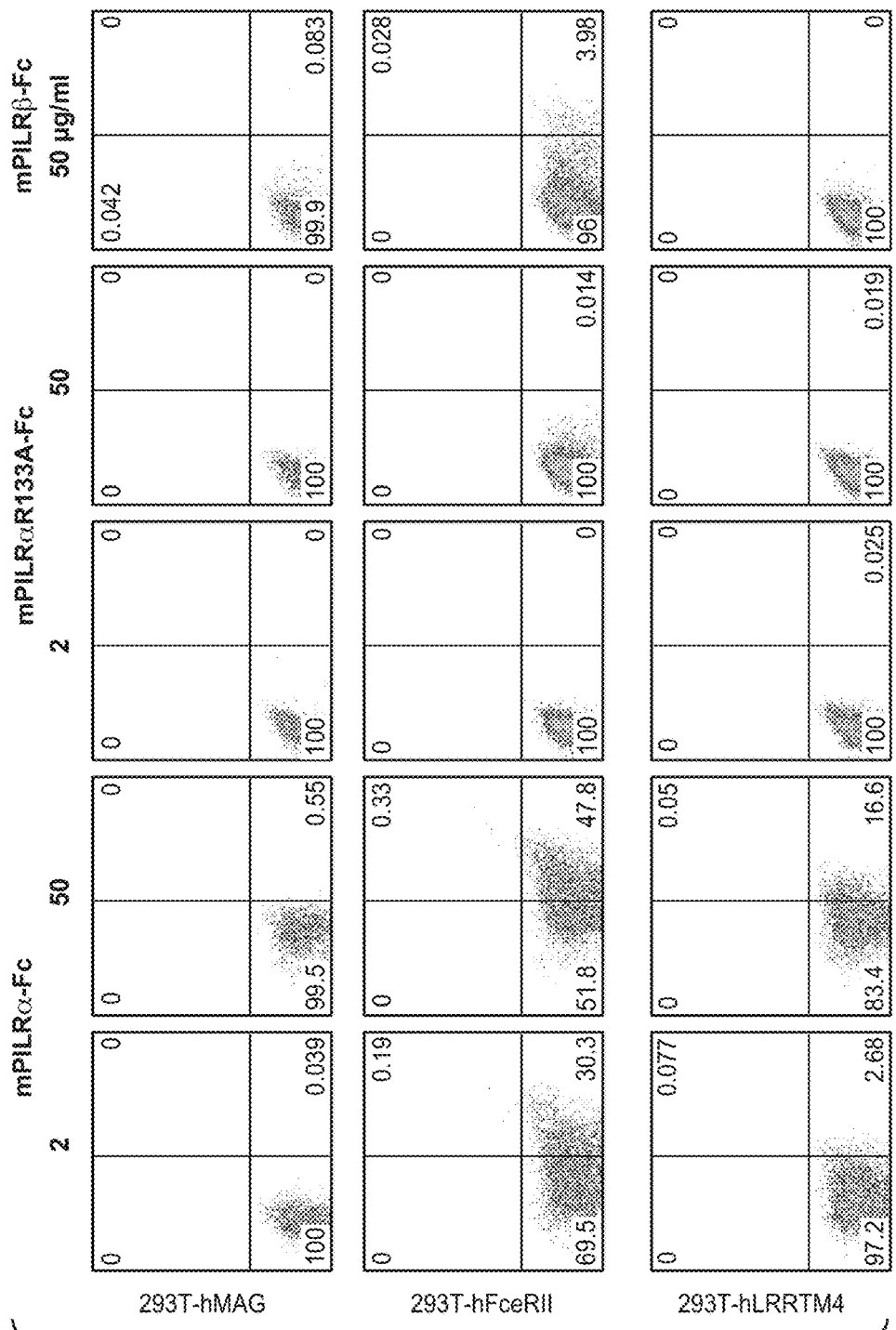
Figure 10A:
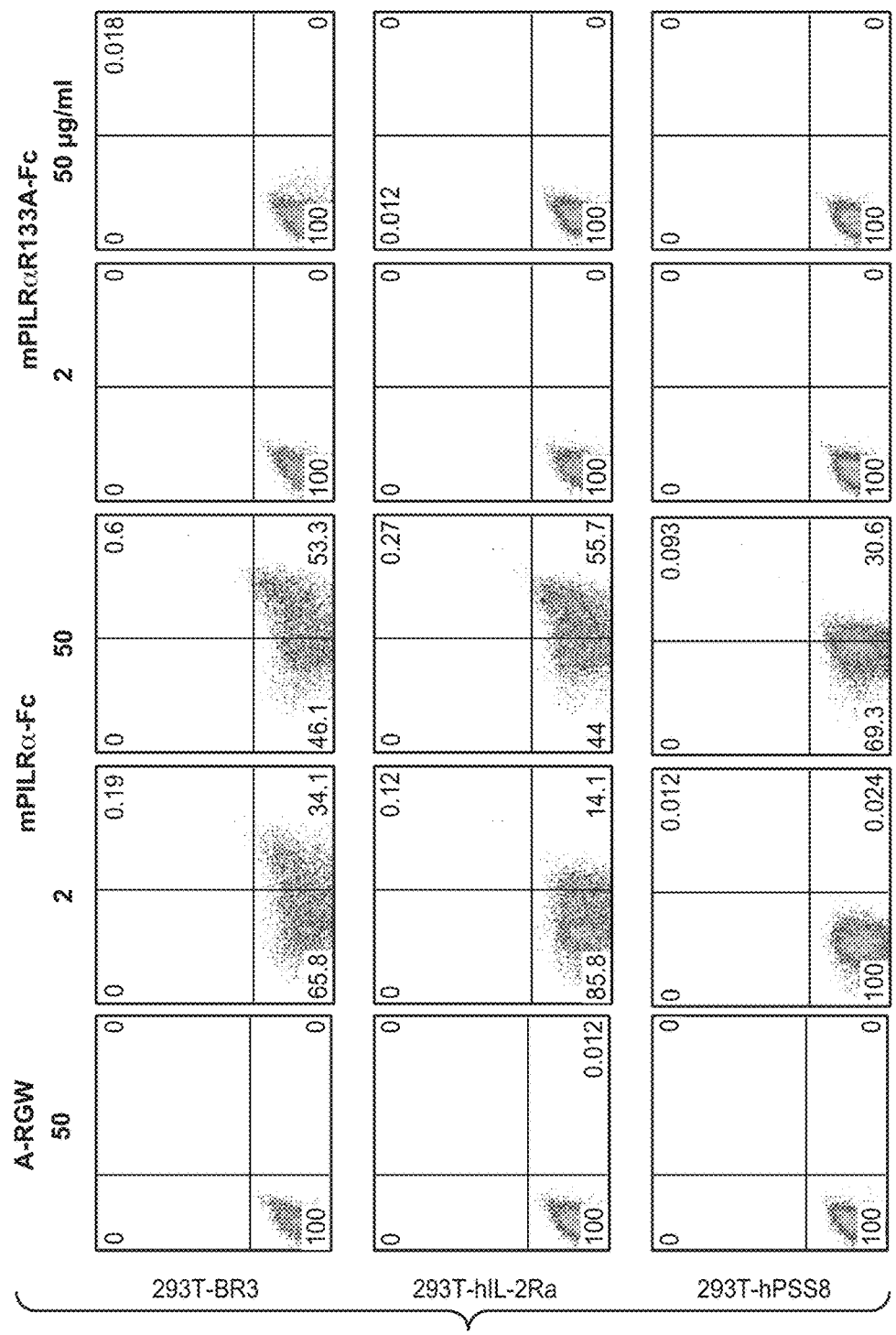
FIG. 10A-10C illustrate the binding of (A) mouse and (B) human PILRa and the variant PILRa fusion proteins (i.e. R126A for human and R133A for mouse) to 3 different human ligands—BR3, IL2Ra and PSS8.
Figure 10B:
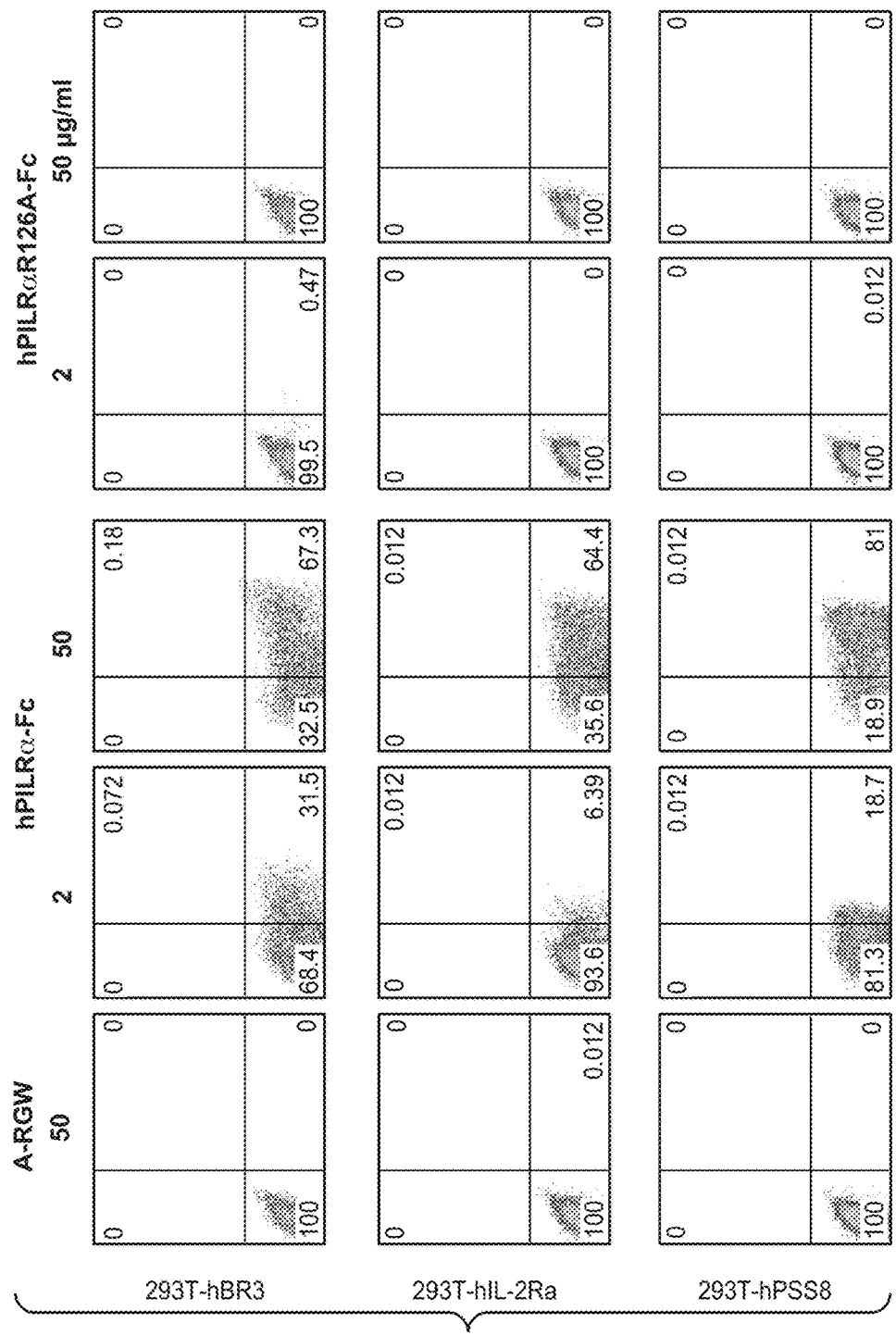
Figure 10C:
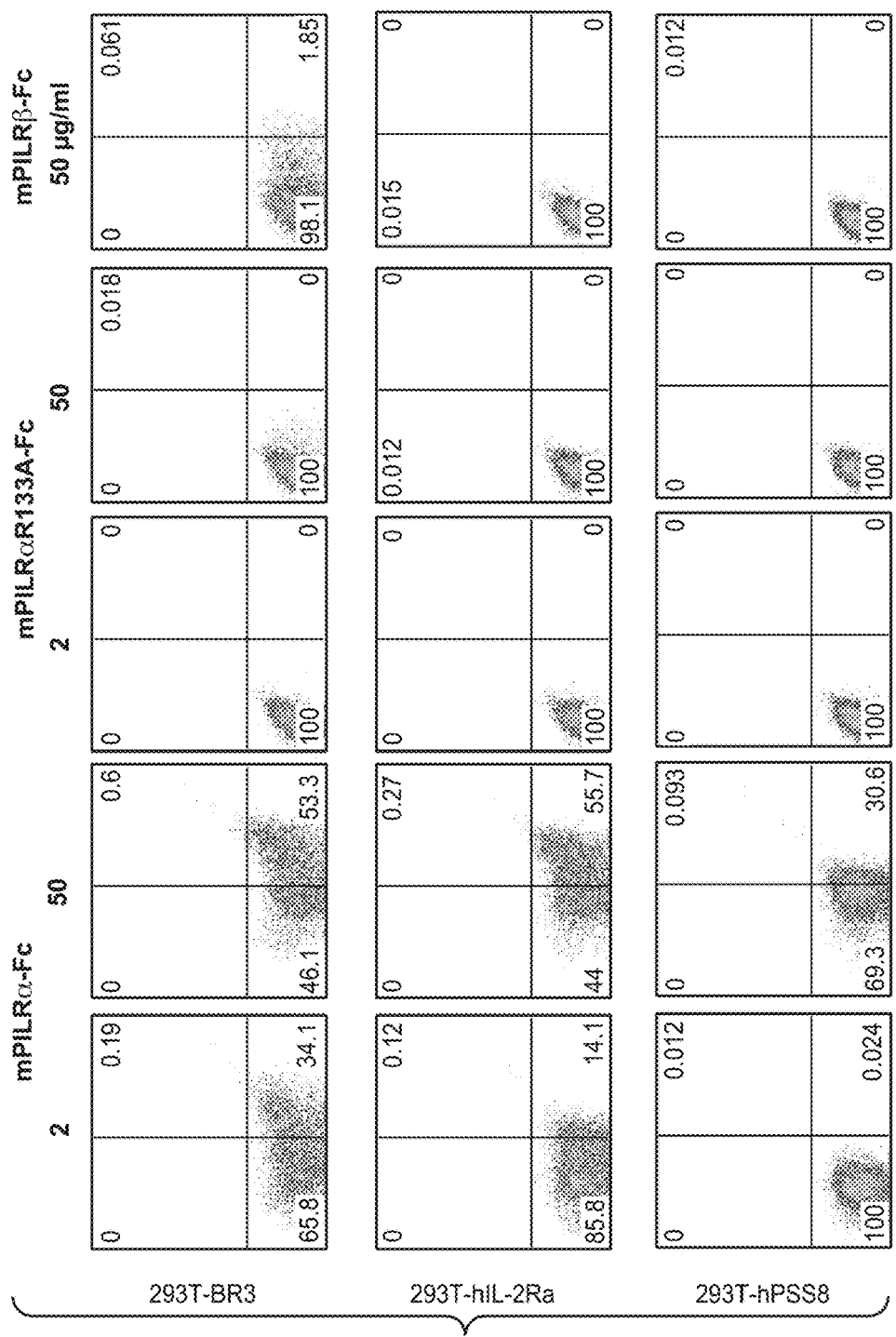
Figure 11:
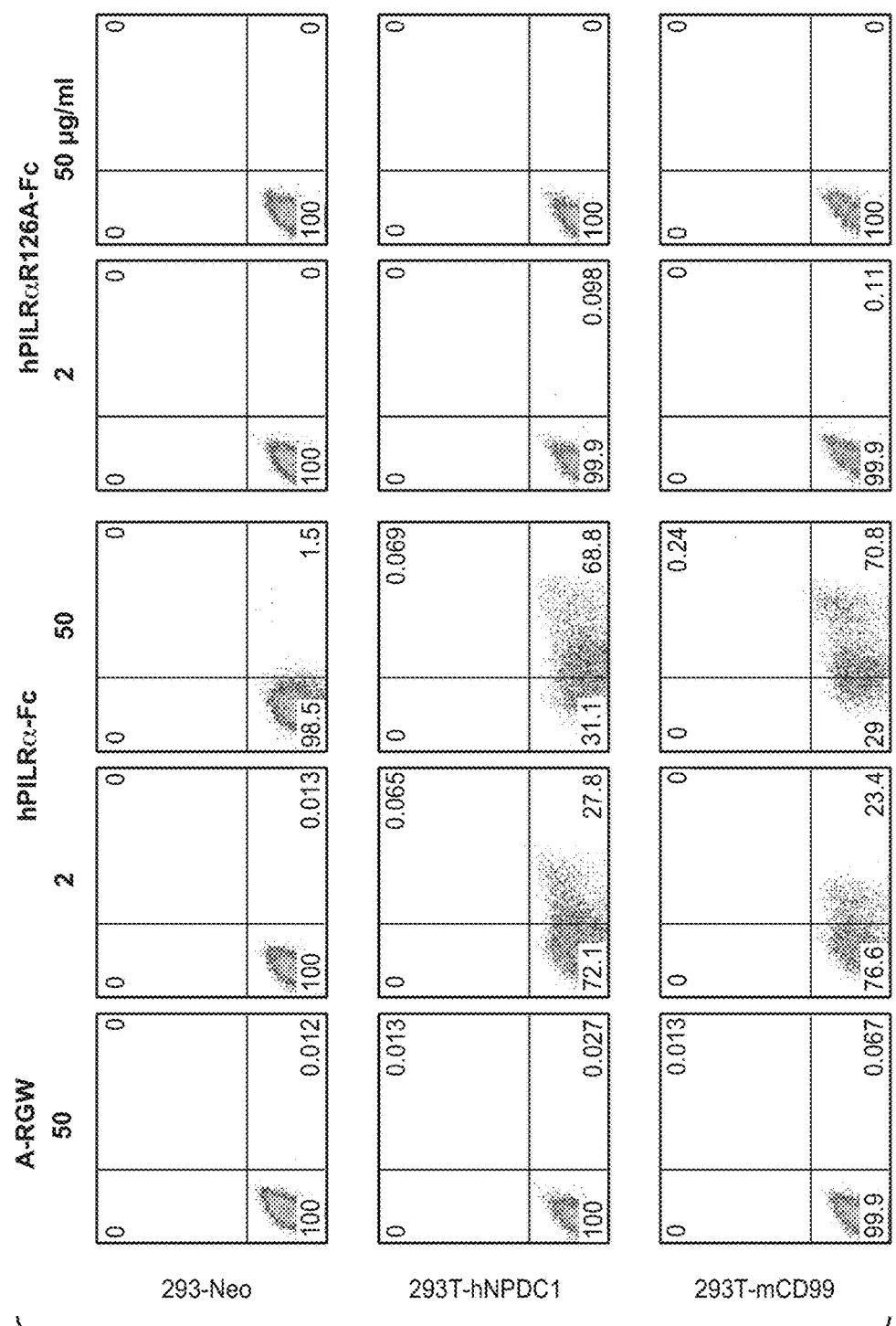
FIG. 11 is an extension of FIGS. 6-10C and illustrates the binding of anti-ragweed (control), hPILRa, and the variant hPILRa (R126A) fusion proteins to 2 different human ligands—hNPDC1 and mCD99. Neo indicates cells transformed with a neomycin containing vector used as a negative control. Note that the variant hPILRa does not bind any ligands tested or to the control.

Our data suggests that PILRα-ligand interactions require a conserved Arg motif on PILRα and specific sialylated decorations on the ligands. Since sialylation occur on many cell surface proteins, we predict PILRα ligands should be broadly expressed in various cells and hPILRαR126A/mPILRα133A should not bind to the natural ligands expressed on the surface of primary cells. To test this, we stained mouse and human hematopoietic cells with human or mouse PILRα-Fc. We found that both human and mouse PILRα-Fc bound to the majority of human PBMC (FIG. 5F-1). PILRα-Fc highly bound to human T cells and monocyte subsets (FIG. 5F-1). For murine cells, PILRα-Fc fusions highly bound to CD8$^+$ peripheral T cells and thymocytes, as well as peripheral B cells (FIG. 5F-2). However neither hPILRαR126A-Fc nor mPILRα133A-Fc can bind to human PBMCs (FIG. 5F-1), mouse thymocytes, or peripheral T and B cells (FIG. 5F-2). These results suggest that R126 in human PILRα and R133 in murine PILRα are required for their binding to cellular ligands expressed in primary cells.

Our study identifies the ARG126 (mouse ARG133) as a critical contact residue in hPILRα (FIG. 5A). Others have shown that TRP139 is also important in mediating hPILRα interaction with its ligand gB. Fan et al. (2010) *J Virol* 84, 8664-8672. Given the similarities of the binding residues between PILRα and Siglec family, we built a homology model of PILRα to gain insights into its contact residues.

The PILRα Sequence was aligned with the N terminal of the mouse Sialoadhesion from 1QFO.PDB using MOE2010.10 Protein Align application. Blosum62 was used as the alignment matrix, with tree-based build-up, Gap Start penalty of 7 and Gap Extend penalty of 1, Iteration limit of 100 and Failure limit of 10. The aligned structures were used to build a homology model using the Homology Model application in MOE2010.10. The crystal structure of the first chain in the SIGLEC1 was used as the template, while the ligand atoms were used as the 'environment' during model building. May et al. (1998) *Mol Cell* 1, 719-728; Munday and Crocker (1999) *J Leukoc Biol* 66, 705-711. The C, N-terminal outgaps were not built. A total of 25 models were built with fine minimization, and the final model was put through the Protonate3D procedure to detect the correct protonation states and was finely minimized at the end. The Merck force field (MMFF94x) with Born solvation method was used to reproduce the small molecule interactions of the active site. The active site-ligand interactions of SIGLEC1 and those of the PILRα model were rendered using the Ligand Interaction Diagram application of MOE2010.10. Clark and Labute (2007) *J Chem Inf Model* 47, 1933-1944. The active site-ligand contacts are coded according to Table 1.

TABLE 1

Ligand contacts of Siglec-1 and the PILRa model.

| | Siglec-1 | | PILRa | | |
|---|---|---|---|---|---|
| Contact Code | Active Site Residue/Atom | Ligand Residue/Atom | Active Site Residue/Atom | Ligand Residue/Atom | Comments |
| C01 | TRP2.Ring | SIA201.C11 | TYR33.Ring | SIA201.C11 | 3.6 Å vs 5.4 Å |
| C02 | TYR44.OH | GAL202.O6 | ARG74.NH1/NH2 | GAL202.O6 | [1] |
| C03 | ARG97.NH1 | SIA201.O1A | ARG126.NH1 | SIA201.O1A | identical |
| C04 | ARG97.NH2 | SIA201.O1B | ARG126.NH2 | SIA201.O1B | identical |
| C05 | SER103.O | SIA201.O4 | THR131 | SIA201.O4 | 2.8 Å vs 4.8 Å |
| C06 | | | ARG132 | SIA201.O4/O10 | Unique to PILRa |
| C07 | ASN104.CA | SIA201.O4 | GLN137.OE1 | SIA201.N5 | 5 Å vs 4.4 Å |

TABLE 1-continued

Ligand contacts of Siglec-1 and the PILRa model.

| | Siglec-1 | | PILRa | | |
|---|---|---|---|---|---|
| Contact Code | Active Site Residue/Atom | Ligand Residue/Atom | Active Site Residue/Atom | Ligand Residue/Atom | Comments |
| C08 | ARG105.O | SIA201.N5 | GLN138.O | SIA201.N5 | Identical |
| C09 | ARG105.NE | SIA201.O1A | GLN138 | SIA201.O1A | Identical |
| C10 | TRP106.Ring | SIA201.C9 | TRP139.Ring | SIA201.C9 | Identical |
| C11 | LEU107.O | SIA201.O9 | GLN140.O | SIA201.O9 | Identical |
| C12 | LEU107.N | SIA201.O8 | GLN140.N | SIA201.O8 | Identical |
| C13 | LEU107.CD2 | GAL202.O6 | GLN140.NE2 | GAL202.O6 | 3.8 Å vs 2.8 Å |
| C14 | ASP108 | | SER141 | | [2] |

Ligand atoms according to crystal structure (1QFO.pdb). Some corresponding atomic distances are shown under comments for Siglec-1 and PILRa respectively. [1] Contact possible via altered conformation; [2] Both residues about 5 Å away from SIA201.O9.

Despite the low sequence identity between SIGLEC1 and PILRα (FIG. 5A), it is clear that most of the contacts are strikingly similar, even when the active site residues are not identical. First, the C03, C04 contacts (SIGLEC1.ARG97 versus PILRα.ARG126) and the C10 contact (SIGLEC1.TRP106 versus PILRα.TRP139) are identical. SIGLEC1.SER103 and PILRα.THR131 both accept a hydrogen bond via their backbone carboxylate oxygens from the ligand Sialic acid O4 (contact C05). The backbone carboxylate oxygen of SIGLEC1.ARG105 and that of PILRα.GLN138 accept a hydrogen bond from N5 of the ligand sialic acid (contact C08). For contact C09, the guanidine nitrogen of this Arg in SIGLEC1 interacts with the carboxylate of ligand sialic acid O1A (4.1 Å), while the side chain amino in the corresponding residue (PILRα.GLN138) has the same contact, only slightly weaker (4.7 Å). The peptidic backbone of SIGLEC1.LEU107 and the corresponding PILRα.GLN140 have identical contacts with the ligand; their amino group contacts the ligand sialic acid O8 (coded as C11) and their carboxylate oxygen can accept a hydrogen bond from the ligand Sialic acid O9 (coded as C12). In comparison, the side chain amide group of PILRα.GLN140 is able to contact ligand galactose O6, which in SIGLEC1, the non-polar side chain of LEU108 has a non-favorable interaction with the ligand. This contact is coded as C13. The hydroxyl group of Tyrosine 44 of SIGLEC1 donates a hydrogen bond to O6 of the ligand galactose (contact code C02). The corresponding residue in PILRα (Arg73) cannot make this contact in the bent conformation observed in the model, where it seems to prefer to hydrogen bond with PILRα.PHE124.O, but manual rotation of the side chain along CG-CD can restore not one but two hydrogen bonds with the same oxygen in the ligand (galactose O6) with slight repulsion from PILRα.GLN140.NE2. Overall, it is likely that this contact (C02) can be present in PILRα, even stronger than SIGLEC1. Similarly, while SIGLEC1.TRP2 has proton-Pi interaction with the ligand Sialic acid C11 with the distance of 3.6A, the base conformation of the corresponding residue (PILRα.TYR33) is slightly further (5.4A), but a 30 degree rotation of the tyrosine side chain along CA-CB makes perfect overlay of the two aromatic systems, suggesting that the two receptors might have nearly identical contacts at this site too (C01). The PILRα.ARG132 which has no corresponding residue in SIGLEC1 crystal structure and shows no interaction with the ligand in the base conformation. However, after rotating the side chain along Cα-Cβ or Cβ-Cγ, the side chain can make hydrogen bonds with the ligand sialic acid O4, O10. These interactions (C06) are unique to PILRα suggesting that distinctive features exist between SIGLEC1 and PILRa receptors. It is interesting to note that the conserved interaction residues are predominantly located in carboxyl end of PILRα between 123 to 142 amino acids (FIG. 5A, arrows). In summary, PILRα active site is very similar to the SIGLEC1, with at least two additional hydrogen bonding contacts (Arg132, Gln140). These residues are exposed to solvent, even in the complex, suggesting possible contacts with the protein domains of other ligands.

Despite only 41% amino acid identity between the human and mouse PILRα ECDs, we find that both proteins can still interact with similar ligands and primary cells types. This suggests that a conserved interacting domain has been selected during evolution. Correspondingly, the alignment of PILRα sequences points to high degree of conservation among potential contact residues (FIG. 5A) some of which are shared with Siglecs family of receptors) (Arginine 126, Tryptophane 139). Tabata et al. (2008) *J Biol Chem* 283, 8893-8901. Our studies demonstrate that one common binding mechanism involves the recognition of one or several sialic acid modifications in all ligands by the conserved arginine site in mouse and human PILRα. We have come to this conclusion by showing that ligand fusion proteins including mCD99-Fc, hNPDC1-Fc and hCOLEC12-his do not bind to hPILRαR126A and mPILRαR133A expressed on cell surface while they all bind to the wild type human or mouse PILRα (FIG. 5B). Second, we find that mutated fusion proteins hPILRαR126A-Fc and mPILRαR133A-Fc do not bind to cell surface expressed ligands including mCD99, hNPDC1, hCOLEC12 and HSV1 gB (FIGS. 5 C-D). Third, our surface plasmon resonance analysis clearly shows that only wild type hPILRα-Fc but not mutated hPILRαR126A-Fc can bind to various ligands. Finally, hPILRαR126A-Fc and mPILRαR133A-Fc fail to interact with natural ligand(s) expressed in primary hematopoietic cells (FIG. 5F), suggesting this conserved Arg site is required for PILRα binding to all nature ligands. PILRα's uniform binding interaction mode by sialic acid recognition might have evolved to trigger a conserved signaling pathway and functional outcome depending on which ligand(s) are binding to PILRα. The convergence of PILRα sequences across different species may be indicative of receptor genes that are responding to evolutionary pressure provided by pathogens or unknown ligands.

A highly conserved and essential arginine residue (Arg97 in SIGLEC1) contacts the carboxylate group of sialic acid and two tryptophans that interact with the N-acetyl and glycerol moieties of N-acetyl neuraminic acid. May et al.

(1998) *Mol Cell* 1, 719-728; Munday et al. (1999) *J Leukoc Biol* 66, 705-711. Our functional data with arginine-mutated PILRα is consistent with a model in which Siglecs and PILRα have some similarity in their ligand interaction domains. Our analysis identifies arginine 126 as a key contact residue in hPILRα (Arg 133 in mPILRα) and its location appears to be critical to mediate PILRα interaction with sialic acid on gB as well as other ligands. Further support of this model is provided by recent data that the Tryptophan-139 residue is also critical for human PILRα binding to HSV1 gB. Fan et al. (2010) *J Virol* 84, 8664-8672. This Tryptophan-139 is not present in PILRβ and the converse mutation of L139W in PILRβ does not confer the ability to mediate binding to HSV1 gB, suggesting that there are other amino acids that play a role in the binding of PILRα with gB. Fan et al. (2010) *J Virol* 84, 8664-8672. Based on known structure of SIGLEC1:sialic acid complex, it is possible to speculate on how PILRα might recognize sialic acid containing ligands and rationalize the results of previously reported PILRα mutations. May et al. (1998) *Mol Cell* 1, 719-728. The homology model of the structure of PILRα identifies active site residues that are almost identical between the Siglecs and PILRα. In the absence of a crystal structure for PILRα, high similarities among the active site-ligand contacts between PILRα and SIGLEC1, even in case of non-identical residues allows us to confide in the homology model, and provides us with an expanded hypothesis for ligand binding of PILRα which can further analyzed via additional mutation studies. Structural resolution of PILRα in the context of sialylated proteins will be necessary to define the interaction domains. SIGLEC1 and multiple CD33-related Siglecs can interact with sialic acids on pathogens such as *N. meningitidis, C. jejuni*, group B *Streptococcus* and *Trypanosoma cruzi*. Crocker et al. (2007) *Nat Rev Immunol* 7, 255-266. It will be interesting to know whether PILRα could also directly interact with similar pathogens, which are known to carry sialylated sugar modifications in their surface structures.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating a subject having an paired immunoglobulin-like type 2 receptor alpha (PILRα) ligand-mediated inflammatory disease, said method comprising administering to said subject an effective amount of an anti-PILRα antibody, wherein said anti-PILRα antibody contacts human PILRα at an epitope comprising residue Arg126.

2. The method of claim 1, wherein said epitope further comprises one or more PILRα residues selected from the group consisting of Tyr33, Thr131, Arg132, Gln138, Trp139, and Gln140.

3. The method of claim 2, wherein said epitope comprises PILRα residue Arg132.

4. The method of claim 2, wherein said epitope comprises PILRα residue Gln140.

5. The method of claim 2, wherein said epitope comprises residues Arg126, Arg132, and Gln140.

6. The method of claim 5, wherein said epitope consists of PILRα residues Tyr33, Arg126, Thr131, Arg132, Gln138, Trp139, and Gln140.

7. The method of claim 1, wherein the anti-PILRα antibody is a monoclonal antibody.

* * * * *